US009517955B2

(12) United States Patent
Buschmann

(10) Patent No.: US 9,517,955 B2
(45) Date of Patent: Dec. 13, 2016

(54) SYSTEM AND METHOD FOR GENERATION OF POINT OF USE REACTIVE OXYGEN SPECIES

(71) Applicant: CLEAN CHEMISTRY, LLC, Boulder, CO (US)

(72) Inventor: Wayne Buschmann, Boulder, CO (US)

(73) Assignee: Clean Chemistry, LLC, Boulder, CO (US)

( * ) Notice: Subject to any disclaimer, the term of this patent is extended or adjusted under 35 U.S.C. 154(b) by 269 days.

(21) Appl. No.: 14/020,828

(22) Filed: Sep. 7, 2013

(65) Prior Publication Data

US 2014/0072653 A1    Mar. 13, 2014

Related U.S. Application Data

(60) Provisional application No. 61/698,550, filed on Sep. 7, 2012.

(51) Int. Cl.
*C02F 1/72* (2006.01)
*A01N 59/00* (2006.01)
(Continued)

(52) U.S. Cl.
CPC ............ *C02F 1/722* (2013.01); *A01N 37/16* (2013.01); *A01N 59/00* (2013.01); *C02F 1/4672* (2013.01);
(Continued)

(58) Field of Classification Search
None
See application file for complete search history.

(56) References Cited

U.S. PATENT DOCUMENTS 4,673,473 A    6/1987  Ang et al.
5,565,073 A    10/1996 Fraser et al.
(Continued)

FOREIGN PATENT DOCUMENTS

CN    102007230    4/2011
WO    2010059459    5/2010
(Continued)

OTHER PUBLICATIONS

International Search Report for PCT/US2012/040325 mailed Feb. 1, 2013.
(Continued)

*Primary Examiner* — Joseph D Anthony
(74) *Attorney, Agent, or Firm* — Meyertons, Hood, Kivlin, Kowert & Goetzel, P.C.; Eric B. Meyertons

(57) ABSTRACT

Systems and methods for generating reactive oxygen species formulations useful in various oxidation applications. Exemplary formulations include singlet oxygen or superoxide and can also contain hydroxyl radicals or hydroperoxy radicals, among others. Formulations can contain other reactive species, including other radicals. Exemplary formulations containing peracids are activated to generate singlet oxygen. Exemplary formulations include those containing a mixture of superoxide and hydrogen peroxide. Exemplary formulations include those in which one or more components of the formulation are generated electrochemically. Formulations of the invention containing reactive oxygen species can be further activated to generate reactive oxygen species using activation chosen from a Fenton or Fenton-like catalyst, ultrasound, ultraviolet radiation or thermal activation. Exemplary applications of the formulations of the invention among others include: cleaning in place applications, water treatment, soil decontamination and flushing of well casings and water distribution pipes.

14 Claims, 22 Drawing Sheets

(51) Int. Cl.
*A01N 37/16* (2006.01)
*C07C 409/26* (2006.01)
*C07C 407/00* (2006.01)
*C02F 1/467* (2006.01)
*C02F 1/66* (2006.01)
*C02F 103/00* (2006.01)
*C02F 103/06* (2006.01)
*C02F 103/10* (2006.01)

(52) U.S. Cl.
CPC ........... *C07C 407/00* (2013.01); *C07C 409/26* (2013.01); *C02F 1/66* (2013.01); *C02F 2103/002* (2013.01); *C02F 2103/06* (2013.01); *C02F 2103/10* (2013.01); *C02F 2305/02* (2013.01)

(56) References Cited

U.S. PATENT DOCUMENTS

| | | | |
|---|---|---|---|
| 6,183,623 | B1 | 2/2001 | Cisar et al. |
| 6,387,238 | B1 | 5/2002 | Merk et al. |
| 8,318,972 | B2 | 11/2012 | Buschmann et al. |
| 2001/0050234 | A1 | 12/2001 | Shiepe |
| 2003/0019758 | A1 | 1/2003 | Gopal |
| 2003/0024054 | A1* | 2/2003 | Burns .................. C11D 3/3907 8/115.51 |
| 2005/0183949 | A1 | 8/2005 | Daly |
| 2009/0152123 | A1 | 6/2009 | Butler et al. |
| 2009/0314652 | A1* | 12/2009 | Buschmann ............ C25B 15/08 205/349 |
| 2010/0176066 | A1* | 7/2010 | Budde .................... C02F 1/722 210/748.1 |
| 2010/0179368 | A1* | 7/2010 | Conrad .................. A01N 37/16 588/299 |
| 2011/0017066 | A1 | 1/2011 | Takeuchi et al. |
| 2012/0108878 | A1* | 5/2012 | Conrad .................. A01N 37/16 588/299 |
| 2012/0240647 | A1* | 9/2012 | Montemurro ............. C02F 1/66 71/12 |
| 2012/0322873 | A1 | 12/2012 | Atkins et al. |
| 2014/0072653 | A1 | 3/2014 | Buschmann |
| 2014/0131217 | A1 | 5/2014 | Buschmann |
| 2016/0068417 | A1* | 3/2016 | Buschmann ............ C02F 1/281 210/663 |

FOREIGN PATENT DOCUMENTS

| | | |
|---|---|---|
| WO | 2012166997 | 12/2012 |
| WO | 2013064484 | 5/2013 |
| WO | 2014039929 | 3/2014 |
| WO | 2014100828 | 6/2014 |
| WO | 2016037149 | 3/2016 |

OTHER PUBLICATIONS

International Search Report for PCT/US2013/058650 mailed Jan. 29, 2014.
Non-Final Office Action for U.S. Appl. No. 14/020,828 mailed on Jan. 20, 2016.
Notice of Allowance for U.S. Appl. No. 14/020,828 mailed on Mar. 30, 2016.
Non-Final Office Action for U.S. Appl. No. 14/122,185 mailed on Oct. 28, 2015.
Final Office Action for U.S. Appl. No. 14/122,185 mailed on Jul. 28, 2016.
CC03—First Office Action for Chinese Application No. 2013800580496 mailed on Feb. 4, 2016.
CC05—Supplementary Partial European Search Report for European Application No. EP 13 83 4576 mailed on May 10, 2016.
CC04—International Search Report for PCT/US2015/048722 mailed Feb. 8, 2016.

* cited by examiner

SYSTEM AND METHOD FOR GENERATION OF POINT OF USE REACTIVE OXYGEN SPECIES

CROSS-REFERENCE TO RELATED APPLICATIONS

This application claims the benefit of U.S. provisional application 61/698,550 filed Sep. 7, 2012, which is incorporated by reference herein in its entirety.

BACKGROUND

It is well known that a combination of reactive oxidant species can be beneficial to water treatment, cleaning, decontamination and remediation applications as they will combat a variety of substrate types which may be present and react with a variety of oxidation byproducts during their breakdown.

Hydroxyl Radicals

Of the common oxidants used in water treatment and remediation, the hydroxyl radical has the most positive standard oxidation potential of 2.80 V and is very effective at oxidizing a wide variety of substances. Hydroxyl radicals react very rapidly with a wide variety of oxidizable substrates. However, the hydroxyl radical lifetime is very short in aqueous media, merely several nanoseconds, and therefore must be produced with several tens of angstroms of a target substrate due to minimal diffusion path length. Hydroxyl radicals can further be quenched by undesirable reactions including reactions with radical quenchers, precursor oxidants and other hydroxyl radicals. For example, carbonate and bicarbonate ions present in natural waters are effective radical quenchers. Further, hydrogen peroxide and ozone can react with hydroxyl radicals; therefore while generating hydroxyl radicals from hydrogen peroxide and/or ozone precursors in water, the precursor is traditionally kept below 10 g/mL to avoid excessive consumption of hydroxyl radicals by the parent oxidant.

One issue with using hydroxyl radicals in water treatment is their ability to oxidize halide salts with much lower standard potentials and even oxidize sulfate diaion to the persulfate radical anion. A single electron oxidation of halide by a hydroxyl radical will produce hypochlorous acid, hypobromous acid and their hypohalite forms depending on the pH. However, an excess of hydroxyl radicals in the presence of hypohalites will further oxidize them in subsequent steps to chlorate, which is toxic, and bromate, which is carcinogenic.

Fenton Catalyst Activation

Fenton catalyst activation of hydrogen peroxide occurs when a reduced iron species, $Fe^{2+}$, is oxidized by hydrogen peroxide thereby producing hydoxyl radical, .OH, and an oxidized iron species, $Fe^{3+}$. The catalytic cycle is completed when hydrogen peroxide reduces $Fe^{3+}$ back to $Fe^{2+}$ thereby producing hydroperoxyl radical HOO., which is in equilibrium with superoxide. The Fenton process is summarized in Equations A and B, below.

$$Fe^{2+}+H_2O_2 \rightarrow Fe^{3+}+.OH+OH^- \qquad \text{Eq. A}$$

$$Fe^{3+}+H_2O_2 \rightarrow Fe^{2+}+.OOH+H^+ \qquad \text{Eq. B}$$

Similar Fenton-like chemistry occurs with other peroxides such as peroxyacetic acid. Iron sulfate is the most common Fenton catalyst and must be used at a pH near or below pH 4 to avoid excessive precipitation of $Fe^{3+}$ oxides and oxyhydroxides. Other iron catalyst forms such as iron minerals (e.g., magnetite) and chelated iron compounds have stability at higher pH.

Ultrasound Activation

Ultrasound activation of hydrogen peroxide in aqueous solution occurs when ultrasound waves induce cavitation of water forming bubbles, which leads to very high localized heating as cavitation bubbles collapse resulting in the thermal dissociation of hydrogen peroxide to hydroxyl radicals in Equation C.

$$H_2O_2 + heat \rightarrow 2.OH \qquad \text{Eq. C}$$

Similar thermal dissociation of peracids occurs to generate two different radical species in Equation D.

$$AcOOH + heat \rightarrow AcO. + .OH \qquad \text{Eq. D}$$

Ultraviolet Activation

Ultraviolet light activation of hydrogen peroxide occurs by the absorption of ultraviolet light, typically in the wavelength range of 180 to 220 nanometers, which leads to dissociation of hydrogen peroxide forming hydroxyl radicals summarized in Equation E.

$$H_2O_2 + UV\ light \rightarrow 2.OH \qquad \text{Eq. E}$$

Similar ultraviolet activation and dissociation of peracids occurs to generate two different radical species in Equation F.

$$AcOOH + UV\ light \rightarrow AcO. + .OH \qquad \text{Eq. F}$$

Thermal Activation:

Thermal activation of hydrogen peroxide can be conducted by impinging a liquid, spray, mist, vapor, or steam containing hydrogen peroxide upon a hot surface coated with a catalyst (e.g., silver oxide, iron oxide, ruthenium oxide, glass, quartz, Mo glass, $Fe_{3-x}Mn_xO_4$ spinels, $Fe_2O_3$ with Cu-ferrite, MgO and $Al_2O_3$.) and heated to above 200° C., to form hydroxyl radicals in Equation G.

$$H_2O_2 + heat + catalyst\ surface \rightarrow 2.OH \qquad \text{Eq. G}$$

The initial peroxide activation step in Equation G is followed by a series of radical propagation steps in the gas phase where intermediate radical species form such as the hydroperoxyl radical.

Singlet oxygen is a molecular oxygen in an excited electronic state. Singlet oxygen is most commonly produce in aqueous solutions by photolysis of dissolved oxygen directly by ultraviolet radiation or indirectly by energy transfer from a visible light photosensitizer dye to molecular oxygen. The use of photosensitizing dyes such as methylene blue, certain metalloporphyrins, semiconductors and other materials to generate singlet oxygen to degrade contaminants in water, disinfection and other uses are not practical for wastewater treatment due to degradation of dyes by singlet oxygen over time (i.e., photobleaching) and at elevated concentrations.

Another common method of singlet oxygen generation is by chemical reactions where singlet oxygen is released as a byproduct, including the Haber-Weiss reaction, reaction between hydrogen peroxide and hypochlorite, decomposition of 9,10-diphenylanthracene endoperoxide and a reaction between neutral and ionized forms of organic peroxyacids. However, these methods cause the rapid quenching of the singlet oxygen species by physical and chemical pathways. Chemical quenching reactions occur when singlet oxygen is consumed by a non-beneficial chemical reaction involving electron transfer. Physical quenching reactions occur by radiative or non-radiative relaxation of the excited state by physical contact with its surroundings without electron transfer. In these methods, excess hydrogen peroxide is a very effective quenching agent resulting in little or no oxidative activity from singlet oxygen generated in the presence of significant concentrations of hydrogen peroxide. When hydrogen peroxide is present in significant concentrations, as is the case for most commercially produced peroxyacetic acid, singlet oxygen is rapidly quenched by hydrogen peroxide, which reduces singlet oxygen concentration. Chlorine, azide, certain tertiary amines and beta-carotene are other known examples of singlet oxygen quenchers.

Peroxyacetic acid (i.e. AcOOH) is typically made by commercial producers by an equilibrium reaction between concentrated acetic acid (i.e. AcOH). The equilibrium reaction can be catalyzed by a mineral acid such as sulfuric acid at a pH<1 and occurs over a time period of several hours to several days depending on the concentration of hydrogen peroxide, acetic acid and acid catalyst. There is typically a significant concentration of residual hydrogen peroxide and acetic acid in peroxyacetic acid made by the equilibrium reaction. For example, the [peroxyacetic acid][$H_2O$]/[acetic acid][$H_2O_2$] concentration ratios are often between 1.8 and 2.5 for commercial grades between 5 and 30 wt % peroxyacetic acid. Peroxyacetic acid solutions are generally unstable at room temperature and pose a significant fire hazard. Therefore peroxyacetic acid is typically produced on site by the equilibrium process or shipped in vented containers from a producer. Peroxyacetic acid may be distilled under reduced pressure to obtain a pure form with low hydrogen peroxide residual, however, distillation is generally not practical and can create a severe explosion hazard.

Superoxide is the radical anion form of molecular oxygen and is a mild reducing agent with a standard oxidation potential commonly reported as −0.33 V in aqueous environments. Superoxide can be produced in bulk as the anhydrous potassium salt, $KO_2$, which rapidly reacts with water or carbon dioxide releasing molecular oxygen and potassium hydroxide or potassium carbonate, respectively. Superoxide can also be produced in situ by ultraviolet irradiation of oxygen containing solutions including seawater, enzymatic processes and by electrochemical reduction of oxygen. For large scale applications superoxide is typically supplied as a bulk chemical or generated in situ from activated hydrogen peroxide reactions. Potassium superoxide is a water-sensitive hazardous material and combustion aid, which may be prohibitive barriers to its use in some locations. Also, potassium superoxide must be fed into a treatment process as a solid feed, which can be problematic due to water absorption, caking and clogging of solid feeders.

Several common issues arise with conventional reactive oxygen species formulations including, for example, limited shelf life, low mobility of oxidants and/or catalysts; highly acidic or alkaline oxidants which cause significant changes in the natural soil or groundwater pH; limited options for oxidant types available from a single product or system; and logistic, cost, permitting or safety issues associated with bringing large quantities of strong oxidizers and hazardous chemicals on site. Additionally, the use of conventional iron-based hydrogen peroxide Fenton catalysts and sodium persulfate activators, such as iron (II) sulfate, require an acidic pH of less than 4 to be active, but as the pH increases toward neutral pH levels the precipitation of iron oxides and oxyhydroxides occurs. Precipitated iron can cause pore plugging in soils, fouling and staining equipment and can promote population blooms of iron bacteria which cause biofouling of soils, and accelerated microbial corrosion of steel well casings, pipes and equipment.

Well Flushing:

Oil and gas production wells, groundwater wells and water pipelines are often hyper-chlorinated to control microbial growth and slime buildup with varying degrees of success due to issues such as organic residues, slime buildup and incompatible pH. Chlorine and hypochlorite are readily sequestered by organics residues and slime materials, which protect active microbes from being killed. Hypochlorite also rapidly loses its efficacy above pH 7.5, below the natural pH of seawater and many ground water types with pH levels greater than 8.

SUMMARY OF THE INVENTION

The invention provides reactive oxygen species formulations as well as methods for making and using such formulations.

In an embodiment, the invention provides a method for generating a reactive oxygen species formulation comprising (1) generating an alkaline hydrogen peroxide solution from the combination of an alkali and a hydrogen peroxide concentrate; (2) mixing the alkaline hydrogen peroxide solution with an acyl or acetyl donor such that a peracid concentrate is produced, wherein the peracid concentrate has minimal hydrogen peroxide residual; and (3) adjusting the peracid pH level to the activated pH range for generating the reactive oxygen species. The reactive oxygen species formulation can be a singlet oxygen precursor formulation. In an embodiment, the hydrogen peroxide solution is generated using a molar ratio of $H_2O_2$ to alkali in the range of 1:1.2 to 1:2.5. The molar ratio of $H_2O_2$ to alkali can be 1:1.2 to 1:1.4, 1.4 to 1:2.0 or 1:2.0 to 1:2.5. In an embodiment, the peracid concentrate is produced by mixing the alkaline hydrogen peroxide solution with the acyl or acetyl donor such that the molar ratio of hydrogen peroxide to acyl or acetyl donor ranges from 1:1.25 to 1:4. The molar ratio of hydrogen peroxide to acyl or acetyl donor can be 1:1.25 to 1:1.5, 1:1.5 to 1:2, or 1:2 to 1:4. In an embodiment, the activated pH range is in the range of pH 6.5 to 12.5. The activated pH range can be 6.5 to 9.5 or 9.5 to 12.5. In an embodiment, the method further comprises entraining byproducts of the reaction between the alkaline hydrogen peroxide solution and the acyl or acetyl donor. In an embodiment, the method further comprises diluting the peracid concentrate. In an embodiment, the method further comprises mixing the peracid solution with an additives concentrate. In an embodiment, the method comprises storing the alkaline hydrogen peroxide in a holding tank for immediate or future use. In an embodiment, mixing the alkaline hydrogen peroxide solution with an acyl or acetyl donor produces a concentrated peracid solution.

In an embodiment, the invention provides a method for generating a reactive oxygen species formulation wherein an alkaline hydrogen peroxide concentrate is electrochemically generating, the electrochemically generated alkaline hydrogen peroxide concentrate is combined with an acyl or acetyl donor to produce a peracid concentrate, wherein the peracid concentrate has minimal hydrogen peroxide residual and the peracid solution is combined with an acid concentrate to produce the reactive oxygen species formulation having a pH level in the activated pH range. In an embodiment, the electrochemically generated alkaline hydrogen peroxide concentrate has a pH in the range of 12.0 to 13.0, and a percent weight of hydrogen peroxide in the range of 0.1 to 3 wt %. In an embodiment, the acid concentrate is co-generated during electrochemically generating the alkaline hydrogen peroxide concentrate. The co-generated acid concentrate can have 0.1 wt % to 20 wt % acid. In an embodiment, the peracid concentrate is produced by mixing the electrochemically generated alkaline hydrogen peroxide solution with the acyl or acetyl donor such that the molar ratio of hydrogen peroxide to acyl or acetyl donor is in the range of 1:1.25 to 1:4. The molar ratio of hydrogen peroxide to acyl or acetyl donor can be 1:1.25 to 1:1.5, 1:1.5 to 1:2, or 1:2 to 1:4. In an embodiment, the activated pH range is in the range of pH 6.5 to 12.5. The activated pH range can be 6.5 to 9.5 or 9.5 to 12.5. In an embodiment, the method further comprises entraining byproducts of the reaction between the alkaline hydrogen peroxide solution and the acyl or acetyl donor. In an embodiment, the method further comprises diluting the peracid concentrate. In an embodiment, the method further comprises mixing the peracid solution with an additives concentrate. In an embodiment, the method comprises storing the alkaline hydrogen peroxide in a holding tank for immediate or future use. In an embodiment, mixing the alkaline hydrogen peroxide solution with an acyl or acetyl donor produces a concentrated peracid solution.

In an embodiment, the invention provides a method for generating a superoxide reactive oxygen species formulation comprising electrochemically co-generating a solution containing hydrogen peroxide and superoxide. In an embodiment, the formulation containing co-generated hydrogen peroxide and superoxide has a pH of 8-13. In an embodiment, the molar ratio of superoxide to hydrogen peroxide co-generated ranges from 0.01:1 to 10:1. In an embodiment, the pH of the superoxide solution is adjusted by addition of an acid concentrate. In an embodiment, the acid concentrate is co-generated during the step of electrochemically generating the superoxide solution. In an embodiment, the superoxide solution is combined with an additives concentrate. In an embodiment, the superoxide solution is diluted. More specifically, the superoxide solution is diluted to a near point of use concentration. In an embodiment, co-generation of hydrogen peroxide and superoxide produces at least one radical species which can among others be a hydroperoxyl radical and/or a hydroxyl radical.

In related embodiments, the methods for generating reactive oxygen formulations further comprise further activating the reactive oxygen species using activation chosen from the group a Fenton or Fenton-like catalyst, ultrasound, ultraviolet radiation and thermal activation. More specifically activation produces radical species, which can be the hydroxyl radical.

In an embodiment, a reactive oxygen formulation produced by the methods herein is distributed to its point of use. The form in which the reactive oxygen formulation is distributed can as a liquid, an ice, a foam, an emulsion, a microemulsion or an aerosol. The invention also provides reactive oxygen formulations for point of use applications which are appropriately formulated for application by injection, flooding, spraying, and/or circulation.

In specific embodiments, in the methods herein the reactive oxygen species is singlet oxygen. The invention also provides formulations containing reactive oxygen species, particularly those prepared by the methods of the invention. In specific embodiments, the reactive oxygen species formulations are singlet oxygen formulations. Such formulations can be concentrated or can be diluted. Diluted formulation can be prepared by addition of water.

In specific embodiments, the invention provides a reactive oxygen species precursor comprising a peracid concentrate comprising a mixture of alkaline hydrogen peroxide and an acyl or acetyl donor. The reactive oxygen species precursor can be a diluted singlet oxygen precursor. More specifically, the diluted singlet oxygen precursor has a pH in the range 6.5 to 12.5, in the range 6.5 to 9.5 or in the range 9.5 to 12.5. The reactive oxygen species precursor can be a concentrated singlet oxygen precursor. More specifically, the concentrated singlet oxygen precursor has a pH in the range 6.5 to 12.5, in the range 6.5 to 9.5 or in the range 9.5 to 12.5.

In an embodiment, the invention provides a peracid formulation capable of generating singlet oxygen, particularly where the singlet oxygen is generated by the reaction of alkaline hydrogen peroxide and an acyl or acetyl donor. The invention also provides a method for making such peracid formulations. Preferably the peracid formulation has minimal hydrogen peroxide residual to minimize quenching of the singlet oxygen. In an embodiment, the peracid formulation has a pH in the activated pH range. In a specific embodiment, in the peracid formulation, the ratio of alkaline hydrogen peroxide to acyl or acetyl donor reactive groups is in the range 1:1.25 to 1:2 to 1:4. More specifically, the ratio of alkaline hydrogen peroxide to acyl or acetyl donor reactive groups is 1:1.25 to 1:1.5, 1:1.5 to 1:2, or 1:2 to 1:4. The peracid formulation can have pH in the range 6.5 to 12.5, 6.5 to 9.5 or 9.5 to 12.5. In a specific embodiment, the peracid formulation is further reacted with an acid concentration resulting in both peracetic acid and paracetic acid anion, wherein the reaction of the peracid formulation and acid concentrate comprises the reaction:

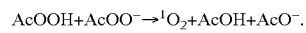

$AcOOH + AcOO^- \rightarrow {}^1O_2 + AcOH + AcO^-$.

Peracid formulation of the invention can be distributed in any suitable form and can be distributed in the form of a liquid, an ice, a foam, an emulsion, a microemulsion or an aerosol. The peracid formulations of the invention can be applied to a point of use by an application chosen from injection, flooding, spraying, and circulation. The peracid formulations of the invention can be used for clean-in-place applications in food, dairy, beverage and biopharma; hard surface cleaning; decontamination; remediation of soil and groundwater; cleaning of membrane filtration systems; flushing of well casings and water distribution pipes; and in-situ chemical oxidation, among others.

In an embodiment, the invention provides an electrochemically generated, reactive oxygen species solution comprising superoxide formulation co-generated with a hydrogen peroxide solution. More specifically, the superoxide to hydrogen peroxide solutions are generated such that the ratio of superoxide to hydrogen peroxide is 0.01:1 to 10:1. More specifically, the superoxide to hydrogen peroxide solutions are generated such that the ratio of superoxide to hydrogen peroxide ranges from 0.01:1 to 0.5:1, from 0.5:1 to 1.5:1, from 1.5:1 to 3:1, from 3:1 to 5:1, or from 5:1 to 10:1. In an embodiment, the electrochemically generated, reactive oxygen species solution has initial pH of 8-13, or 8-9, or 9-12, or 12-13.

In an embodiment, the invention provides a formulation containing an electrochemically generated hydroperoxyl radical. In an embodiment, the radical is created by the reaction of electrochemically generated superoxide formulation co-generated with hydrogen peroxide formulation by the reaction:

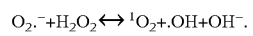

$O_2^- + H_2O_2 \leftrightarrow {}^1O_2 + .OH + OH^-$.

In an embodiment, the invention provides a method for treating waste water employing formulations of the invention containing reactive oxygen species. In a specific embodiment, the method includes electrochemically co-generating a cathode output solution comprising superoxide and hydrogen peroxide; mixing the cathode output solution into a waste water source; and adjusting the pH of the mixture. In an embodiment, pH is adjusted after the step of mixing the cathode output solution into the waste water source.

Other embodiments of the invention will become apparent on review of the following drawings and detailed description.

DETAILED DESCRIPTION OF THE INVENTION

Reactive Oxygen Species from Bulk Chemicals:

In the following embodiments, systems and methods are shown to generate reactive oxygen species in situ from a mixture of bulk chemical feedstocks in close proximity to various substrates defined as materials, compounds, atoms or ions (organic or inorganic) to be oxidized or microorganisms to be denatured or killed.

In the following embodiments, exemplary systems and methods are shown, for example, that describe alternatives to the use of hydroxyl radical oxidation chemistry that are more compatible with saline or highly contaminated waters and minimizes chlorate and bromate formation by having lower standard oxidation potentials than chloride, bromide or their hypohalite forms while possessing high chemical reactivity toward a variety of substrates.

In another embodiment, an exemplary system and method is shown for enabling the production of larger quantities and higher concentrations of singlet oxygen from chemical precursor formulations not containing singlet oxygen quenching agents.

In yet another embodiment, an exemplary method and system is shown for singlet oxygen production to occur for extended periods of time while the amount and rate of singlet oxygen evolved can be controlled by the more readily measurable precursor formulation and concentration.

Figure 1:
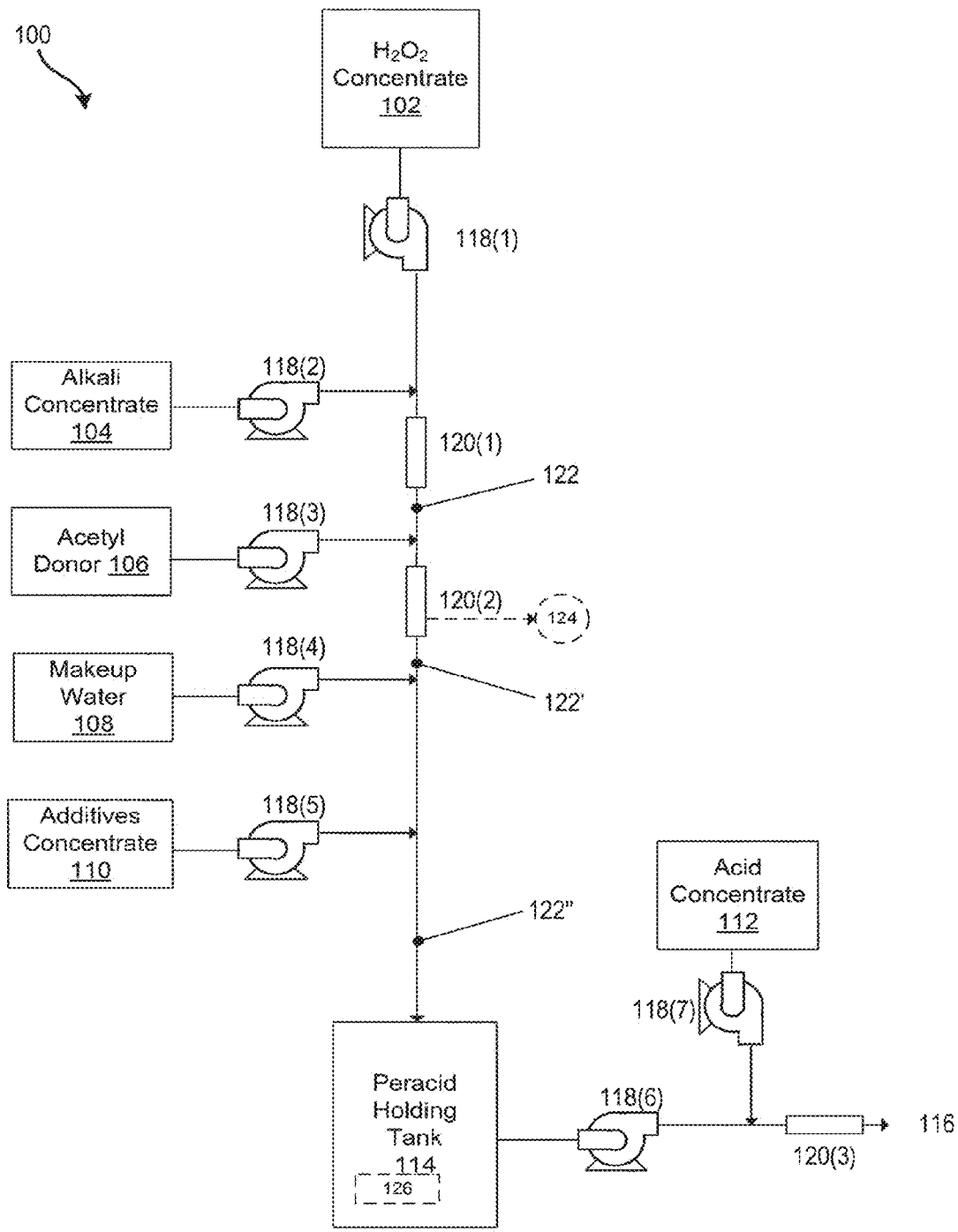
FIG. 1 shows one exemplary system 100 for generation of a diluted reactive oxygen species 116 using bulk chemical feedstock constituents, in an embodiment.

FIG. 1 shows one exemplary system 100 for generation of a diluted reactive oxygen species 116 using bulk chemical feedstock constituents, in an embodiment. In an embodiment, diluted reactive oxygen species output 116 is used in applications where a fluid is conveyed to a surface or material including clean in place, hard surface cleaning, decontamination, remediation and in situ chemical oxidation applications. System 100 includes hydrogen peroxide ($H_2O_2$) concentrate 102, alkali concentrate 104, acyl or acetyl donor 106, makeup water 108, additives concentrate 110, acid concentrate 112, peracid holding tank 114, reactive oxygen species output 116, pumps 118, and mixing chambers 120. In one embodiment, reactive oxygen species output 116 is diluted singlet oxygen precursor solution.

Hydrogen Peroxide Concentrate 102 is typically an aqueous hydrogen peroxide solution, for example. However, in alternative embodiments, hydrogen peroxide concentrate 102 may include other chemical forms of peroxide chosen from the group including: calcium peroxide, potassium peroxide, sodium peroxide, lithium peroxide, percarbonates, and perborates.

In one embodiment, alkali concentrate 104 is an aqueous sodium hydroxide solution. In an alternative embodiment, Alkali concentrate 104 is potassium hydroxide. Acyl or acetyl donor 106 or mixture of donors may be in liquid or solid form, or dissolved in a solvent when reacted with a solution of hydrogen peroxide.

Acid concentrate 112, for example, includes at least one pH buffer chosen from the group including: weak acid electrolytes including acetate, citrate, propionate, phosphate and sulfate.

In an embodiment, reactive oxygen species output 116 is a peroxyacetic acid in the absence of hydrogen peroxide and includes at least one chemical precursor species capable of releasing singlet oxygen. In alternative embodiments, reactive oxygen species output 116 includes two chemical precursor species may be used to release singlet oxygen. In yet another embodiment, reactive oxygen species output 116 includes more than two chemical precursor species to release singlet oxygen.

Figure 2:
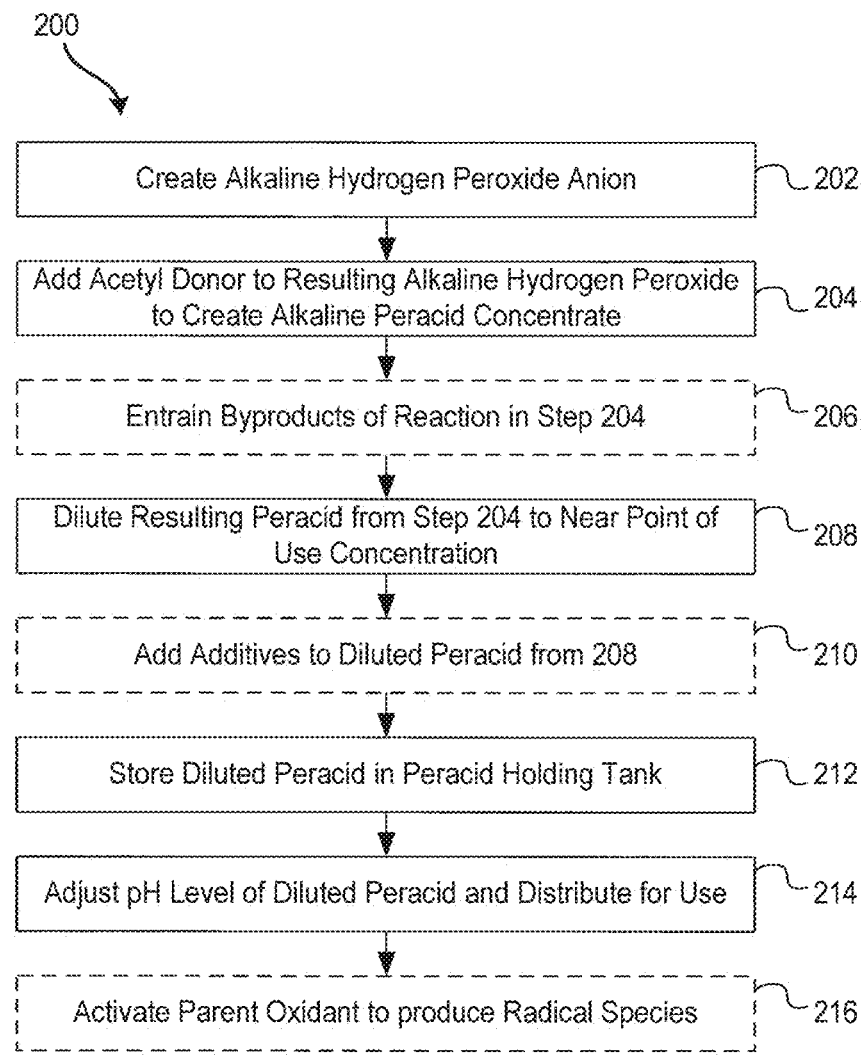
FIG. 2 shows an exemplary method 200 for generating reactive oxygen species output 116 using system 100 of FIG. 1.

FIG. 2 shows an exemplary method 200 for generating reactive oxygen species output 116 using system 100 of FIG. 1. In an embodiment, the reactive oxygen species output 116 generated by method 200 is singlet oxygen. In step 202, an alkaline hydrogen peroxide anion solution 122 is created by mixing $H_2O_2$ concentrate 102 with alkali concentrate 104 in mixing tank 120(1). For example, molar ratios of $H_2O_2$ concentrate 102 to alkali in alkali concentrate 104 may range from 1:1.2 to 1:2.5. In an embodiment, the preferred molar ratio range is 1:1.4 to 1:2, for example. The preferred molar ratio range is determined by the preferred pH range of the alkaline hydrogen peroxide solution of pH 12.0 to 12.6, which promotes the reaction between hydrogen peroxide and the acyl or acetyl donor. In one embodiment, hydrogen peroxide concentrate 102 is a weak acid with a pKa of 11.6 and therefore its combination with alkali converts it in an acid-base equilibrium to the hydrogen peroxide anion form as in Equation 1 below:

$$HOOH + OH^- \leftrightarrow HOO^- + H_2O \quad [1]$$

In some embodiments, raising the pH of a hydrogen peroxide solution enough to put a significant proportion of hydrogen peroxide into the anion form requires an excess of alkali 104 over hydrogen peroxide 102. In one embodiment, the molar excess of alkali 104 over $H_2O_2$ 102 may range from 20% to 100% greater alkali 104. For example, a preferred molar excess range is 20% to 40% greater alkali 104. The equilibrium reaction in Equation 1 consumes alkali in a 1:1 molar ratio, therefore an excess of alkali over hydrogen peroxide is required to raise the pH of the alkaline hydrogen peroxide solution to the preferred pH range.

In step 204, the resulting alkaline hydrogen peroxide 122 is combined with an acyl or acetyl donor 106 in mixing tank 120(2) to create a resulting alkaline peracid concentrate 122'. In one embodiment, alkaline peracid concentrate 122' may be a peroxyacetic acid solution. In one embodiment, the acyl or acetyl donor is added in proportion to the hydrogen peroxide. In an alternative embodiment, the molar ratio of $H_2O_2$ 122 to acyl or acetyl donor 106 reactive group equivalents can range from 1:1.25 to 1:4. For example, a preferred molar ratio range is 1:1.5 to 1:2. If the ratio is too low a high hydrogen peroxide residual will remain in the peracid concentrate where it will significantly quench singlet oxygen. If the ratio is higher than needed to achieve a low hydrogen peroxide residual that does not significantly quench singlet oxygen then excess acyl or acetyl donor is remains unused. In one embodiment, the acyl or acetyl donor is an oxygen-acyl or oxygen-acetyl donor shown in Equation 2a below:

$$HOO^- + AcOR \rightarrow AcOO^- + ROH \quad [2a]$$

Where Ac is acyl [—C(O)R'] or acetyl [—C(O)CH$_3$] and R and R' are hydrocarbon-based substituents. In an alternative embodiment, the acyl or acetyl donor is a nitrogen-acyl or nitrogen-acetyl donor as shown in Equation 2b below:

$$HOO^- + AcNR_2 \rightarrow AcOO^- + RNH \quad [2b]$$

Where Ac is acyl [—C(O)R'] or acetyl [—C(O)CH$_3$] and R and R' are hydrocarbon-based substituents.

In Equations 2a/2b above, the reaction between an acyl or acetyl donor 106 and hydrogen peroxide 122 occurs at alkaline pH by nucleophilic attack of the acyl carbonyl carbon atom by the hydrogen peroxide anion, which displaces the donor molecule fragment as an alcohol or amine in a manner analogous to saponification. In some embodiments, the non-equilibrium reactions generalized in Equations 2a/2b are conducted between pH 10 and pH 13.

The use of non-equilibrium reaction in Equations 2a/2b produces alkaline peracid concentrate 122' with concentrations of less than approximately 5 wt % peroxyacetic acid and other organic peracids that are produced efficiently and rapidly. Using the non-equilibrium reaction allows the hydrogen peroxide residual to be minimized if necessary. Minimizing the hydrogen peroxide residual, for example, significantly increases the concentration of the singlet oxygen available to oxidize target substrates. In one embodiment, for example, the [peroxyacetic acid][water]/[hydrogen peroxide] concentration ratios are from 10, 100, or 1000 depending on the ratio of hydrogen peroxide to acyl or acetyl donor ratio in Equations 2a/2b.

In one embodiment, at least one molar equivalent of acyl or acetyl donor 106 reactive groups is added for each equivalent of hydrogen peroxide in alkaline hydrogen peroxide anion solution 122 used in Equations 2a/2b to consume all of the hydrogen peroxide. In alternative embodiments, excess acyl or acetyl donor 106 reactive groups is necessary to minimize the hydrogen peroxide residual due to the competing conversion of acyl or acetyl donor 106 reactive groups to the corresponding carboxylic acid by the alkali concentrate 104 used to raise the pH of the $H_2O_2$ concentrate 102. In one embodiment, the molar excess of acyl or acetyl donor 106 reactive groups over $H_2O_2$ solution 122 may range from 25% to 300% greater acyl or acetyl donor 106. For example, a preferred molar excess range is 50% to 100% greater acyl or acetyl donor 106 reactive groups.

In optional step 206, as indicated by the dashed lines, method 200 entrains byproducts 124 produced by the reactions of Equations 2a/2b. For example, byproducts 124 are entrained in solution with the alkaline peracid concentrate 204. In one embodiment, byproducts 124 are useful as co-solvents, pH buffers, chelating agents or stabilizers and carbon substrates for microbial processes after a chemical oxidation process. For example, the byproduct 124 of acetyl donors 106 of monacetin, diacetin and triacetin is glycerol, a potential co-solvent and favorable carbon source for microbes. In another embodiment, byproduct 124 of acetyl donor 106 of TAED, diacetylethylenediamine, acts as a chelating agent for transition metal ions and potentially serves as a peroxide stabilizer. In yet another embodiment, byproduct 124 is the carboxylic acid produced after alkaline peracid concentrate 122' reacts with a material or decomposes. Alternatively, acetic acid, a byproduct 124 of peroxyacetic acid, serves as a co-solvent, a pH buffer, a chelating agent, and a biological substrate.

In step 208, method 200 dilutes the resulting alkaline peracid concentrate 122' to nearly point of use concentration by adding makeup water 108. The amount of dilution is dependent on the concentration of alkaline peracid concentrate 122' and the desired point of use concentration of reactive oxygen species output 116. For example the alkaline peracid concentration 122' may be 19 wt % to 21 wt % using 50 wt % hydrogen peroxide concentrate 102, 50 wt % sodium hydroxide as the alkali concentrate 104 and triacetin as the acetyl donor 106. In another example the alkaline peroxyacetic acid concentration can be 17 wt % to 19 wt % using 30 wt % hydrogen peroxide concentrate 102, 50 wt % sodium hydroxide as the alkali concentrate 104 and triacetin as the acetyl donor 106.

In step 212, method 200 then stores the resulting combination in peracid holding tank 114. In optional step 210, as indicated by a dashed outline, method 200 adds additives concentrate 110 to the resulting diluted peracid from step 208, and then stores the combination in peracid holding tank 114 in step 212. In one embodiment, the alkaline peracid stored in peracid holding tank 114 contains all constituents for formulation of reactive oxygen species output 116 except for the final activating pH adjustment. This allows for the diluted alkaline peracid 122" to have a modest lifetime prior to use and be stored in peracid holding tank 114 for several minutes to a few hours, depending on the concentration determined in step 208, and any additives added in step 210. In an alternative embodiment, optional step 210 may be performed by adding an additive concentration 110 of peroxide stabilizer before, during, or after combination of the acyl or acetyl donor 106 in step 204.

In step 214, method 200 adjusts the diluted peracid's 122" pH to the activated pH level for producing reactive oxygen species output 116 by adding acid concentrate 112 and mixing in mixing chamber 120(3). The resulting reactive oxygen species output 116 is then distributed to its point of use in liquid form. The reactive oxygen species output 116 may then be used in the form of a liquid, an ice, a foam, an emulsion, a micro-emulsion or an aerosol applied by means such as injection, flooding, spraying, circulation or any other means of conveying a fluid. In one embodiment, the diluted peracid's 122" pH does not require the addition of acid concentrate 112 and is ready for immediate distribution 214 to its point of use.

In one embodiment, during step 214, an acid concentration 112 is combined with diluted peracid 122" such that there is a population of both peracetic acid and peracetic acid anion which react together to generate singlet oxygen according to Equation 3 below:

$$AcOOH + AcOO^- \rightarrow {}^1O_2 + AcOH + AcO^- \quad [3]$$

Wherein the reaction rate for Equation 3 above follows a second order kinetics and is maximized when the ratio of the two forms of peroxyacetic acid is equivalent at its pKa of 8.3. The evolution and release of singlet oxygen occurs over time ranging from minutes to several hours depending on the rate of reaction in Equation 3 above. In one embodiment, the evolution of singlet oxygen from peroxyacetic acid, or other organic peracid having a similar pKa, the pH is between 6.5 and 9.5. In another embodiment the evolution of singlet oxygen from peroxyacetic acid, or other organic peracid having a similar pKa, may be substantially retarded between about pH 9.5 and 12.5. For example, as pH becomes more alkaline the peracetic acid anion dominates the composition leaving very little peracetic acid to react with by the reaction in Equation 3. Retardation of singlet oxygen production extends the lifetime of the peroxyacetic acid or peracid solution and also allows for singlet oxygen use at elevated pH relevant to certain applications which use alkaline oxidants or cleansers up to pH 12 to 12.5.

In optional step 216, as shown by the dashed outline, method 200 further activates the reactive oxygen species output 116 by means of a Fenton or Fenton-like catalyst, ultrasound, ultraviolet radiation or thermal activation (not shown in FIG. 1) to produce radical species such as hydroxyl radicals.

Figure 3:
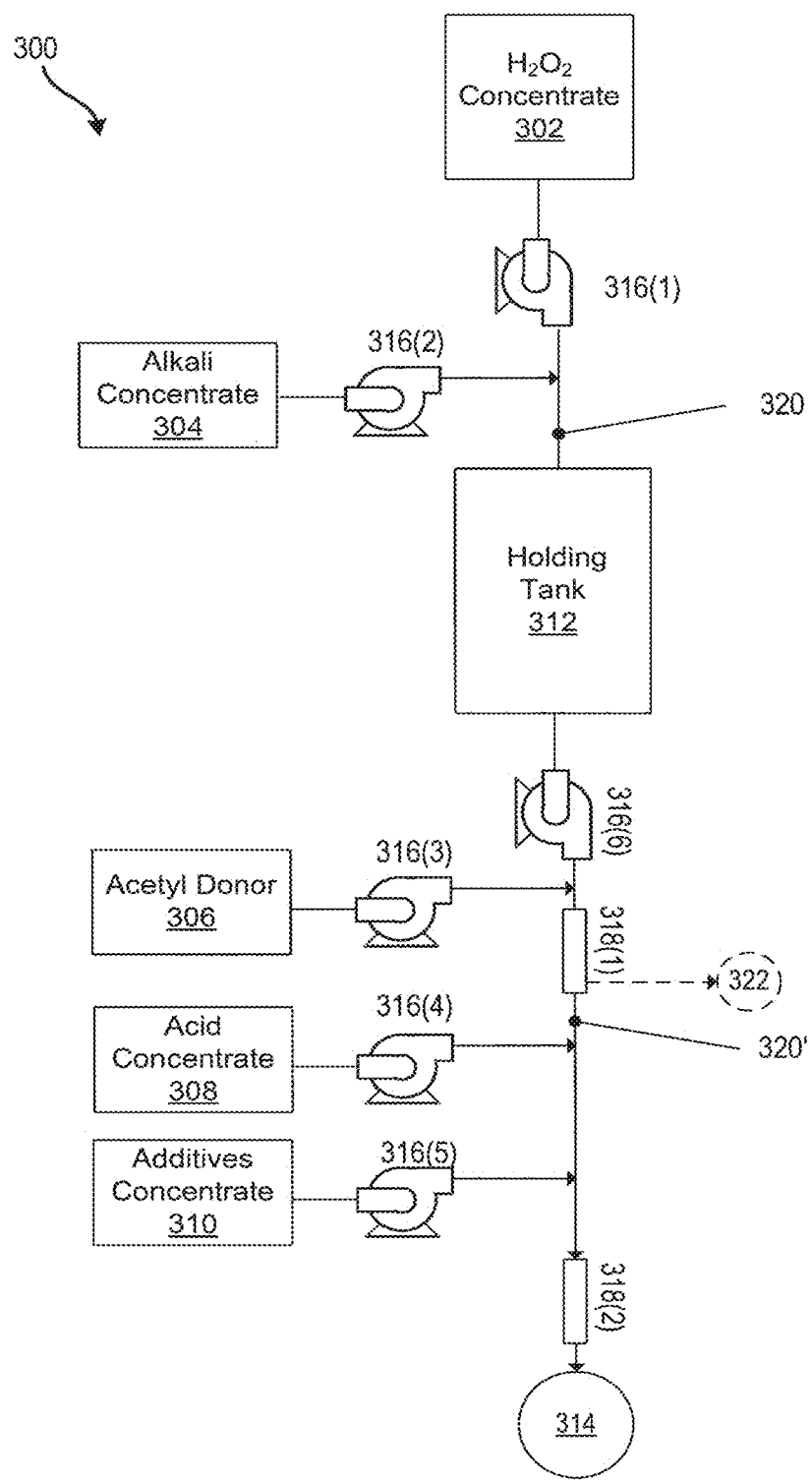
FIG. 3 shows one exemplary system 300 for generation of a concentrated reactive oxygen species output 314 using bulk chemical precursor constituents, in one embodiment.

FIG. 3 shows one exemplary system 300 for generation of a concentrated reactive oxygen species output 314 using bulk chemical precursor constituents, in one embodiment. In one embodiment, concentrated reactive oxygen species output 314 is used in applications where a concentrate is dosed into a liquid stream, including, but not limited to water and wastewater treatment; cooling tower water treatment and cooling tower system cleaning; desulfurization and deodorization of gases; water treatment in forestry operations, pulp and paper making processes; oil and gas produced water and hydraulic fracturing flowback water treatment. System 300 includes hydrogen peroxide ($H_2O_2$) concentrate 302, alkali concentrate 304, acyl or acetyl donor 306, acid concentrate 308, additives concentrate 310, alkaline hydrogen peroxide holding tank 312, reactive oxygen species output 314, pumps 316 and mixing chambers 318. In one embodiment, reactive oxygen species output 316 is concentrated singlet oxygen precursor solution.

In one embodiment, alkali concentrate 304 is an aqueous sodium hydroxide solution. In another embodiment, alkali concentrate is an aqueous potassium hydroxide solution. Acyl or acetyl donor 306 or mixture of donors may be in liquid or solid form, or dissolved in a solvent when reacted with a solution of hydrogen peroxide.

Acid concentrate 308, for example, includes at least one pH buffer chosen from the group including: weak acid electrolytes including acetate, citrate, propionate, phosphate and sulfate. Additives concentrate 310, for example, includes at least one of the following additives chosen from the group including: salts, surfactants, co-solvents, stabilizers, and emulsifiers.

In an embodiment, reactive oxygen species output 314 is a peroxyacetic acid in the absence of hydrogen peroxide and includes at least one chemical precursor species capable of releasing singlet oxygen. In alternative embodiments, reactive oxygen species output 316 includes two chemical precursor species may be used to release singlet oxygen. In yet another embodiment, reactive oxygen species output 316 includes more than two chemical precursor species to release singlet oxygen.

Figure 4:
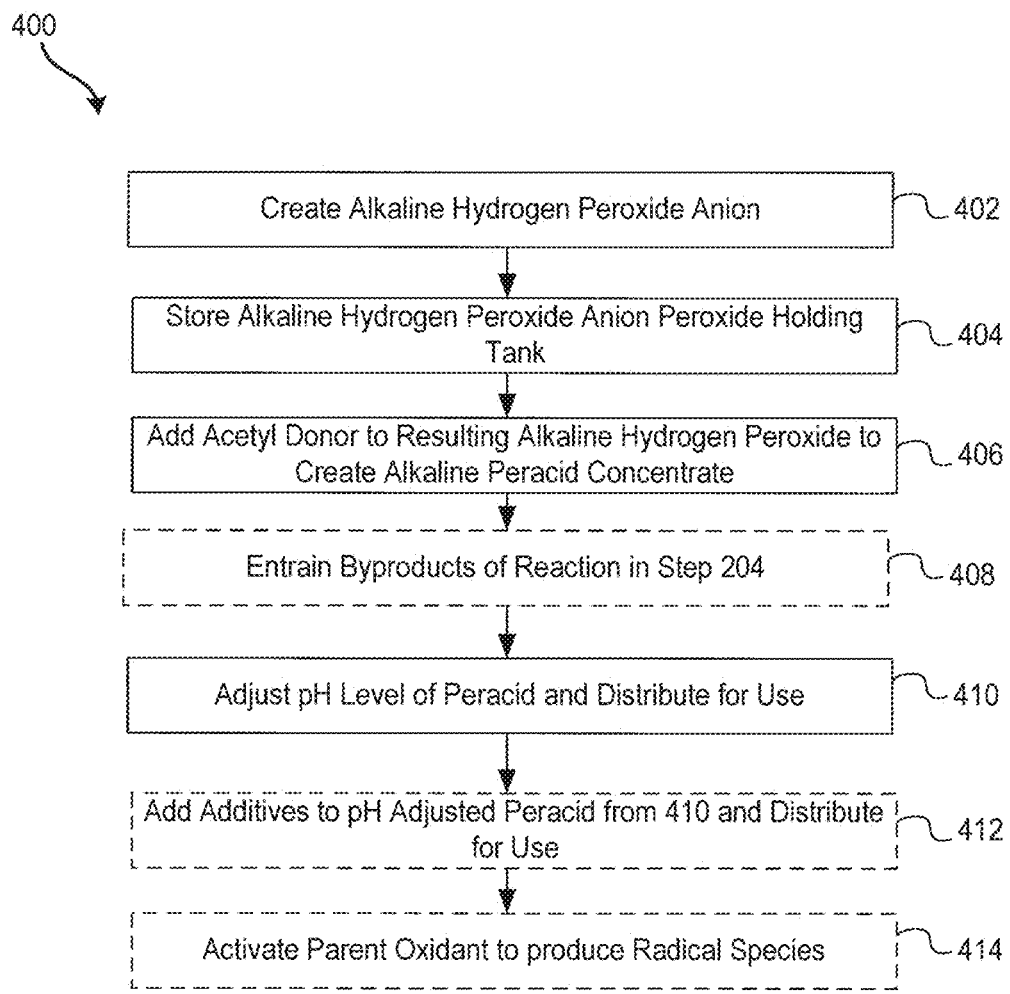
FIG. 4 shows an exemplary method 400 for generating reactive oxygen species output 314 using system 300 of FIG. 3.

FIG. 4 shows an exemplary method 400 for generating reactive oxygen species output 314 using system 300 of FIG. 3. In an embodiment, reactive oxygen species output 316 generated by method 400 is concentrated singlet oxygen precursor solution. In step 402, an alkaline hydrogen peroxide anion solution 320 is created by mixing $H_2O_2$ concentrate 302 with alkali concentrate 304. For example, molar ratios of $H_2O_2$ concentrate 302 to alkali 304 may range from 1:1.2 to 1:2.5. In one embodiment, a preferred molar ratio range is 1:1.4 to 1:2. In one embodiment, hydrogen peroxide is a weak acid with a pKa of 11.6 and therefore its combination with alkali converts it in an acid-base equilibrium to the hydrogen peroxide anion form as in Equation 1 above. In some embodiments, raising the pH of a hydrogen peroxide solution enough to put a significant proportion of hydrogen peroxide into the anion form requires an excess of alkali over hydrogen peroxide. For example, the molar excess of alkali 304 over $H_2O_2$ concentrate 302 may range from 20% to 100% greater alkali 304. In one embodiment, a preferred molar excess range is 20% to 40% greater alkali 304.

In step 404, the resulting alkaline hydrogen peroxide 320 is stored in alkaline hydrogen peroxide holding tank 312 for immediate or later use. Alkaline hydrogen peroxide 320 has a longer lifetime prior to use which allows the alkaline hydrogen peroxide 320 to be stored for several minutes to a few hours in alkaline hydrogen peroxide holding tank 312 without as much decomposition as a peracid at a similar concentration.

In step 406, the alkaline hydrogen peroxide 320 is combined with an acyl or acetyl donor 306 in mixing tank 318(1) to create a resulting alkaline peracid concentrate 320'. In one embodiment, the acyl or acetyl donor 30 is added in proportion to the alkaline hydrogen peroxide 320. In one embodiment, the molar ratio of $H_2O_2$ 320 to acyl or acetyl donor 304 reactive groups may range from 1:1.25 to 1:4. For example, a preferred molar ratio range is 1:1.5 to 1:2. In one embodiment, the acyl or acetyl donor is an oxygen-acyl or oxygen-acetyl donor shown in Equation 2a above, where Ac is acyl [—C(O)R] or acetyl [—C(O)CH$_3$] and R and R' are hydrocarbon-based substituents. In an alternative embodiment, the acyl or acetyl donor is a nitrogen-acyl or nitrogen-acetyl donor as shown in Equation 2b above, where Ac is acyl [—C(O)R] or acetyl [—C(O)CH$_3$] and R and R' are hydrocarbon-based substituents.

In Equations 2a/2b above, the reaction between an acyl or acetyl donor 306 and alkaline hydrogen peroxide 320 occurs at alkaline pH by nucleophilic attack of the acyl carbonyl carbon atom by the hydrogen peroxide anion, which displaces the donor molecule fragment as an alcohol or amine in a manner analogous to saponification. In some embodiments, the non-equilibrium reactions generalized in Equations 2a/2b are conducted between pH 10 and pH 13.

The use of non-equilibrium reaction in Equations 2a/2b provides, for example, alkaline peracid concentrates 320' with concentrations of less than approximately 5 wt % peroxyacetic acid and other organic peracids are produced efficiently and rapidly. Using the non-equilibrium reaction allows the hydrogen peroxide residual to be minimized if necessary. In one embodiment, for example, the peroxyacetic acid water/peroxide concentration ratios can be 10, 100, or 1000 depending on the ratio of hydrogen peroxide to acyl or acetyl donor ratio in Equations 2a/2b.

In one embodiment, at least one molar equivalent of acyl or acetyl donor 106 is added for each equivalent of hydrogen peroxide in alkaline hydrogen peroxide anion 320 used in Equations 2a/2b to consume all of the hydrogen peroxide. In alternative embodiments, excess acyl or acetyl donor 306 reactive groups is necessary to minimize the hydrogen peroxide residual due to the competing conversion of acyl or acetyl donor 306 reactive groups to the corresponding carboxylic acid by the alkali concentrate 304 used to raise the pH of the $H_2O_2$ concentrate 302.

In optional step 408, as indicated by the dashed lines, method 400 entrains byproducts 320 produced by the reactions of Equations 2a/2b occurring in step 406. For example, byproducts 322 are entrained in solution with the alkaline peracid concentrate 320'. In one embodiment, byproducts 322 are useful as co-solvents, pH buffers, chelating agents or stabilizers and carbon substrates for microbial processes after a chemical oxidation process. For example, the byproduct 322 of acetyl donors 306 of monacetin, diacetin and triacetin is glycerol, a potential co-solvent and favorable carbon source for microbes. In another embodiment, byproduct 322 of acetyl donor 106 of TAED, diacetylethylenediamine, acts as a chelating agent for transition metal ions and potentially serves as a peroxide stabilizer. In yet another embodiment, byproduct 322 is the carboxylic acid produced after an alkaline peracid concentrate 320' reacts with a material or decomposes. Alternatively, acetic acid, a byproduct 322 of peroxyacetic acid, serves as a co-solvent, a pH buffer, a chelating agent, and a biological substrate.

In step 410, method 400 adjusts the alkaline peracid concentrate 320' pH to the activated pH level for producing reactive oxygen species output 314 by adding acid concentrate 308 and mixing in mixing chamber 318(2). The resulting reactive oxygen species output 314 is then distributed to its point of use in liquid form. The reactive oxygen species output 314 may then be used in the form of a liquid, an ice, a foam, an emulsion, a micro-emulsion or an aerosol applied by means such as injection, flooding, spraying, circulation or any other means of conveying a fluid. In one embodiment, the alkaline peracid concentrate 320' pH does not require the addition of acid concentrate 308 and is ready for immediate distribution 410 to its point of use.

In one embodiment, during step 410, an acid concentration 308 is combined with alkaline peracid concentrate 320' such that there is a population of both peracetic aid and peracetic acid anion which react together to generate singlet oxygen according to Equation 3 above, wherein the reaction rate for Equation 3 above follows a second order kinetics and is maximized when the ratio of the two forms of peroxyacetic acid is equivalent at its pKa of 8.3. The evolution and release of singlet oxygen occurs over time ranging from minutes to several hours depending on the rate of reaction in Equation 3 above. In one embodiment, the evolution of singlet oxygen from peroxyacetic acid, or other organic peracid having a similar pKa, the pH is between 6.5 and 9.5.

In optional step 412, as indicated by a dashed outline, method 400 adds additives concentrate 310 to the resulting peracid from step 410, and then distributes the resulting solution for use.

In optional step 414, as shown by the dashed outline, method 400 further activates the reactive oxygen species output 314 by means of a Fenton or Fenton-like catalyst, ultrasound, ultraviolet radiation or thermal activation (not shown in FIG. 3) to produce radical species such as hydroxyl radicals.

Generation of Reactive Oxygen Species Using Electrochemical Generator

In the following embodiments, reactive oxygen species are generated by creating the necessary constituents and their mixing through the generation of all or a portion of these materials on site in a manner that minimizes the number of bulk chemical feedstocks and eliminates hazardous bulk chemical feedstocks. For example, the required components of hydrogen peroxide, alkali, and acid may be co-generated electrochemically from simple feedstocks including water, oxygen gas, and a salt or brine.

In the following embodiments, alternative methods are shown, for example, for delivering reactive oxygen compositions which can also generate hydroxyl radicals in cases where chlorate and bromate formation is not a primary issue.

Figure 5:
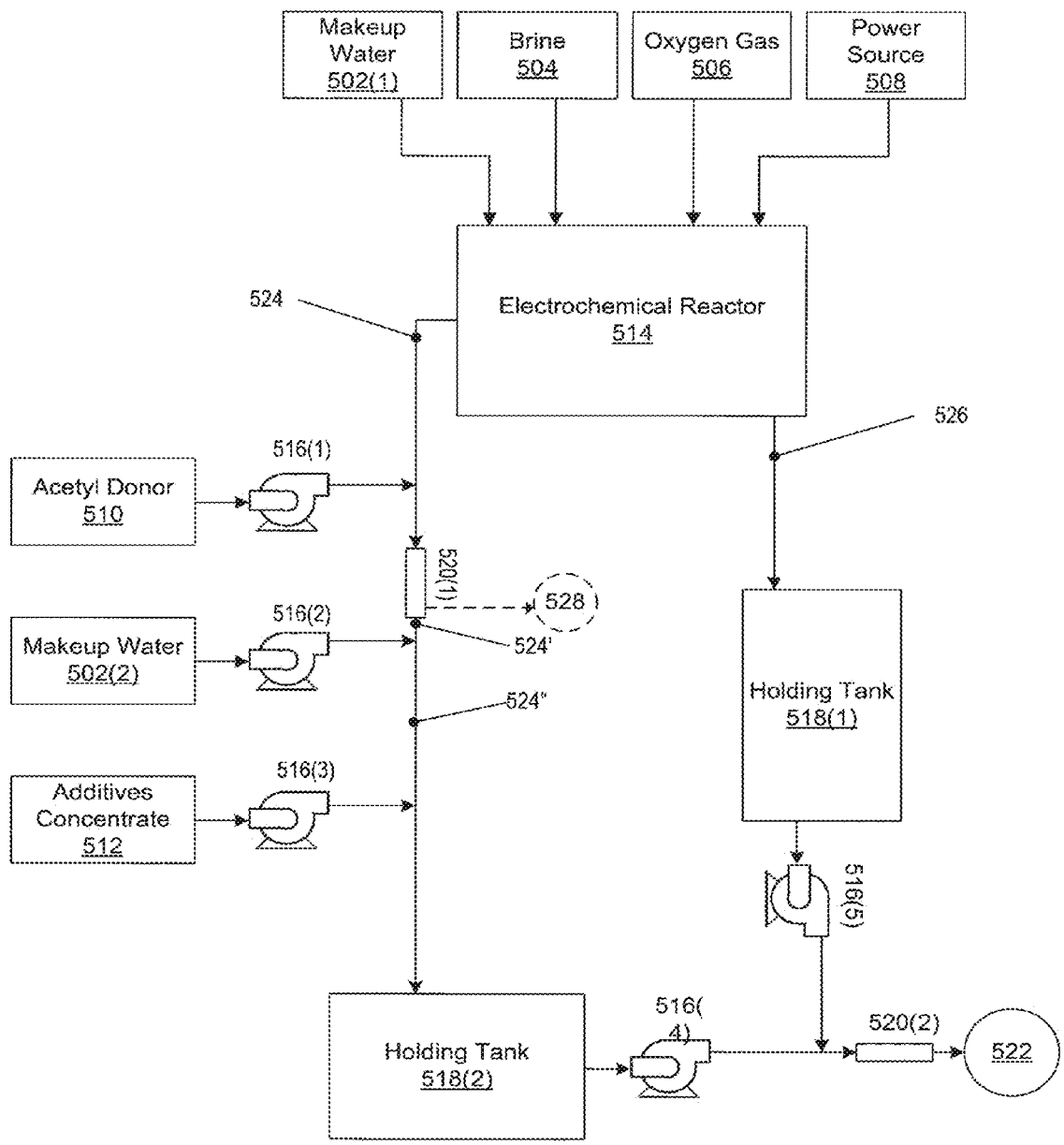
FIG. 5 shows an exemplary system 500 for generating chemicals using an electrochemical reactor 514 to produce a diluted reactive oxygen species output.

FIG. 5 shows an exemplary system 500 for generating chemicals using an electrochemical reactor 514 and mixing the reactor's 514 outputs together and optionally with other materials to produce a diluted reactive oxygen species output 522. In one embodiment, diluted reactive oxygen species output 520 is used, but not limited to, in applications where a fluid is conveyed to a surface or material as the primary reactive oxygen species in addition to the parent oxidants at the point of use or in situ. In some embodiments, applications include, but are not limited to, in situ chemical oxidation for remediation of soil and groundwater; ex-situ chemical oxidation for remediation of soil, construction or demolition debris; hard surface cleaning and decontamination, clean-in place applications in food, dairy, beverage and biopharma production and processing; cleaning of membrane filtration systems; and flushing of well casings and water distribution pipes.

System 500 includes an electrochemical reactor 514 including inputs of a makeup water 502(1), brine 504, oxygen gas 506, and power source 508, an acyl or acetyl donor 510, an additives concentrate 512, pumps 516, holding tanks 518, mixing chambers 520, and reactive oxygen species output 522. In one embodiment, the electrochemical reactor 514 is that embodied by PCT Application No. PCT/US2012/040325 titled "Electrochemical Reactor and Process." This published PCT application is incorporated by reference herein in its entirety for its description of electrochemical reactors and processes. More specifically, the reference includes description for reactor device configurations including cathodes and anodes which are useful in embodiments of this invention. The reference also includes descriptions of reactors useful for preparation of oxidants including hydrogen peroxide, superoxide, sodium hypochlorite, hypochlorites among others and for generation of alkali, and acids. Details of reactor cathodes and anodes and process for production of oxidants are also incorporated by reference herein. An exemplary electrochemical reactor is shown in FIG. 6.

Exemplary Electrochemical Reactor

Figure 6A:
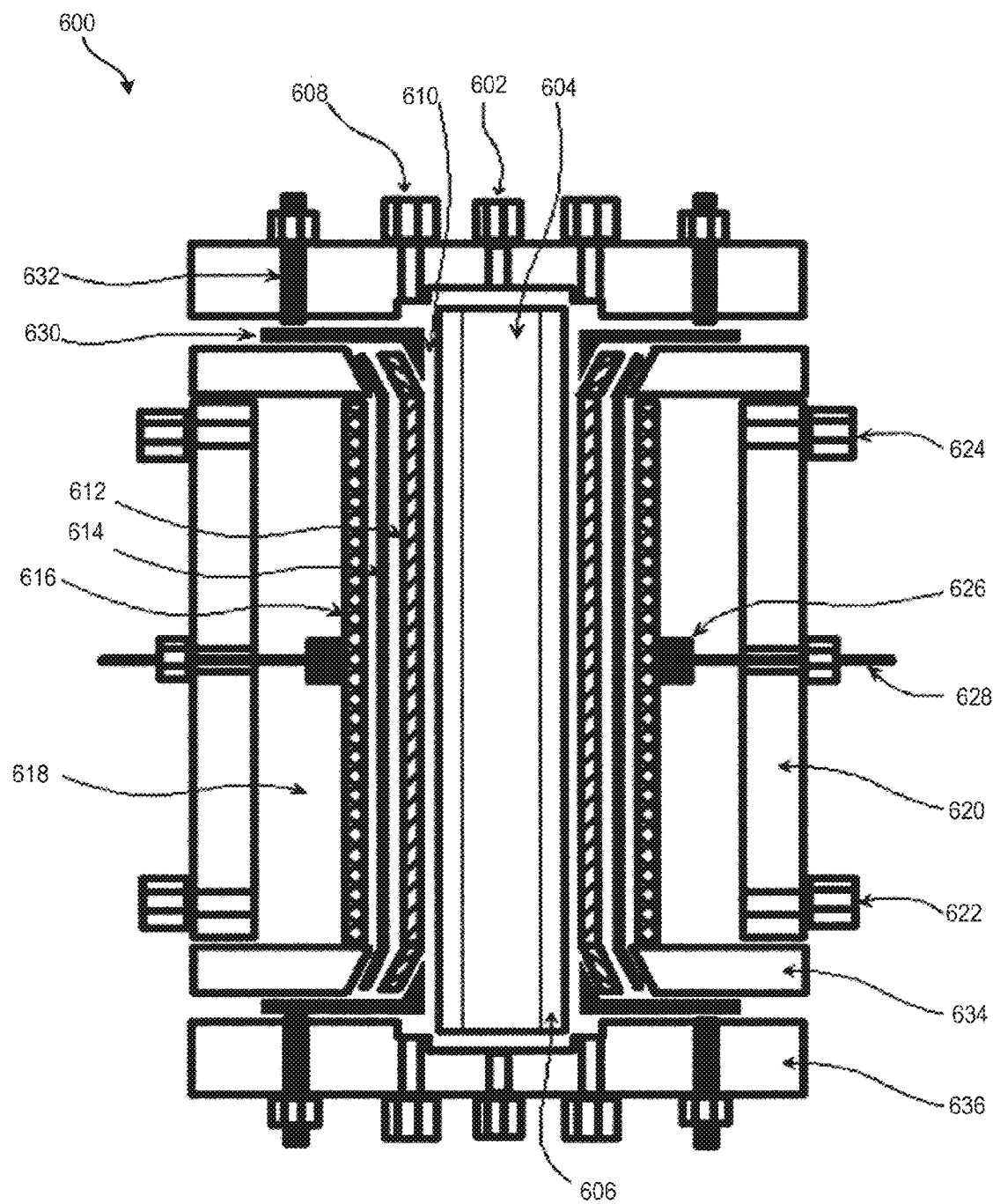
FIGS. 6A/6B depict an exemplary a cross-sectional view of the general configuration and components of an exemplary electrochemical reactor 600 for use in system 500 of FIG. 5, in one embodiment.

FIGS. 6A/6B depict an exemplary a cross-sectional view of the general configuration and components of an exemplary electrochemical reactor 600 for use in system 500 of FIG. 5, in one embodiment. In one embodiment, electrochemical reactor 600 has a general tubular or annular configuration. The housing for electrochemical reactor 600 has three distinct parts an anode housing 620, a seat plate 634, and an end plate 636, each of which may be fabricated in quantity from structural thermoplastics (pure and filled) including, but not limited to, polyvinyl chloride (PVC), chlorinated polyvinylchloride (CPVC), polyvinylidine difluoride (PVDF), polyethylene, polytetrafluoroethylene (PTFE), ethylene tetrafluoroethyelene (ETFE), acrylonitrile butadiene styrene (ABS) polymer blends, etc.

In an embodiment, anode housing 620 is an extruded tube, such as a standard schedule 80 pipe that is modified with tube fittings, feed-throughs, O-ring, or gasket sealing surfaces and threaded bolt holes. In an embodiment, anode housing 620 contains the anolyte solution within electrochemical reactor 600. In an embodiment, anode housing 620 contains the anolyte solution within an anolyte chamber 618. In an embodiment, anode housing 620 provides structural integrity to electrochemical reactor 600 and is what seat plate 634 and end plate 636 are fastened to, thereby holding electrochemical reactor 600 and its contents together as a single unit. In some embodiments, anode housing 620 is made from PVC.

In an embodiment, seat plate 634 contains a central opening with a tapered surface on which a separator 614 is sealed. A cathode 612 extends through seat plate 634. A cathode current distributor and compression ferrule 630 contacts cathode 612 and anchors it in place while simultaneously compressing separator 614 to make a gas-tight seal between a cathode flow channel 610 and the anolyte chamber 618. Seat plate 634 also has gasket or O-ring sealing surfaces for making gas-tight seals with anode housing 620 and with cathode current distributor and compression ferrule assembly 630.

In an embodiment, cathode current distributor and compression ferrule 630 may be constructed of a rigid material that is conductive and non-corrosive such as stainless steel alloys, high nickel alloys, and high purity titanium, for example. In an embodiment, cathode current distributor and compression ferrule 630 is 316 stainless steel. In yet another embodiment, the surfaces of current distributor and compression ferrule 630 facing into cathode flow channel 610 and manifold are masked with a non-conductive material such as a thermoplastic, a polymer coating, or an elastomeric adhesive coating.

In an embodiment, end plate 636 provides a gas inlet 602 and catholyte fluid distribution manifolds which are accessed through the catholyte inlet or outlet 608. In an embodiment end plate 636 seals against the end of a gas distributor tube 606 creating a separate gas chamber 604 down the center axis of electrochemical reactor 600. End plate 636 contains gasket and O-ring sealing surfaces for making gas-tight seals with gas distributor tube 606 and cathode current distributor and compression ferrule assembly 630. In an embodiment, end plate 636 provides the compressive force to seal separator 614 to seat plate 634, seal seat plate 634 to anode housing 620, seal the faces of the cathode current distributor and compression ferrule assembly 630 to end plate 636 and seat plate 634, seal gas distributor tube 606 and fasten electrochemical reactor 600 together.

In an embodiment, end plate 636 holds the cathode electrical feed-through posts 632, which contact cathode current distributor and compression ferrule 630 and are connected by means of conductors to the negative pole (direct current, DC) or ground (alternating current, AC) of a power supply. In one embodiment, electrical feed-through posts 632 are made from a material that is conductive and non-corrosive such as stainless steel alloys, high nickel alloys, and high purity titanium, for example. In an embodiment, cathode electrical feed-through posts 632 are 18-8 stainless steel.

In one embodiment, gas distribution tube 606 is a porous or microporous material that allows gas to permeate through its wall and resists water permeation. In an embodiment, gas distribution tube 606 is a non-conductive, hydrophobic material such as polyethylene, polypropylene, polytetrafluoroethylene, or polyvinylidene difluoride, for example. In an embodiment, gas distribution tube 606 may be a microporous ceramic such as alumina, zirconia, titania or other suitable material with a hydrophobic coating. Gas distribution tube 606 may be made by casting-sintering or extrusion production methods, for example. In an embodiment, gas distribution tube 606 contains pores having a diameter rating that is less than about 10 microns. In an embodiment, gas distribution tube 206 contains pores having a diameter rating that is less than about or equal to 5 microns. The pores of gas distribution tube 606 may be masked in part to bias the gas permeation through regions of gas distribution tube 606 for purposes including making the ends gas and liquid impermeable in the catholyte manifold and current collector regions, compensating for pressure gradients, gas loading in the catholyte, and/or modulating residence time in the cathode flow chamber.

In an embodiment, cathode flow channel 610 is defined by gas distribution tube 606 and separator 614. Cathode 612 resides within cathode flow channel 610 immersed in the catholyte liquid while gas is supplied from the back side of cathode 612 and the front side of cathode 612 faces the separator 614. Cathode 612 may be positioned anywhere within cathode flow channel 610, including having direct contact with the separator 614 and/or gas distribution tube 606.

In one embodiment, separator 614 separates the catholyte and anolyte fluids from one another, thereby keeping the respective reactants and products from mixing in an uncontrolled manner, providing control of two-phase fluid dynamics (flow distribution, mixing, electrode contact, partial pressures of gases), preventing undesirable side reactions, preventing electrode shorting or shunt losses, and allowing for precise control of process conditions at each electrode. In an embodiment separator 614 may be a porous, microporous or nanoporous separator composed of materials including polypropylene, polyethylene, polytetrafluoroethylene, polyvinylidine difluoride, polysulfone, polyethersulfone or a ceramic material (e.g., alumina, zirconia, rare earth oxide, nitride). In an embodiment, separator 614 may be an ion exchange including cation exchange membranes (e.g., perfluorosulfonic acid, sulfonated polyfluorostyrene, sulfonated polystyrene-divinylbenzene, perfluorosulfonimide, and perfluoro carboxylate membranes) or anion exchange membranes (e.g., quaternary ammonium polystyrene-divinylbenzene and doped polybenzimidazole membranes), for example. Separator 614 may be formed into a tubular shape by casting, extrusion, or rolling flat sheets and bonding a seam. In an embodiment, separator 614 is a tubular perfluorosulfonic acid membrane such as Nafion™.

In an embodiment, cathode 612, also known as a cathode electrode, is a high porosity or high surface area material that can conform to a tubular shape and be continuously conductive down the length of its form. Cathode 612 may be a pure metal, an alloy, a conductive polymer, a carbonized or graphitized polymer. In an embodiment cathode 612 has a coating that imparts conductivity, reaction selectivity, catalysis, adsorption, resistance to hydrogen evolution, increased surface area or modifies wetability. In an embodiment, cathode 612 may be made of one or more porous material formats including sintered or bonded particles, sintered or bonded fibers, woven mesh, continuous fibers or filaments, cloths, felts, and electro-spun or melt-spun filamentous forms. In an embodiment the electrode porosity and pore structure of cathode 612 may be uniform, graded or random. In an embodiment cathode 612 has an electrode specific surface area greater than about 10 $m^2$ per 1 $m^2$ superficial area. In an embodiment cathode 612 has an electrode specific surface area greater than about 100 $m^2$ per 1 $m^2$ superficial area. In an embodiment cathode 612 is continuous carbon fibers. The carbon fiber surfaces cathode 612 may be modified to possess carbon oxide species. In another embodiment, the carbon fiber surfaces of cathode 612 are coated with a catalyst that may be an organic material (e.g., adsorbed or bonded molecules or polymers) or an inorganic material (e.g., adsorbed, bonded or electrodeposited metals, semiconductors, alloys and their oxide or sulfide derivatives) or a mixture thereof.

In one embodiment, anode 616, also known as an anode electrode, can be a dimensionally stable anode consisting of an expanded titanium mesh coated with a catalyst. The catalyst is optimized for oxidation of species in an anolyte solution filling anolyte chamber 618, such as water or halides or other redox active materials, at reduced overpotentials or voltage. In some embodiments, the catalyst is a precious metal, noble metal, platinum group metal or oxides of such metals. In an embodiment, the catalyst is iridium oxide.

In an embodiment, anode 616 is in a tubular form, and may be in direct contact with separator 614, and may provide mechanical support to separator 614. In an embodiment, at least one titanium anode current collector tab 626 is affixed to the side of anode 616 and provides a point of attachment for the anode electrical feed-through post 628, which is also titanium.

Figure 6B:
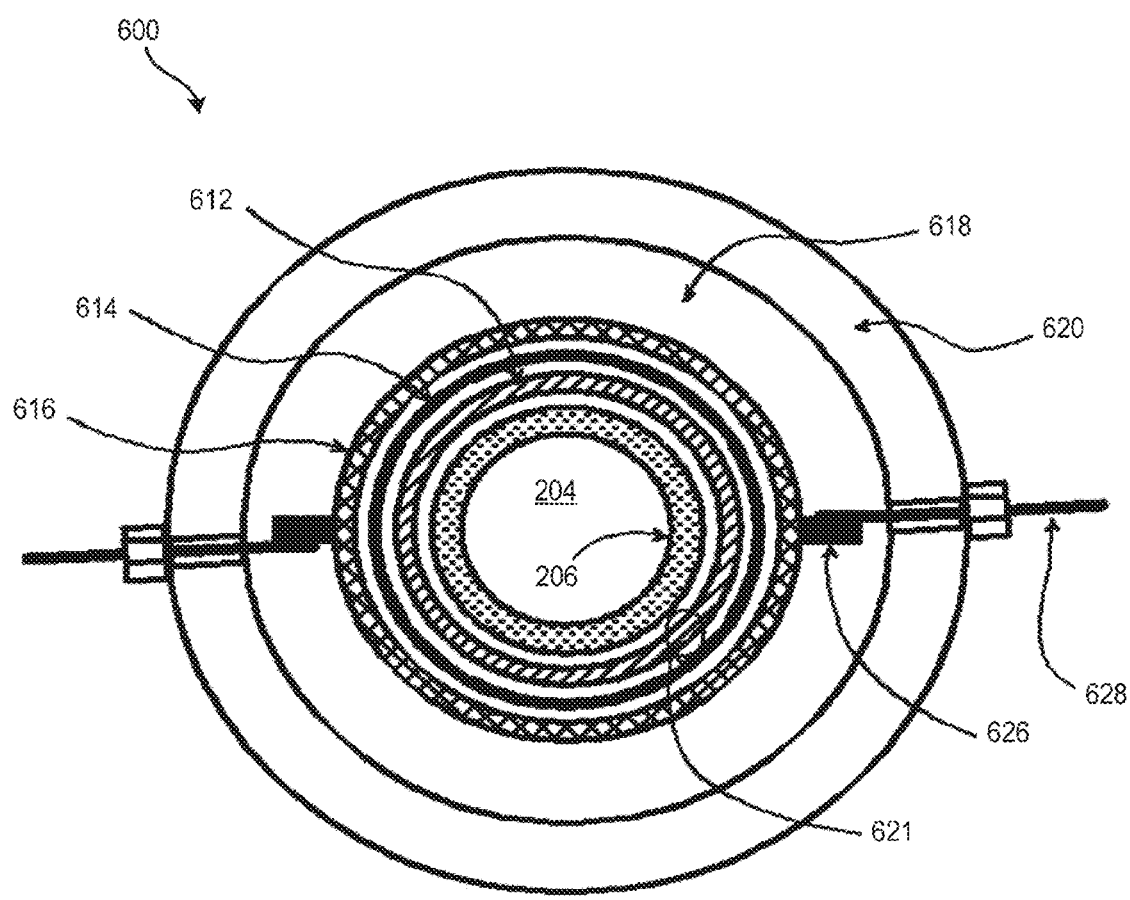

In one embodiment, a heat transfer coil, which is not depicted in FIG. 6A or FIG. 6B, can be positioned in anolyte chamber 618 with feedthroughs using two of the anolyte inlet and outlet/vent ports 622 and 624, respectively. If required, the heat transfer coil may be used in the reactor process for cooling or heating the anolyte solution. In an embodiment, the heat transfer coil is a metal or plastic tube made of a non-corrosive material such as stainless steel alloys, high purity titanium, high nickel alloys, polyvinyl chloride, polypropylene, polyvinylidene difluoride, polytetrafluoroethylene. The heat transfer fluid circulated through the coil may be water, catholyte solution, gas, air, glycol solutions, for example.

Figure 7:
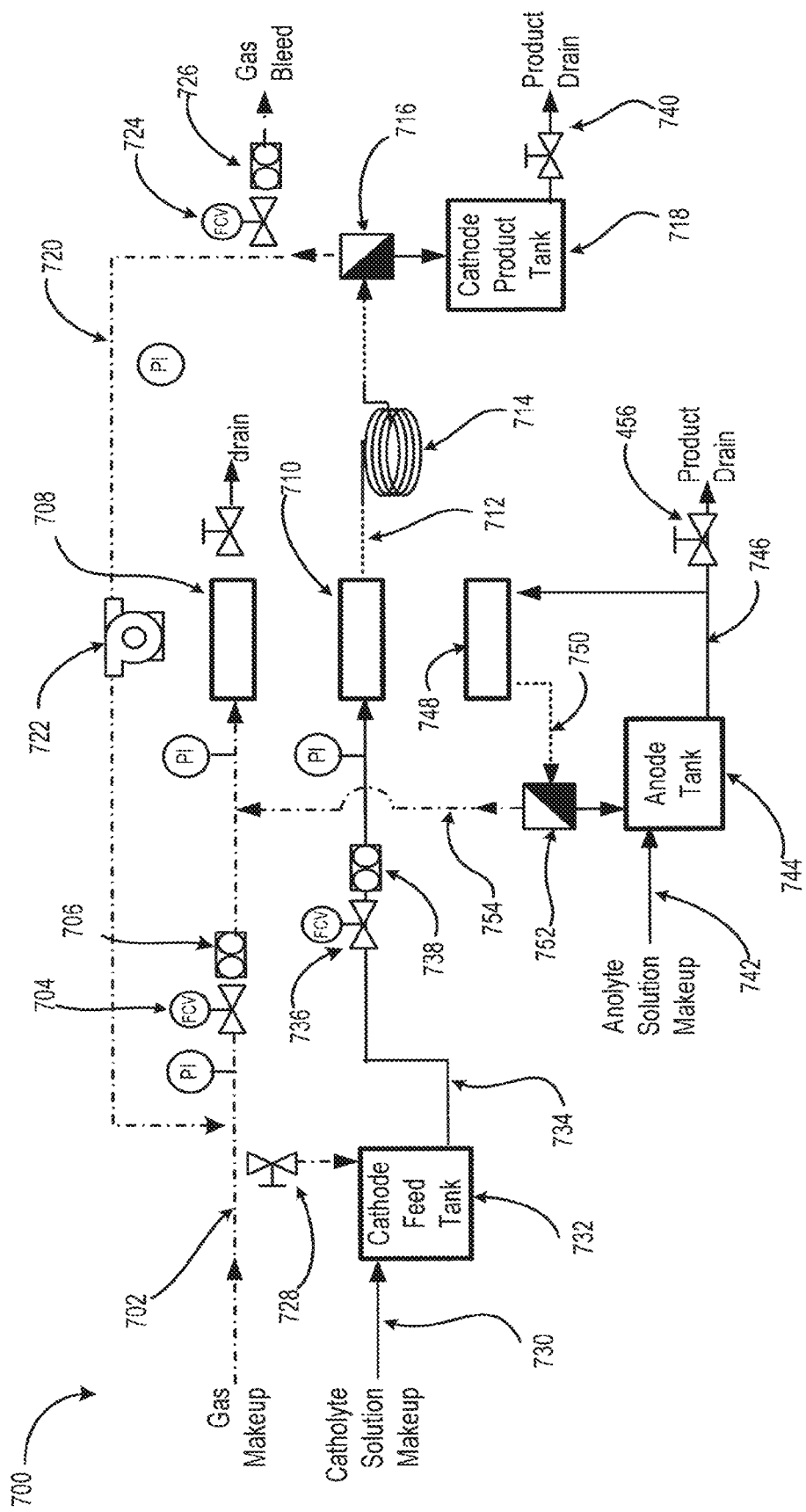
FIG. 7 depicts an embodiment of a reactor system 700 that has a reactor system fluid process flow, also known as a flow pathway, that enables gas recirculation within reactor system 700.

FIG. 7 depicts an embodiment of a reactor system 700 that has a reactor system fluid process flow, also known as a flow pathway, that enables gas recirculation within reactor system 700. A regulated gas makeup stream enters the gas circulation loop through the gas inlet line 702. The gas passes through the gas feed flow control valve 704 and the gas feed flow meter 706 and then enters the gas chamber 708 of the reactor. At least one boundary of the gas chamber is a gas distributor (not depicted in FIG. 7, but described above and depicted in FIG. 6 as gas distributor 606). The gas passes through the gas distributor and into the cathode chamber 710. Excess gas not consumed in electrochemical process exits cathode chamber 710 co-linearly with liquid catholyte and cathodic products formed through the cathode product line 712. The liquid and gas mixture passes through a cooling coil 714 prior to entering a gas-liquid separator 716. The separated liquid, which can contain products formed in cathode chamber 710, is collected in a cathode product tank 718. The separated gas flows through a gas recirculation line 720, through a gas pump 722 and is returned to gas inlet line 702. A portion of the separated gas is removed from the system through a gas bleed flow control valve 724 and a gas bleed flow meter 726. Bleed rate of gas from the system is preferably the same as the mass flow of the gas makeup stream entering the system less the mass consumption of gas in the reactor less the mass production of gas recovered from the anode chamber 746 and added to the gas makeup stream through an anode gas vent 754.

While gas is passing through the system described in reference to FIG. 7, a catholyte solution makeup 730 is added to the cathode feed tank 732 where the head space of the tank can be open to the gas makeup stream through a gas pressure line 728. In some embodiments, the pneumatic pressure for the gas makeup stream may be used to feed the catholyte solution into cathode chamber 710 of the reactor. In additional embodiments, the hydraulic pressure of the catholyte solution makeup may be used to feed the catholyte solution into cathode chamber 710 of the reactor. The catholyte flows from cathode feed tank 732 through the catholyte inlet line 734, passes through a catholyte flow control valve 736 and catholyte flow meter 738 and enters cathode chamber 710 of the reactor. Excess liquid catholyte not consumed in electrochemical process and cathodic products formed exit cathode chamber 710 co-linearly with gas through cathode product line 712. The liquid and gas mixture passes through cooling coil 714 prior to entering gas-liquid separator 716. The separated liquid, which can contain products formed in cathode chamber 710, is collected in cathode product tank 718. The liquid cathode product can be removed from the system during or after operation through the cathode product drain 740.

While gas and catholyte is passing through the system described in reference to FIG. 7 an anolyte solution makeup 742 is added to the anode feed tank 744. The anolyte is supplied through anolyte feed line 746 to the anode chamber 748 by the action of gravity or a pump (not shown). Excess liquid anolyte not consumed in electrochemical process and anodic products formed, including gas, exit the anode chamber collinearly through the anode product line 750 and then pass through a gas-liquid separator 752. The separated liquid is returned to anode feed tank 744 while the separated gas is optionally fed to the gas makeup stream through anode gas vent 754. Anode gas vent 754 also serves to expose anode chamber 748 to the gas inlet line pressure such that the differential pressure between anode chamber 748 and cathode chamber 710 remains constant at any gas inlet line pressure or during pressure fluctuations in the system. The liquid anode or anode product can be removed from the system during or after operation through the anode product drain 756. While gas, catholyte, and anolyte are passing through the system described in reference to FIG. 7 a voltage or current is applied to the reactor by a controller (not shown in FIG. 6 or 7).

Referring back to FIG. 5, it must be noted that the present embodiments herein are not limited to only the electrochemical reactor 600 discussed above, or those disclosed in PCT/US2012/040325; thus, alternative electrochemical reactors may be incorporated in the embodiments herein.

In one embodiment, electrochemical reactor 514 creates two outputs including alkaline hydrogen peroxide 524 output and acid concentrate 526 output, as discussed below with reference to Examples 1-3.

In one embodiment, brine 504 is a solution that contains ions necessary for producing alkaline hydrogen peroxide and acids in two separate streams. The brine 504 may also contain pH buffers and co-solvents compatible with the reaction process, which contribute to the reactive oxygen species output 522 formulation. For example, pH buffers include weak chemical electrolytes chosen from the group including: acetate, citrate, propionate, phosphate and sulfate.

Acyl or acetyl donor 510 includes, but is not limited to, an acyl or acetyl donor chosen from the group including: monoacetin, diacetin, triacetin, acetylsalicylic acid, methyl benzoate, ethyl lactate and tetraacetylethylenediamine (TAED). In alternative embodiments, other synthetic or natural esters, mono-, di- and triacylglycerides and phospholipids having acyl substituents possessing more than one carbon can provide other types of organic peracids by the non-equilibrium reaction mechanism. Acyl or acetyl donor 510 or mixture of donors may be in liquid or solid form, or dissolved in a solvent when reacted with a solution of hydrogen peroxide. Additives concentrate 512, for example, include at least one of the following additives chosen from the group including: salts, surfactants, co-solvents, stabilizers, and emulsifiers.

Figure 8:
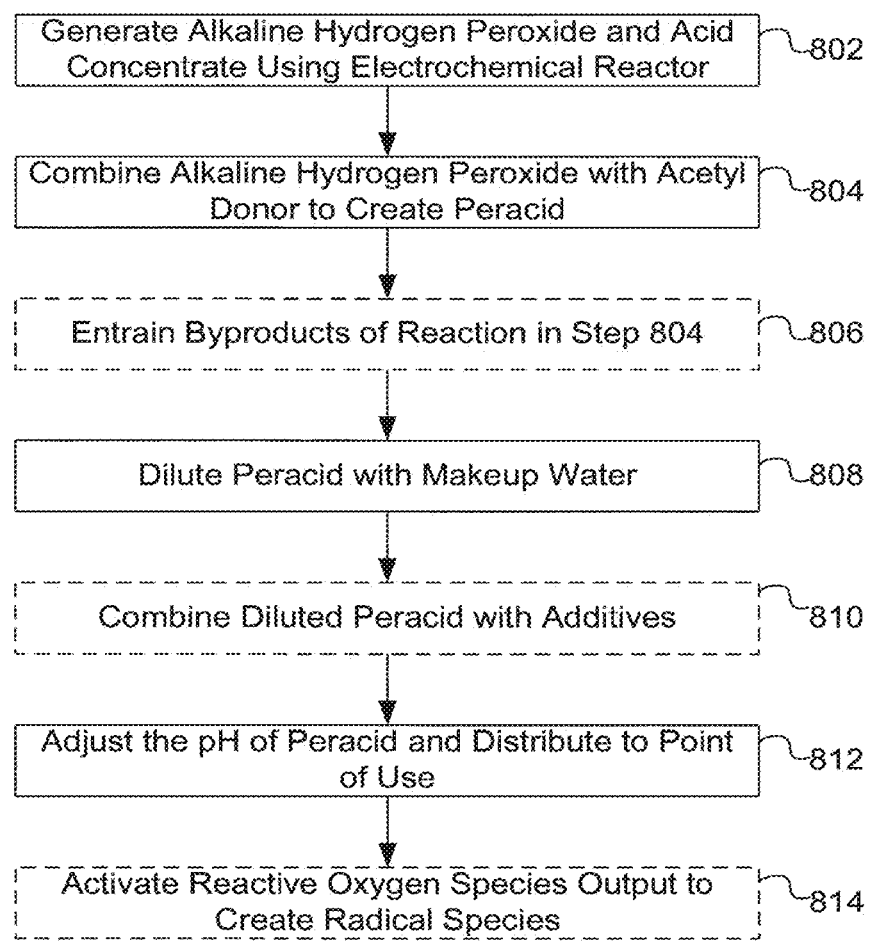
FIG. 8 shows an exemplary method 800 for generating a diluted reactive oxygen species output 522 using system 500 of FIG. 5.

FIG. 8 shows an exemplary method 800 for generating a diluted reactive oxygen species output 522 using system 500 of FIG. 5. In step 802, method 800 generates an alkaline hydrogen peroxide 524 output, and an acid concentrate 526 output. Acid concentrate output 526 is then stored in holding tank 518(1). Exemplary processes for generating outputs 524 and 526 are discussed below in Examples 1-3. In one embodiment, both output streams 524 and 526 are in concentrated liquid forms produced at a constant rate. For example, the alkaline hydrogen peroxide 524 output may contain 0.1 wt % to 3 wt % hydrogen peroxide at pH 12.0 to 13.0. Typical alkaline hydrogen peroxide 524 output may contain 0.3 wt % to 0.8 wt % hydrogen peroxide at pH 12.1 to 12.6. The acid concentrate 526 output may contain 0.1 wt % to 20 wt % depending on the concentration and composition of anolyte solution makeup 742. For example, a 20 wt % sodium acetate solution as anolyte solution makeup 742 may produce 13.5 wt % acetic acid at 85% conversion efficiency. In an alternative embodiment, an anolyte solution makeup 742 is a 5 wt % sodium sulfate solution that may produce 3.6 wt % bisulfate acid at 85% conversion efficiency.

In step 804, the alkaline hydrogen peroxide 524 output is combined with acyl or acetyl donor 510 in mixing tank 520(1) to create alkaline peracid concentrate 524'. In one embodiment, alkaline peracid concentrate 524' may be peroxyacetic acid. In one embodiment, the acyl or acetyl donor 510 is added in proportion to the hydrogen peroxide 524. In one embodiment, the molar ratio of $H_2O_2$ 524 to acyl or acetyl donor 510 reactive group equivalents may range from 1:1.25 to 1:4. For example, a preferred molar ratio range is 1:1.5 to 1:2. If the ratio is too low a high hydrogen peroxide residual will remain in the peracid concentrate where it will significantly quench singlet oxygen. If the ratio is higher than needed to achieve a low hydrogen peroxide residual that does not significantly quench singlet oxygen then excess acyl or acetyl donor is remains unused. In one embodiment, the acyl or acetyl donor is an oxygen-acyl or oxygen-acetyl donor shown in Equation 2a below:

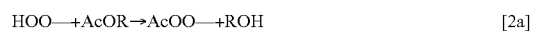

$$\text{HOO—+AcOR} \rightarrow \text{AcOO—+ROH} \quad [2a]$$

Where Ac is acyl [—C(O)R'] or acetyl [—C(O)CH$_3$] and R and R' are hydrocarbon-based substituents. In an alternative embodiment, the acyl or acetyl donor is a nitrogen-acyl or nitrogen-acetyl donor as shown in Equation 2b below:

$$\text{HOO—+AcNR}_2 \rightarrow \text{AcOO—+RNH} \quad [2b]$$

Where Ac is acyl [—C(O)R'] or acetyl [—C(O)CH$_3$] and R and R' are hydrocarbon-based substitutents.

In Equations 2a/2b above, the reaction between an acyl or acetyl donor 510 and alkaline hydrogen peroxide 524 occurs at alkaline pH by nucleophilic attack of the acyl carbonyl carbon atom by the hydrogen peroxide anion, which displaces the donor molecule fragment as an alcohol or amine in a manner analogous to saponification. In some embodiments, the non-equilibrium reactions generalized in Equations 2a/2b are conducted between pH 10 and pH 13.

A particular advantage of the use of non-equilibrium reaction in Equations 2a/2b is that peracid solutions 524" with concentrations of less than approximately 5 wt % peroxyacetic acid and other organic peracids can be produced efficiently and rapidly. Using the non-equilibrium reaction allows the hydrogen peroxide residual to be minimized if necessary. In one embodiment, for example, the peroxyacetic acid water/peroxide concentration ratios can be 10, 100, or 1000 depending on the ratio of hydrogen peroxide to acyl or acetyl donor ratio in Equations 2a/2b.

In one embodiment, at least one molar equivalent of acyl or acetyl donor 510 reactive groups is added for each equivalent of hydrogen peroxide in alkaline hydrogen peroxide anion solution 524 used in Equations 2a/2b to consume all of the hydrogen peroxide.

In optional step 806, as indicated by the dashed lines, method 800 entrains byproducts 528 produced by the reactions of Equations 2a/2b. In one embodiment, byproducts 528 are entrained in solution with the alkaline peracid concentrate 524'. In one embodiment, byproducts 528 are useful as co-solvents, pH buffers, chelating agents or stabilizers and carbon substrates for microbial processes after a chemical oxidation process. For example, the byproduct 528 of acetyl donors 510 of monacetin, diacetin and triacetin is glycerol, a potential co-solvent and favorable carbon source for microbes. In another embodiment, byproduct 528 of acetyl donor 510 of TAED, diacetylethylenediamine, acts as a chelating agent for transition metal ions and potentially serves as a peroxide stabilizer. In yet another embodiment, byproduct 528 is the carboxylic acid produced after alkaline peracid concentrate 524' reacts with a material or decomposes. Alternatively, acetic acid, a byproduct 528 of peroxyacetic acid, serves as a co-solvent, a pH buffer, a chelating agent, and a biological substrate.

In step 808, the resulting alkaline peracid concentrate 524' is then diluted with makeup water 502(2) introduced by pump 516(2) to create a diluted peracid 524" to nearly the point of use concentration and is stored in holding tank 518(2). In optional step 810, as indicated by the dashed outline, additional additives concentrate 512 is combined with diluted peracid 524" and then stored into holding tank 518(2).

In step 812, the diluted peracid's 524" pH is adjusted, by combining diluted peracid 524" with created acid concentrate 526, to the activated pH level for producing reactive oxygen species output 522 The resulting reactive oxygen species output 522 is then distributed to its point of use in liquid form. The reactive oxygen species output 522 may then be used in the form of a liquid, an ice, a foam, an emulsion, a micro-emulsion or an aerosol applied by means such as injection, flooding, spraying, circulation or any other means of conveying a fluid. In one embodiment, the diluted peracid's 524" pH does not require the addition of acid concentrate 526 and is ready for immediate distribution to its point of use.

In one embodiment, during step 812, an acid concentration 526 is combined with diluted peracid 524" such that there is a population of both peracetic aid and peracetic acid anion which react together to generate singlet oxygen according to Equation 3 below:

$$AcOOH + AcOO^- \rightarrow {}^1O_2 + AcOH + AcO^- \quad [3]$$

Wherein the reaction rate for Equation 3 above follows a second order kinetics and is maximized when the ratio of the two forms of peroxyacetic acid is equivalent at its pKa of 8.3. The evolution and release of singlet oxygen occurs over time ranging from minutes to several hours depending on the rate of reaction in Equation 3 above. In one embodiment, the evolution of singlet oxygen from peroxyacetic acid, or other organic peracid having a similar pKa, the pH is between 6.5 and 9.5.

In optional step 814, as indicated by the dashed outline, the reactive oxygen species output 522 may further be activated by means of a Fenton or Fenton-like catalyst, ultrasound, ultraviolet radiation, or thermal activation to produce radical species such as hydroxyl radicals.

Figure 9:
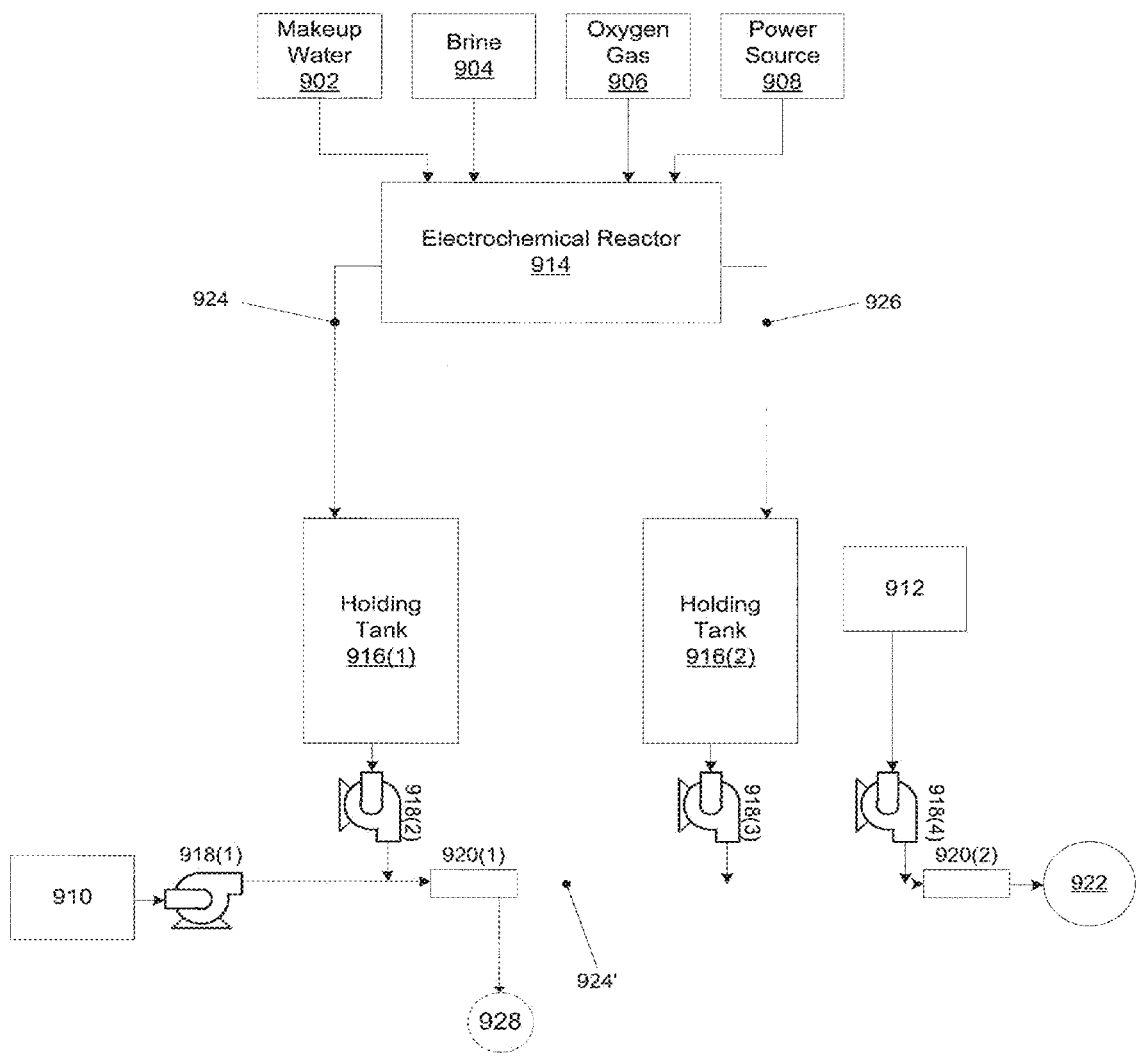
FIG. 9 shows an exemplary system 900 for generating chemicals using an electrochemical reactor 914 and mixing the reactor's 914 outputs together and optionally with other materials to produce a concentrated reactive oxygen species output 922.

FIG. 9 shows an exemplary system 900 for generating chemicals using an electrochemical reactor 914 and mixing the reactor's 914 outputs together and optionally with other materials to produce a concentrated reactive oxygen species output 922. In one embodiment, concentrated reactive oxygen species output 922 is used, but not limited to, in applications where a concentrate is dosed into a liquid stream, which is to be treated or used to distribute the precursor solution throughout a larger system while generating singlet oxygen, for example, as the primary reactive oxygen species in addition to the parent oxidant(s) at the point of use or in-situ. In some embodiments, applications include water and wastewater treatment; cooling tower water treatment and cooling tower system cleaning; desulfurization and deodorization of gases; water treatment in forestry operations, pulp and paper making processes; oil and gas produced water and hydraulic fracturing flowback water treatment.

System 900 includes an electrochemical reactor 914 including inputs of a makeup water 902, brine 904, an oxygen gas 906, and power source 908, an acyl or acetyl donor 910, an additives concentrate 912, holding tanks 916, pumps 918, mixing chambers 920, and reactive oxygen species output 922. In one embodiment, the electrochemical reactor 914 is that embodied by PCT Application No. PCT/US2012/040325 titled "Electrochemical Reactor and Process." An exemplary electrochemical reactor is shown in FIGS. 6-7.

In one embodiment, brine 904 is a solution that contains ions necessary for producing alkaline hydrogen peroxide and acids in two separate streams. In one embodiment, brine 904 may contain 5 wt % sodium sulfate. A small fraction of brine 904 may be fed as a side stream to the cathode feed tank 732 where it is diluted by a factor of 20 with water to 0.25 wt % sodium sulfate before being fed to the catholyte inlet line 734 to serve as an electrolyte. The remaining majority of brine 904 is fed to the anolyte solution makeup 742 and converted to approximately 3.6 wt % sodium bisulfate acid at 85% conversion efficiency. The sodium displaced from sodium sulfate is transported from anode to cathode to support current flow in the reactor and combines with anionic oxygen species produced at the cathode including hydroxide, hydroperoxide and superoxide. In an alternative embodiment, all of brine 904 is fed to anolyte solution makeup 742 while a separate brine (not shown) of different composition and concentration is fed separately into the catholyte feed tank 732. The brine 904 may also contain pH buffers and co-solvents compatible with the reaction process, which contribute to the reactive oxygen species output 922 formulation. For example, pH buffers include weak chemical electrolytes chosen from the group including: acetate, citrate, propionate, phosphate and sulfate. Co-solvents may include a substance chosen from the group including: alcohols such as methanol, ethanol, propanol, propylene glycol, glycol ethers, glycerol, ethyl lactate, soybean oil, vegetable oil, sunflower oil, peanut oil and guar gum.

Acyl or acetyl donor 910 or mixture of donors may be in liquid or solid form, or dissolved in a solvent when reacted with a solution of hydrogen peroxide. Additives concentrate 912, for example, include at least one of the following additives chosen from the group including: salts, surfactants, co-solvents, stabilizers, and emulsifiers.

Figure 10:
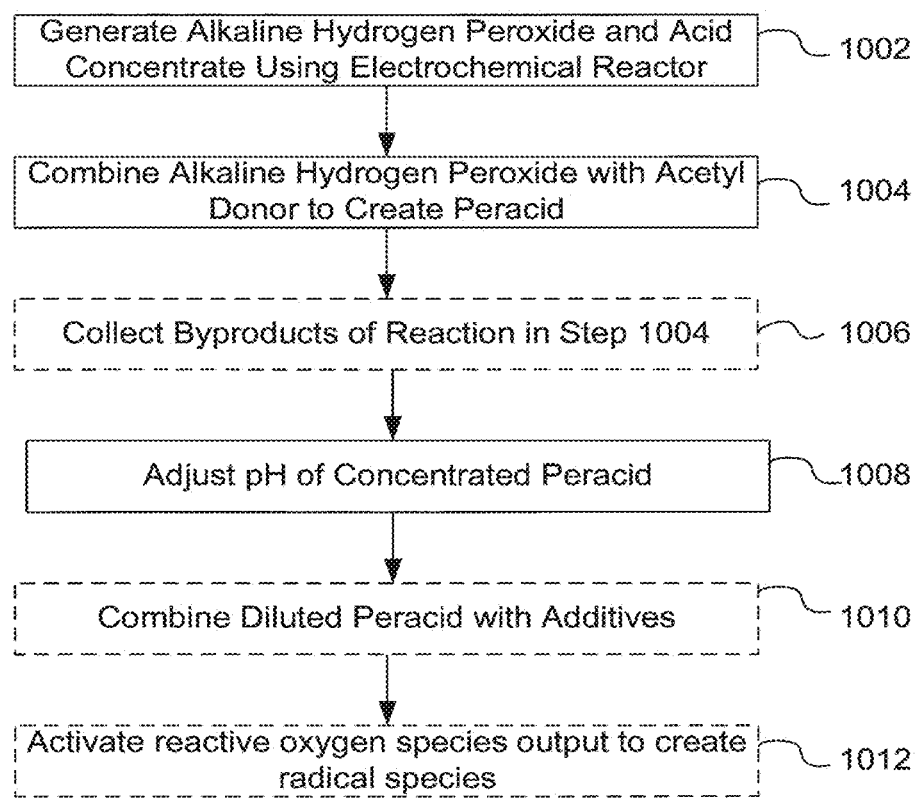
FIG. 10 shows an exemplary method 1000 for generating a concentrated reactive oxygen species output 922 using system 900 of FIG. 9.

FIG. 10 shows an exemplary method 1000 for generating a concentrated reactive oxygen species output 922 using system 900 of FIG. 9. In step 1002, method 1000 generates an alkaline hydrogen peroxide 924 output, and an acid concentrate 926 output. Alkaline hydrogen peroxide output 924 and acid concentrate output 926 is then stored in separate holding tanks 916(1), 916(2), respectfully, for immediate or later use. Alkaline hydrogen peroxide 924 has a longer lifetime prior to use which allows the alkaline hydrogen peroxide 924 to be stored for several minutes to a few hours in holding tank 916(1) without as much decomposition as a peracid at similar concentration. Exemplary processes for generating outputs 924 and 926 are discussed below in examples 1-3. In one embodiment, both output streams 924 and 926 are in concentrated liquid forms produced at a constant rate.

In step 1004, the alkaline hydrogen peroxide 924 output is combined with acyl or acetyl donor 910 in mixing tank 920(1) to create peracid 924'. In one embodiment, the acyl or acetyl donor is an oxygen-acyl or oxygen-acetyl donor shown in Equation 2a above where Ac is acyl [—C(O)R] or acetyl [—C(O)CH$_3$] and R and R' are hydrocarbon-based substituents. In an alternative embodiment, the acyl or acetyl donor is a nitrogen-acyl or nitrogen-acetyl donor as shown in Equation 2b above. Where Ac is acyl [—C(O)R] or acetyl [—C(O)CH$_3$] and R and R' are hydrocarbon-based substituents.

In Equations 2a/2b above, the reaction between an acyl or acetyl donor 910 and alkaline hydrogen peroxide 924 occurs at alkaline pH by nucleophilic attack of the acyl carbonyl carbon atom by the hydrogen peroxide anion, which displaces the donor molecule fragment as an alcohol or amine in a manner analogous to saponification. In some embodiments, the non-equilibrium reactions generalized in Equations 2a/2b are conducted between pH 10 and pH 13.

The use of non-equilibrium reaction in Equations 2a/2b provides peracid solutions 924' with concentrations of less than approximately 5 wt % peroxyacetic acid and other organic peracids that are produced efficiently and rapidly. Using the non-equilibrium reaction allows the hydrogen peroxide residual to be minimized if necessary. In one embodiment, for example, the peroxyacetic acid water/peroxide concentration ratios can be 10, 100, or 1000 depending on the ratio of hydrogen peroxide to acyl or acetyl donor ratio in Equations 2a/2b.

In one embodiment, at least one molar equivalent of acyl or acetyl donor 910 reactive groups is added for each equivalent of hydrogen peroxide in alkaline hydrogen peroxide anion solution 924 used in Equations 2a/2b to consume all of the hydrogen peroxide.

In optional step 1006, as indicated by the dashed lines, byproducts 928 produced by the reactions of Equations 2a/2b are collected. In one embodiment, byproducts 928 are useful as co-solvents, pH buffers, chelating agents or stabilizers and carbon substrates for microbial processes after a chemical oxidation process. For example, the byproduct 928 of acetyl donors 910 of monacetin, diacetin and triacetin is glycerol, a potential co-solvent and favorable carbon source for microbes. In another embodiment, byproduct 928 of acetyl donor 910 of TAED, diacetylethylenediamine, acts as a chelating agent for transition metal ions and potentially serves as a peroxide stabilizer. In yet another embodiment, byproduct 928 is the carboxylic acid produced after a peracid 924' reacts with a material or decomposes. Alternatively, acetic acid, a byproduct 928 of peroxyacetic acid, serves as a co-solvent, a pH buffer, a chelating agent, and a biological substrate.

In step 1008, the concentrated peracid's 924' pH is adjusted, by combining concentrated peracid 924' with created acid concentrate 926, to the activated pH level for producing reactive oxygen species output 922 The resulting reactive oxygen species output 922 is then distributed to its point of use in liquid form. The reactive oxygen species output 922 may then be used in the form of a liquid, an ice, a foam, an emulsion, a micro-emulsion or an aerosol applied by means such as injection, flooding, spraying, circulation or any other means of conveying a fluid.

In one embodiment, during step 1008, an acid concentration 926 is combined with concentrated peracid 924' such that there is a population of both peracetic aid and peracetic acid anion which react together to generate singlet oxygen according to Equation 3 above. Wherein the reaction rate for Equation 3 above follows a second order kinetics and is maximized when the ratio of the two forms of peroxyacetic acid is equivalent at its pKa of 8.3. The evolution and release of singlet oxygen occurs over time ranging from minutes to several hours depending on the rate of reaction in Equation 3 above. In one embodiment, the evolution of singlet oxygen from peroxyacetic acid, or other organic peracid having a similar pKa, the pH is between 6.5 and 9.5.

In one embodiment, the concentrated peracid's 924' pH does not require the addition of acid concentrate 926 and is ready for immediate distribution to its point of use.

In optional step 1010, as indicated by the dashed outline, additional additives concentrate 912 is combined with concentrated peracid 924' and then distributed as reactive oxygen species output 922 to the point of use.

In optional step 1012, as indicated by the dashed outline, the reactive oxygen species output 922 may further be activated by means of a Fenton or Fenton-like catalyst, ultrasound or ultraviolet radiation to produce radical species such as hydroxyl radicals.

Figure 11:
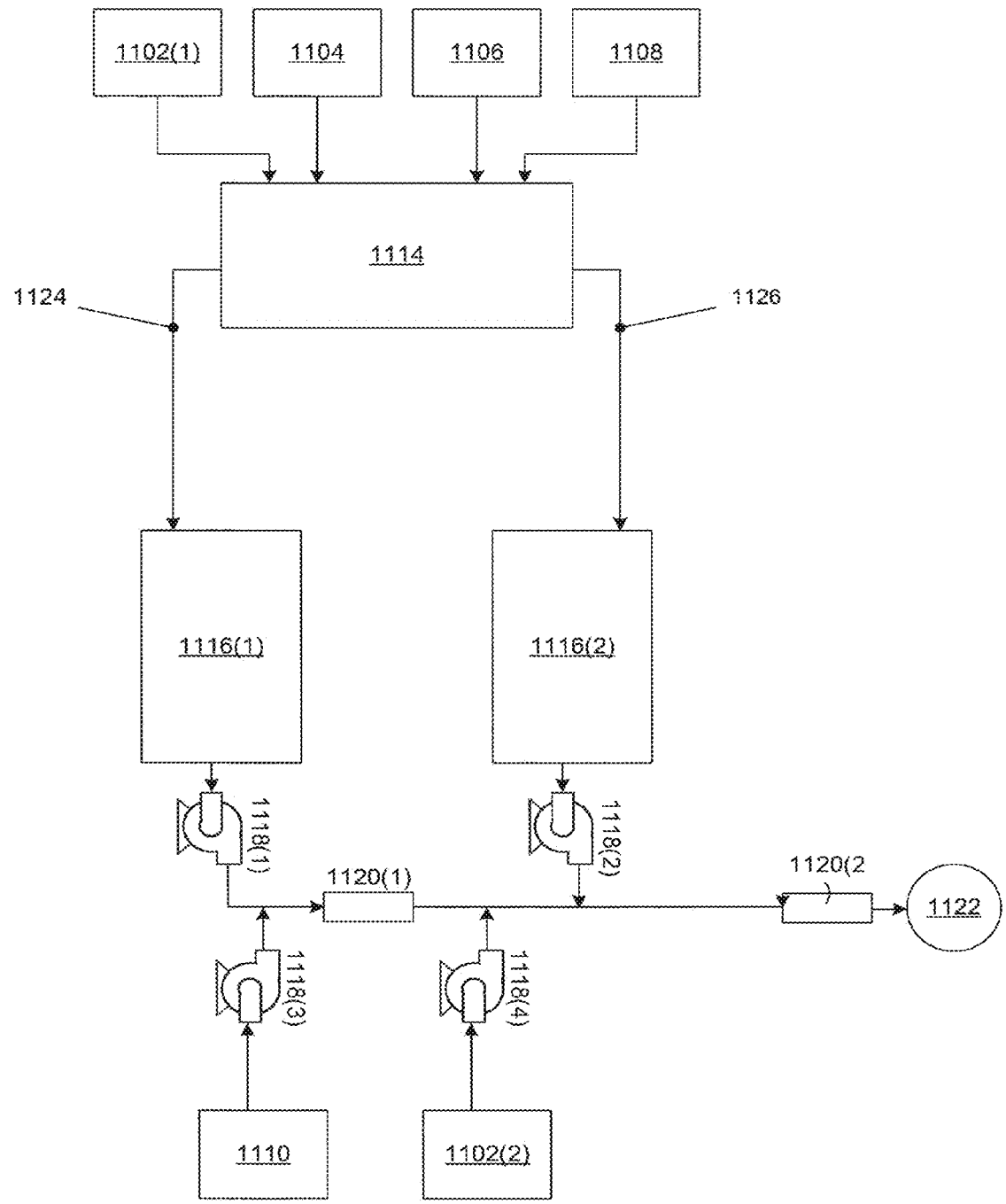
FIG. 11 shows an exemplary system 1100 for generating chemicals using an electrochemical reactor 1114 to produce a superoxide reactive oxygen species output.

FIG. 11 shows an exemplary system 1100 for generating chemicals using an electrochemical reactor 1114 and mixing the reactor's 1114 outputs together and optionally with other materials to produce a superoxide reactive oxygen species output 1122. In one embodiment, the superoxide reactive oxygen species output 1122 is a concentrated superoxide precursor. Alternatively, the superoxide reactive oxygen species output 1122 is a diluted superoxide precursor. In one embodiment, superoxide reactive oxygen species output 1122 is used, but not limited to, applications where a concentrate is dosed into a liquid stream, or applied to a surface or material. In some embodiments, applications include water and wastewater treatment; cooling tower water treatment and cooling tower system cleaning; desulfurization and deodorization of gases; water treatment in forestry operations, pulp and paper making processes; oil and gas produced water and hydraulic fracturing flowback water treatment; in-situ chemical oxidation for remediation of soil and groundwater; ex-situ chemical oxidation for remediation of soil; construction or demolition debris; hard surface cleaning and decontamination; cleansing applications in food, dairy, beverage and biopharma production and processing; cleaning of membrane filtration systems.

System 1100 includes an electrochemical reactor 1114 including inputs of a makeup water 1102(1), brine 1104, an oxygen gas 1106, and power source 1108, an additives concentrate 1110, holding tanks 1116, pumps 1118, mixing chambers 1120, and superoxide reactive oxygen species output 1122. In one embodiment, the electrochemical reactor 1114 is that embodied by PCT Application No. PCT/US2012/040325 titled "Electrochemical Reactor and Process." An exemplary electrochemical reactor is shown in FIGS. 6-7.

In one embodiment, brine 1104 is a solution that contains ions necessary for producing alkaline hydrogen peroxide and acids in two separate streams. The brine 1104 may also contain pH buffers and co-solvents compatible with the reaction process, which contribute to the reactive oxygen species output 1122 formulation. For example, pH buffers include weak chemical electrolytes chosen from the group including: acetate, citrate, propionate, phosphate and sulfate. Co-solvents may include a substance chosen from the group including: alcohols such as methanol, ethanol, propanol, propylene glycol, glycol ethers, glycerol, ethyl lactate, soybean oil, vegetable oil, sunflower oil, peanut oil and guar gum.

Additives concentrate 1110, for example, include at least one of the following additives chosen from the group including: salts, surfactants, co-solvents, stabilizers, and emulsifiers.

Figure 12:
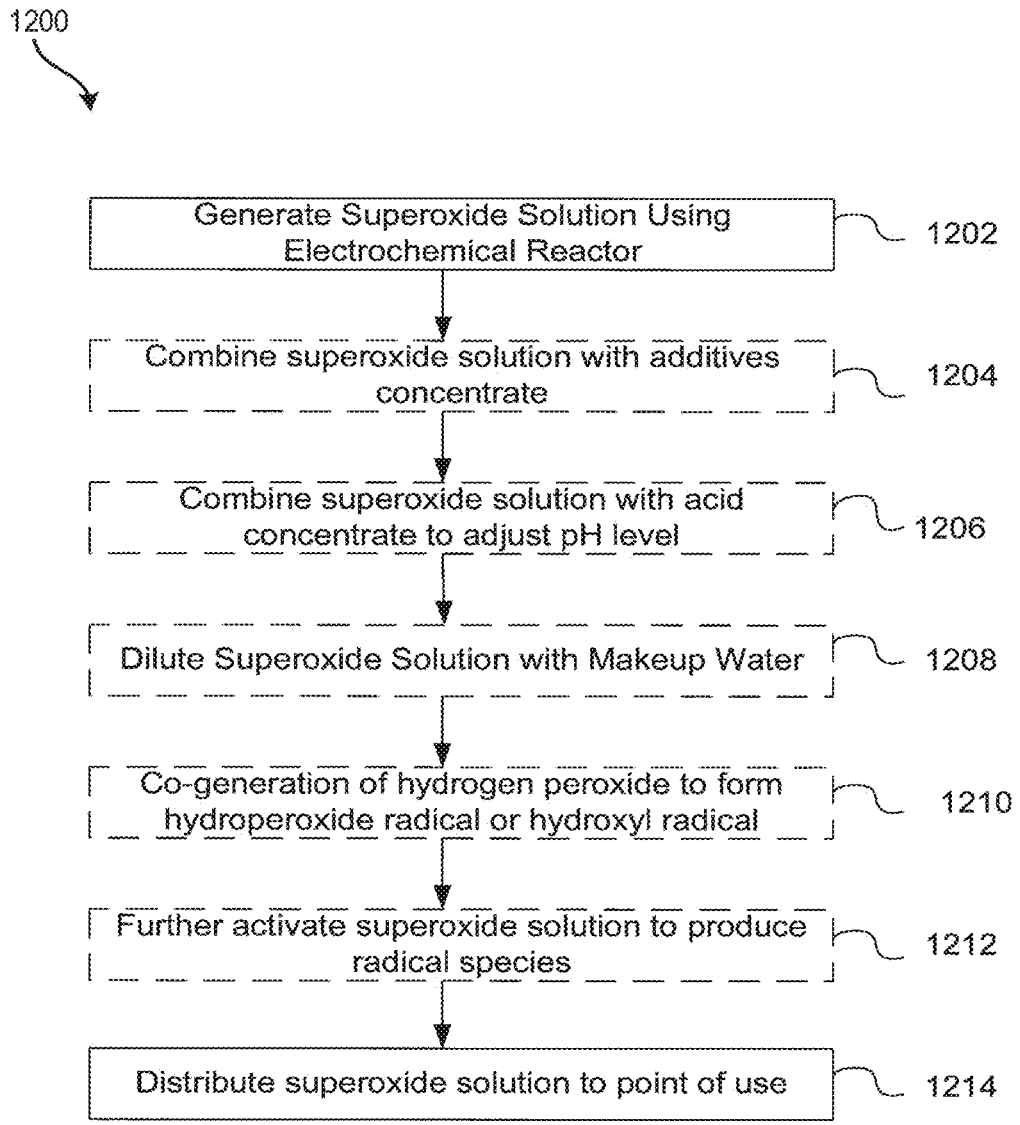
FIG. 12 shows an exemplary method 1200 for generating a concentrated superoxide reactive oxygen species output 1122 using system 1100 of FIG. 11, in one embodiment.

FIG. 12 shows an exemplary method 1200 for generating a concentrated superoxide reactive oxygen species output 1122 using system 1100 of FIG. 11, in one embodiment. In step 1202, electrochemical generator 1114 is used to create a superoxide solution 1124, as depicted below in example 4. In one embodiment, superoxide solution 1124 additionally contains hydrogen peroxide co-generated with superoxide. In yet another embodiment, in step 1202, electrochemical generator 1114 creates superoxide solution 1124, with or without co-generation of hydrogen peroxide, and additionally co-generates an acid concentrate 1126. The proportion of superoxide to hydrogen peroxide co-generated can be adjusted by the nature of the cathode surface. For carbon cathodes, a higher degree of oxidation of the cathode surface can correlate with higher superoxide to hydrogen peroxide ratios. Also, when using such cathodes increasing cathodic current density is correlated with increasing superoxide to hydrogen peroxide production ratios. The molar ratio of superoxide to hydrogen peroxide co-generated by the reactor can range from approximately 0.01:1 to 10:1. Preferred molar ratios ranges of superoxide to hydrogen peroxide are 0.5:1 to 1.5:1, 1.5:1 to 3:1 and 3:1 to 5:1. Electrochemically generated superoxide solutions in the above ranges are more stable than those solutions generated from bulk chemicals. Superoxide solutions produced from bulk chemicals, at modestly alkaline pH's, i.e. 11-13 pH, contain HOOH in equilibrium with NaOOH, causing the bulk chemical superoxide solutions to have less stability. In contrast, electrochemically generated superoxide solutions can be made to initially contain only NaOOH, which in the presence of only $NaO_2$ and NaOH produces more stable solutions. Upon adding a proton source, such as an acid, the degradation of electrochemically generated superoxide solutions accelerates.

In alternate embodiments, hydrogen peroxide may be added from an independent source including bulk chemical concentrate production as described in conjunction with FIGS. 1-4. Superoxide solution 1124 may then be used as formed, or stored in holding tank 1116(1). Co-generated acid is stored in holding tank 1116(2).

In step 1204, the superoxide solution 1124 is combined with additives 1110, such as salts, co-solvents, or surfactants to increase lifetime and working time of superoxide formulations; the resulting solution may then be distributed to its point of use. In step 1206, superoxide solution 1124 is combined with additives concentrate 1126 to adjust the pH level of the superoxide for pH sensitive applications such as groundwater and soil remediation. The initial pH can range from pH 8 to pH 13. A preferred initial pH range is pH 9 to pH 12. As the superoxide solution reacts and is consumed, the pH decreases, as shown by the superoxide data examples below, leaving a final pH closer to neutral. In step 1208, the superoxide solution 1124 is diluted with makeup water 1104(2) for concentration sensitive applications.

In step 1210, the electrochemical reactor 1114 creates an output of both hydrogen peroxide and superoxide; method 1200 then generates the hydroperoxyl radical and hydroxyl radical according to the Equations 4-7 below.

$$O_2.^- + H_2O_2 \leftrightarrow {}^1O_2 + .OH + OH^- \quad [4]$$

Wherein the Haber-Weiss reaction of Equation 4 between superoxide radical anion and hydrogen peroxide form excited state (singlet) molecular oxygen, hydroxyl radical and hydroxide anion. Hydroxyl radicals will react with an excess of hydrogen peroxide in an equilibrium reaction forming water and the hydroperoxyl radical as shown below in Equation 5:

$$.OH + H_2O_2 \rightarrow H_2O + HO_2. \quad [5]$$

In one embodiment, hydroperoxyl radicals further subsequently react with excess hydrogen peroxide to form water, ground state molecular oxygen and hydroxyl radical as shown below in Equation 6:

$$HO_2. + H_2O_2 \rightarrow H_2O + O_2 + .OH \quad [6]$$

In step 1210, as the superoxide solution 1124 pH decreases the population of hydroperoxyl radical increases via the equilibrium in Equation 7 below:

$$HO_2. \leftrightarrow O_2.^- + H^+ \quad [7]$$

In one embodiment, hydroxyl radical evolution is most relevant at lower concentrations of parent oxidants since hydroxyl radicals rapidly react with the parent oxidants. In one embodiment, evolved hydroxyl radicals initiate oxidation reactions which the parent oxidants are not capable of, thereby enhancing the oxidative activity.

In yet another embodiment, in step 1212, the superoxide formulation 1124 containing hydrogen peroxide may be exposed to a Fenton catalyst, Fenton-like catalyst, ultrasound, ultraviolet radiation, or thermal activation (not shown in FIG. 11) to produce radical species such as hydroxyl radicals.

Steps 1204-1212 are all optional steps as shown by the dashed outlines. The implementation of steps 1204-1212 depends on the application required. For example, pH sensitive uses such as soil and groundwater remediation require diluted superoxide solution 1124, and additional additives may be required to be combined with the solution.

In step 1214, the superoxide solution 1124, and any additional components combined in optional steps 1204-1212 are distributed to the point of use. In one embodiment, the point of use is various substrates including materials, compounds, atoms or ions (organic or inorganic) to be reduced, oxidized or degraded and microorganisms to be denatured or killed. In one embodiment, the superoxide solution 1124 is used soon after its production due to its relatively short half life determined by initial concentration, salinity, pH, temperature and other oxidants and constituents present. In another embodiment, the resulting superoxide solution as distributed as superoxide reactive oxygen species output 1122 is then used in the form of, for example, a liquid, an ice, a foam, an emulsion, a microemulsion or an aerosol applied by means such as injection, flooding, spraying, circulation or by any other means of conveying a liquid.

DEFINITIONS

Generally, terms used herein not otherwise specifically defined have meanings corresponding to their conventional usage in the fields related to the invention.

"Reactive Oxygen Species" means a species such as singlet oxygen, superoxide, the hydroxyl radical and the hydroperoxyl radical, for example. Other reactive oxygen species are known in the art. Reactive species are often characterized by their strong oxidizing or reducing activity, high chemical reactivity and often short or transient lifetimes in aqueous media.

An acyl group, as known in the art, is a —C(O)R' group, where R is a hydrocarbon-based group. An acetyl group is a type of acyl group where R' is a methyl group, i.e., —C(O)CH$_3$. An "Acyl donor", particularly an "Acetyl donor" functions to transfer an acyl or particularly an acetyl group, respectively, to another chemical species as shown in equations 2a and 2b above. Acyl or acetyl donors can be oxygen-acyl or oxygen-acetyl donors as shown in Equation 2a or nitrogen-acyl or nitrogen-acetyl donors as shown in Equation 2b above. "Acyl Donor" includes, but is not limited to, an acetyl donor chosen from the group including: monoacetin, diacetin, triacetin, acetylsalicylic acid, and tetraacetylethylenediamine (TAED). Acyl donors that are not acetyl donors include methyl benzoate and ethyl lactate. In alternative embodiments, "Acyl Donor" may include other synthetic or natural esters, mono-, di- and triacylglycerides and phospholipids having acyl substituents possessing more than one carbon which provide other types of organic peracids by the non-equilibrium reaction mechanism.

"Reactive groups" in association with an "acetyl donor" or "acyl donor" distinguish between those acetyl or acyl groups in such donors that will react with alkaline hydrogen peroxide and those that are non-reactive. One example is TAED, shown below, where only two of the four acetyl groups are reactive.

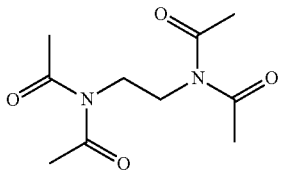 [SMILES: CC(=O)N(CCN(C(C)=O)C(C)=O)C(C)=O]

Another example is triacetin, shown below, where all three acetyl groups are reactive.

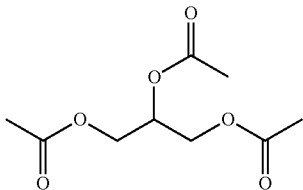

Yet another example is ethyl lactate, shown below, where only one acyl group is reactive.

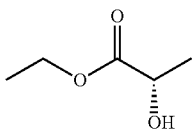

"Additives concentrate" or "Additives" means any additional substance added to the chemical formulations described herein. "Additives concentrate", or "additives" includes, for example, at least one of the following additives chosen from the group including: salts, surfactants, co-solvents, stabilizers, and emulsifiers, mineral acids, organic acids, alkali, pH buffers, non-oxidizing molecules, ionized molecules and ionized atoms.

"Alkali concentrate" or "Alkali" includes any alkali material. In a preferred embodiment, alkali concentrate is an aqueous sodium hydroxide solution, or an aqueous potassium hydroxide solution.

"Salts" include, for example, at least one salt chosen from the group including: lithium, sodium and potassium chloride; lithium, sodium and potassium sulfate; calcium chloride or magnesium sulfate below pH 9; and lithium, sodium and potassium salts of acetate, citrate, propionate, phosphate and polyphosphates.

"Surfactants" may be anionic and nonionic for charge compatibility and include at least one surfactant chosen from the group including: sulfonic acid salts, alcohol sulfates, carboxylic acid salts, fatty acids, polyether alcohols and sodium dodecyl sulfate.

"Co-solvents" include, for example, at least one co-solvent chosen from the group including: alcohols such as methanol, ethanol, propanol, propylene glycol, glycol ethers, glycerol, ethyl lactate, soybean oil, vegetable oil, sunflower oil, peanut oil and guar gum.

"Stabilizers" include, for example, at least one stabilizer chosen from the group including: phosphoric acid, phytic acid, tetrasodium pyrophosphate, sodium hexametaphosphate, sodium tetrametapyrophosphate, ethylenediamine tetraacetic acid and citric acid, chelating agents, and saline water.

"Emulsifiers" include, for example, at least one foaming and antifoaming agents chosen from the group including: surfactants, oils, co-solvents and polymers including polyethylene glycol.

"Foaming" and "antifoaming agents" include, for example, surfactants, oils, co-solvents and polymers including polyetheylene glycol.

"Byproducts" means any additional substance that results from a chemical reaction. Byproducts may be useful as co-solvents, pH buffers, chelating agents or stabilizers and carbon substrates for microbial processes after a chemical oxidation process. For example, the byproduct of monoacetin, diacetin and triacetin is glycerol, a potential co-solvent and favorable carbon source for microbes. Another example is the byproduct of TAED, diacetylethylenediamine, which can act as a chelating agent for transition metal ions and potentially serve as a peroxide stabilizer. Another example of a byproduct is the carboxylic acid produced after a peracid reacts with a material or decomposes. Acetic acid, a byproduct of peroxyacetic acid, can serve as a co-solvent, a pH buffer, a chelating agent, and a biological substrate.

Oxygen-based oxidants have a wide variety of oxidation potentials, reaction pathways, and oxidation kinetics depending on what reactive materials are present and the conditions they are used in. Because of these differences the oxidation products and oxidation byproducts will vary between oxidant type, amount used and other conditions such as pH and temperature. Oxidation products of organic materials are typically organic acid fragments, small organic acids, alcohols and substituted alkanes. Complete mineralization of organic materials to carbon dioxide and water can occur. Often, the organic oxidation products are more readily consumed by biological activity than the original materials.

Formation of other undesirable or regulated oxidation byproducts will depend on both the oxidant and the reactive material(s) present that may be oxidized. Organic materials possessing nitrogen atoms may be oxidized and release nitrate as a byproduct. This is a particular issue during the oxidation of natural organic material (NOM) such as humic substances and reduced hydrocarbons from conventional oil reservoirs, oil sands and natural gas shales.

"Hydrogen Peroxide Concentrate" typically means an aqueous hydrogen peroxide solution. However, in alternative embodiments, hydrogen peroxide concentrate may include other chemical forms of hydrogen peroxide chosen from the group including: calcium peroxide, potassium peroxide, sodium peroxide, lithium peroxide, percarbonates, and perborates.

"Brine" contains ions necessary for producing alkaline hydrogen peroxide and acids in two separate fluid streams, for example. Brine may also be formulated to contain pH buffers and co-solvents compatible with the generation process, which contribute to the hydrogen peroxide solution formulation.

When a Markush or other grouping is used herein, all individual members of the group and all combinations and subcombinations possible of the group are intended to be individually included in the disclosure. Every formulation or combination of components described or exemplified can be used to practice the invention, unless otherwise stated.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

One of ordinary skill in the art will appreciate that process methods (adding, mixing, dispensing, etc.), device elements, materials (e.g., salts, acids, bases, etc.), analytical and spectroscopic methods, and system configurations other than those specifically exemplified can be employed in the practice of the invention without resort to undue experimentation. All art-known functional equivalents, of any such methods, device elements, materials, and configurations are intended to be included in this invention. Whenever a range is given in the specification, for example, range of ratios, a temperature range, a time range, or a composition range, all intermediate ranges and subranges, as well as all individual values included in the ranges given are intended to be included in the disclosure.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

Each reference cited herein is incorporated by reference herein in its entirety. References can be incorporated by reference herein to provide additional description of device and system

THE EXAMPLES

Example 1

Cogeneration of Alkaline Hydrogen Peroxide and Citric Acid

A reactor system with the reactor of FIG. 6A and fluid process flow illustrated in FIG. 4 was used in this example. The cathode's active superficial area was approximately 255 $cm^2$. The anolyte reservoir and chamber were charged with a 10% weight to volume solution of trisodium citrate in distilled water. A filtered compressed air stream was fed into the gas feed line at a rate of 5 liters per minute at 1.3 psig. A solution of 0.05 M sodium sulfate and 0.01 M sodium chloride in distilled water was fed into the catholyte feed line at a rate of 13 mL per minute at approximately 1.0 psig. A DC current was applied to the reactor at 5.0 amps and 4.55-4.65 volts. The catholyte output reached a steady state composition of 720 mg/L hydrogen peroxide with a pH of 12.4 (pH measured at a 20-fold dilution) within twelve minutes of applying the electric current and remained there at ambient temperature near 15° C. until the process conditions were changed after 29 minutes. The air feed rate was then increased to ca. 15 liters per minute at 2 psig. The catholyte inlet pressure increased to 1.5 psig. The DC current was maintained at 5.0 amps while the voltage increased to 4.74 volts. The catholyte output reached a new steady state composition of 1040 to 1080 mg/L hydrogen peroxide at a pH of 12.3 (pH measured at a 20-fold dilution) within five minutes of changing the air feed rate until the reactor was shut down after 46 minutes.

To the existing catholyte feed was added 0.001 M trisodium citrate and the reactor restarted under the previous process conditions and nearly the same catholyte output was achieved at 1000-1080 mg/L hydrogen peroxide at a pH of 12.3 decreasing to 12.0 (pH measured at a 20-fold dilution) during the first 35 minutes of operation. While maintaining the current at 5.0 amps (air feed was reduced to 5 liters per minute at 46 minutes) the pH of the catholyte output continued to decrease to a pH of 10.2 (not diluted) at 2 hours 25 minutes when the system was shut down. The anolyte solution was drained from the reactor and had a pH of 2.5 indicating the production of citric acid.

Example 2

Generation of Hydrogen Peroxide by Cogeneration of Alkaline Hydrogen Peroxide and Sulfate Acids A reactor system with the reactor of FIG. 6A and fluid process flow illustrated in FIG. 4 was used in this example. The cathode's active superficial area was approximately 255 $cm^2$. The anolyte reservoir and chamber were charged with a 1.9 L solution of 0.25 M sodium sulfate in distilled water, initial pH=9.5. A ca. 93% oxygen gas stream generated by a pressure swing adsorption oxygen concentrator was circulated through the gas feed line at a rate of 14.5 liters per minute at 2.9 psig. A 0.02 M solution of sodium sulfate in distilled water was fed into the catholyte feed line at a rate of 12.8 mL per minute at 1.5 psig. A DC current was applied to the reactor at 7.0 amps and 3.7 volts between anode and cathode posts. The catholyte output reached a steady state composition of 2400 to 2450 mg/L hydrogen peroxide at a pH of 12.5 within twenty minutes of applying the electric current and remained there with an output product temperature of 19 to 20° C. until about 60 minutes. Over the following 75 minutes the hydrogen peroxide output concentration decreased to about 2000 mg/L with a pH of 12.5 and temperature increasing to 21° C. The process was shut down after a total operating time of 135 minutes. The total collected hydrogen peroxide product stream had a volume of 1.7 L with a measured composition of 2300 mg/L hydrogen peroxide at pH 12.5. The anolyte was removed from the reactor with a volume of 1.8 L and a measured pH of 1.42 indicating conversion of sodium sulfate to its acid forms. The hydrogen peroxide and anolyte product streams were combined producing a pH neutralized product with a measured composition of 1050 mg/L hydrogen peroxide at a pH of 9.8, 0.2 pH units higher than the starting anolyte solution, and a calculated sodium sulfate content of 0.15 M concentration.

Example 3

Cogeneration of Alkaline Hydrogen Peroxide and Sodium Hypochlorite

A reactor system with the reactor of FIG. 6A and fluid process flow illustrated in FIG. 4 was used in this example.

The cathode's active superficial area was approximately 255 cm². The anolyte reservoir and chamber were charged with a 1.8 L solution of 0.25 M sodium hydroxide and 0.067 M sodium chloride in distilled water, initial pH=13.2. A ca. 93% oxygen gas stream generated by a pressure swing adsorption oxygen concentrator was circulated through the gas feed line at a rate of 14.5 liters per minute at 3.0 psig. A 0.02 M solution of sodium sulfate in distilled water was fed into the catholyte feed line at a rate of 12.8 mL per minute at 1.7 psig. A DC current was applied to the reactor at 7.0 amps and 2.7 volts between anode and cathode posts. The catholyte output reached a steady state composition of 2300 to 2450 mg/L hydrogen peroxide at a pH of 12.6 within twenty minutes of applying the electric current and remained there with an output product temperature of 19 to 21° C. until the process was shut down after 138 minutes of operation. The final output pH had decreased slightly to 12.5. The total collected hydrogen peroxide stream had a volume of 1.7 L with a measured composition of 2350 mg/L hydrogen peroxide at pH 12.6. The anolyte was removed from the reactor with a volume of 1.75 L and a measured pH of 12.0. The total chlorine content was measured to be near 40 mg/L+/−10 mg/L.

Example 4

Superoxide Production

Evidence for enhanced superoxide production was observed using the electrochemical reactor of FIG. 6A and process flow of FIG. 7. At 5 amps a relatively low hydrogen peroxide production current efficiency of less than 60% is accompanied by a lower than normal pH (e.g., 2000-2400 mg/L hydrogen peroxide and pH 12.40). As the current density is increased to 8 amps the hydrogen peroxide production current efficiency decreases rapidly to less than 40% and the pH decreases by at least 0.1 pH units (e.g., 2600 mg/L hydrogen peroxide and pH 12.26). If the loss of hydrogen peroxide production efficiency was due to current going into the four electron reduction of molecular oxygen in Equation 8 below, or the splitting of water in Equation 9 below, then a significant amount of hydroxide would be generated thereby raising the pH significantly, which is not observed.

$$O_2 + H_2O + 2e^- \leftrightarrow HO_2^- + OH^- \quad [8]$$

$$2H_2O \leftrightarrow 4e^- + O_2 + 4H^+ \quad [9]$$

Furthermore, significant electrolytic splitting of water at the cathode would require a larger overpotential at the cathode (ca. 0.5 V more negative) and be reflected in a higher cell voltage. However, the cell voltage remains unchanged relative to higher efficiencies as in the examples above.

Additional evidence in support of superoxide production is the decoloration of methylene blue dye with the fresh cathode output solution produced with the above characteristics. A 25 mg/L solution of methylene blue can be decolorized to the eye, partially within minutes and completely within 5 hours of mixing with the aforementioned freshly produced cathode product (e.g., 2600 mg/L hydrogen peroxide and pH 12.26). The decoloration of methylene blue does not occur on this time scale or at all when using catholyte product aged for at least 24 hours or using store bought hydrogen peroxide to make a simulated catholyte product in control experiments. The decoloration of methylene blue dye is thought to be caused by or at least initiated by the direct action of generated superoxide or by the evolution of hydroxyl radicals via the Haber-Weiss reaction in Equation 4, below, over time relative to the control experiments.

$$O_2^{.-} + H_2O_2 = O_2 + .OH + OH^- \quad [4]$$

Example 5

Generation of Singlet Oxygen Using Bulk Chemical Precursors

An generation system from FIG. 1 and associated method from FIG. 2 was used in the present example to show an exemplar of producing a singlet oxygen precursor formulation using bulk chemical precursors. A 30 g/L aqueous hydrogen peroxide solution 102 is pH adjusted with sodium hydroxide alkali concentrate 104 to pH 12.0 to 12.4, using approximately 50 g sodium hydroxide per liter of 30 g/L hydrogen peroxide. The resulting alkaline hydrogen peroxide solution is mixed 120(1) and reacted with an acetyl donor 106 of triacetin in a ratio of 128 g triacetin per 1 liter alkaline hydrogen peroxide solution. The resulting alkaline peracid concentrate 122' will contain approximately 65 g/L peroxyacetic acid and 0.9 g/L hydrogen peroxide assuming 97% conversion of the hydrogen peroxide to peroxyacetic acid. The resulting alkaline peracid concentrate 122' will also contain about 54 g/L glycerol byproduct 124.

The peroxyacetic acid concentrate is then diluted to its point of use concentration before or during pH adjustment to minimize losses resulting from accelerated peroxyacetic acid decomposition at higher concentrations when in its activated pH range. In the present example, the above peroxyacetic acid concentrate is diluted to 1.5 g/L, a dilution factor of 41.5 times. The peroxyacetic acid solution is diluted with 40.5 L of make up water 108 (fresh water or salt water) and then mixed with an acid concentrate 112 necessary for adjusting the pH to activate singlet oxygen evolution, where an initial pH range is between pH 8 and pH 9. For example, 12 g hydrochloric acid (100% base) is added per 1 L of concentrate. Additionally, other additives may be added to the solution by combining them with water 108 used to dilute alkaline peracid concentrate 122', for example additives such as: sodium or calcium chloride, tetrasodium pyrophosphate, sodium lauryl sulfate and glycerol.

For the above exemplary singlet oxygen precursor formulation the hydrogen peroxide stock solution, alkali types, and acid types and other additives including salts, surfactants, co-solvents, stabilizers, and emulsifiers can be substituted with compatible alternatives known in the art to accommodate specific application requirements. The resulting singlet oxygen reactive oxygen species output 116 may then be used in the form of a liquid, an ice, a foam, an emulsion, a microemulsion or an aerosol applied by means such as injection, flooding, spraying, circulation or by any other means of conveying a fluid.

The above example 5 may also be implemented using the system of FIG. 3 and method of FIG. 4, without diluting the alkaline peracid concentrate 122'.

Example 6

Singlet Oxygen from Electrochemically Generated Chemicals

A generation system from FIG. 5 and associated method from FIG. 8 was used in the present example to show an exemplar of producing a singlet oxygen precursor formulation using an electrochemical generator, in one embodiment.

In the present example of singlet oxygen precursor formulation, the hydrogen peroxide, alkali, and acid may be generated electrochemically and on site as an alternative to supplying them as bulk chemicals. Alkaline Hydrogen Peroxide 524 and acid concentrate 526 are generated by electrochemical reduction. Electrochemical reduction of oxygen is conducted at a suitable cathode and water is oxidized at a suitable anode in an electrochemical reactor 514 in which the anode and cathode chambers are separated by a membrane. Oxygen gas 506 and a 4 g/L aqueous sodium acetate solution 504 are supplied to the cathode while 50 g/L aqueous sodium acetate solution 504 is supplied to the anode. A direct current 508 is applied to the electrodes thereby driving the reduction of oxygen at the cathode to produce hydrogen peroxide 524 and sodium hydroxide as the majority products from the cathode while water is oxidized at the anode to produce acetic acid 526 and oxygen gas as majority products from the anode.

In this example, the cathode product solution has a composition of approximately 6 g/L hydrogen peroxide (as $H_2O_2$), 4 g/L sodium acetate and a pH of about 12.4 (as NaOH) assuming a 94% current efficiency for oxygen reduction to hydrogen peroxide. The anode product solution has a composition of approximately 31 g/L acetic acid and 7/5 g/L sodium acetate assuming an 85% sodium acetate to acetic acid conversion. The anode product solution volume is about 0.46 L per 1 L of cathode product solution.

The alkaline hydrogen peroxide cathode product solution is mixed and reacted with an acyl or acetyl donor 510, for example, triacetin in a ratio 25.5 g triacetin per 1 liter of alkaline hydrogen peroxide solution 524. The resulting concentrate will contain approximately 13 g/L peroxyacetic acid 524' and 0.17 g/L hydrogen peroxide assuming 97% conversion of the hydrogen peroxide to peroxyacetic acid. The concentrate will also contain about 11 g/L glycerol byproduct 528.

In the present example, the above peroxyacetic acid concentrate 524' is diluted to 1.5 g/L, a dilution factor of 8.7 times. Dilution is achieved by diluting the acidic anode product solution with 7.24 L of water 502(2) (fresh water or salt water). Additional additives 512 are also added, such as sodium or calcium chloride, tetrasodium pyrophosphate, sodium lauryl sulfate, and glycerol. The solution is then combined with acid concentrate 526 to produce a singlet oxygen reactive oxygen species output 522 with a pH in the range of pH 8 and pH 9.

For the above exemplary singlet oxygen precursor formulation the hydrogen peroxide stock solution, alkali types, and acid types and other additives including salts, surfactants, co-solvents, stabilizers, and emulsifiers can be substituted with compatible alternatives known in the art to accommodate specific application requirements. The resulting singlet oxygen reactive oxygen species 522 may then be used in the form of a liquid, an ice, a foam, an emulsion, a microemulsion or an aerosol applied by means such as injection, flooding, spraying, circulation or by any other means of conveying a fluid.

The above example 6 may also be implemented using the system of FIG. 9 and method of FIG. 10, without diluting the peroxyacetic acid concentrate 524'.

Example 7

Electrochemical Generation of $H_2O_2$ as "Control" for Superoxide Production Experiments (Experiments 8-9)

A reactor system with an electrochemical reactor of FIG. 6 and fluid process flow illustrated in FIG. 7 was used in this example. A carbon fiber cathode suitable for high efficiency hydrogen peroxide production was installed in the reactor with an active superficial area of 255 $cm^2$. The anolyte reservoir and chamber were charged with a 2.5 L solution of about 1.5 M sodium hydroxide in distilled water. The anolyte was recirculated through the anode chamber over time. A ca. 93% oxygen gas stream generated by a pressure swing adsorption oxygen concentrator at about 5 L per minute was circulated through the gas feed line and reactor by a pump at a rate of 10 liters per minute at 2.6 psig while a 5 L per minute bleed stream of oxygen gas was released from the system. The catholyte was a 0.05 M solution of sodium sulfate in distilled water adjusted to pH 11.2 with sodium hydroxide to precipitate trace magnesium in the electrolyte. The catholyte solution was fed into the catholyte feed line at a rate of 12.8 mL per minute at 1.3 psig (single pass, flow through). A DC current was applied to the reactor at 5.0 amps (current control). The negative pole of the power supply was grounded. Hydrogen peroxide concentration was analyzed by titration using the Hach Inc. HYP-1 Hydrogen Peroxide Test and pH was measured using an Oakton pH 11 Series meter with a temperature compensated double junction pH electrode.

The catholyte output reached a steady state composition of 3700+/−50 mg/L hydrogen peroxide and pH 12.25+/−0.04 at 25 to 26° C. The current efficiency for hydrogen peroxide production was calculated to be 90.8% assuming a two electron reduction of molecular oxygen.

Example 8

Superoxide Generation Using Electrochemical Reactor

A generation system from FIG. 11 and associated method from FIG. 12 was used in the present example to show an exemplar of producing a superoxide precursor formulation using an electrochemical generator, in one embodiment. Superoxide concentrate 1124 and, optionally, acid concentrate 1126 are electrochemically generated using an electrochemical reactor 1114. Electrochemical reduction of oxygen is conducted at a suitable cathode and water is oxidized at a suitable anode in an electrochemical reactor 1114 in which the anode and cathode chambers are separated by a membrane. Oxygen gas 1106 and a 4 g/L aqueous sodium acetate solution 1104 are supplied to the cathode while a 50 g/L aqueous sodium acetate solution 1104 is supplied to the anode. A direct current 1108 is applied to the electrodes thereby driving the reduction of oxygen at the cathode to produce superoxide, hydrogen peroxide and sodium hydroxide as the majority products 1124 of the cathode, while water is oxidized at the anode to produce acetic acid and oxygen gas as the majority products 1126 of the anode.

In this example the cathode product solution 1124 has a composition of approximately 3.0 g/L superoxide (as $O_2.^-$), 3.2 g/L hydrogen peroxide (as $H_2O_2$), 4 g/L sodium acetate and a pH of about 12.2 (as NaOH) assuming a 90% current efficiency for oxygen reduction to superoxide and hydrogen peroxide. The anode product solution 1126 has a composition of approximately 31 g/L acetic acid and 7.5 g/L sodium acetate assuming 85% sodium acetate to acetic acid conversion. The anode product solution volume is about 0.46 L per 1 L of cathode product solution.

The superoxide-containing cathode product solution 1124 is then diluted to its point of use concentration before or during pH adjustment to minimize losses resulting from accelerated superoxide decomposition at lower pH. In this example the superoxide is diluted to 1.0 g/L, a dilution factor of 3 times. In one example, dilution can be achieved by diluting the acidic anode product solution with 1.54 L of water (fresh water or salt water), adding other desirable additives to the diluted anode product solution and then combining the diluted anode product solution with the superoxide-containing cathode product solution. Examples of additives include sodium chloride, sodium lauryl sulfate, isopropanol and soybean oil.

Due to the decreasing lifetime of superoxide in aqueous media as the pH becomes less alkaline, non-aqueous co-solvents or emulsion compositions may be employed to improve the lifetime and activity of superoxide solution 1124. Alternatively, the alkaline superoxide-containing cathode product solution may be utilized directly, followed by pH neutralization or adjustment with the acidic anode product solution.

For the above formulation the hydrogen peroxide stock solution, alkali types, and acid types and other additives including salts, surfactants, co-solvents, stabilizers, and emulsifiers can be substituted with compatible alternatives known in the art to accommodate specific application requirements. The resulting singlet oxygen reactive oxygen species 1122 may then be used in the form of a liquid, an ice, a foam, an emulsion, a microemulsion or an aerosol applied by means such as injection, flooding, spraying, circulation or by any other means of conveying a fluid. The above example may also be implemented without diluting the superoxide solution 1124.

Example 9

Dye Oxidation with Singlet Oxygen

Methylene blue (MB) is a heterocyclic aromatic compound with the molecular formula $C_{16}H_{18}N_2SCl$ and is considerably resistant to oxidation. MB is a useful model dye for comparing the oxidative strengths of various oxidizers based on the rate of color loss from solutions when treated. Methylene blue dissolved in water has an intense absorption band maximum near 662 nm in the visible part of the electromagnetic spectrum resulting in its intense blue color. Observing the loss of this absorption and blue color by oxidation of the dye provides a preliminary comparison between oxidizers.

A series of MB oxidation trials were conducted near room temperature (17-22° C.) by combining equal volumes of oxidant formulations with 100 mg/L MB stock solution resulting in a 50 mg/L MB initial concentration. The change in MB solution color was evaluated over time by visual comparison to a series of color standards made by serial dilution of the same 100 mg/LMB stock solution. Color standards were 50, 25, 10, 5, 1, and 0.5 mg/L MB. Color comparisons were made with test samples and color standards contained in 12 mm inner diameter Pyrex test tubes positioned in front of a back-lit, diffuse white field. Solution pH and temperature was measured with a temperature compensated pH electrode using an Oakton pH11 meter with three point calibration. Hydrogen peroxide concentration was measured using the HACH hydrogen peroxide test method based on the ammonium molybdate-catalyzed tri-iodide titration with sodium thiosulfate.

The following bulk chemical reagents were purchased and used as received: Triacetin, 99%, bought from Acros Organics; Methylene Blue, 1% w/v aqueous solution bought from Ricca Chemical Company; Hydrogen peroxide, 2.7% w/v (measured) bought from Kroger Co.; Sodium Hydroxide, 100% bought from Rooto Corp.; Sodium Sulfate, 100% anhydrous bought from Duda Diesel; and Distilled water from Kroger Co.

For example, electrochemically generated hydrogen peroxide concentrate solution was produced one to three days prior to use and stored at 2-4° C. in a high density polyethylene bottle. The composition of the electrochemically generated hydrogen peroxide solution in distilled water at room temperature was 4800 mg/L (+/−50 mg/L) hydrogen peroxide, pH 12.81 (+/−0.04) as sodium hydroxide, and 7.1 g/L sodium sulfate. Hydrogen peroxide concentration was stable for several days.

Electrochemically co-generated sulfate acid concentrate with pH 1.40 (+/−0.04) was produced from a 0.31 M (44.0 g/L) sodium sulfate brine in distilled water. The approximate calculated composition of the acid concentrate at 20° C. (pKa 0.973) was 0.091 M sodium sulfate and 0.24 M sodium bisulfate.

Peroxyacetic acid formulations were made by mixing electrochemically generated hydrogen peroxide solution with tiacetin as the acetyl donor. The molar ratios of hydrogen peroxide:acetyl donor group was adjusted to produce non-equilibrium perxyacetic acid solutions. The triacetin molecule possesses three molar equivalents of acetyl groups. A 2.00 mL volume of the oxidant formulation was combined with 2.00 mL of 100 mg/L MB aqueous solution. The initial pH was then adjusted by quickly titrating in electrochemically generated sulfate acid concentrate in amounts less than 0.5-2% of the total solution volume. The initial concentration of peroxyacetic acid was estimated based on the initial hydrogen peroxide concentration. The amount of unreacted hydrogen peroxide residual was not measured, but its effect was observed in the percent color removal results.

Table 1 below represents examples of MB oxidation test results demonstrating the relative effects of oxidant, pH, concentration and molar ratio of acetyl donor groups reacted with hydrogen peroxide. The initial MB concentration was 50 mg/L in all cases. Entry 1 used commercially produced hydrogen peroxide as the parent oxidant near neutral pH without adjustment. Entry 2 used electrochemically generated hydrogen peroxide at high strength without pH adjustment. Entry 3 used commercially produced hydrogen peroxide which was reacted with triacetin near pH 12.2, a known amount of hydrogen peroxide was added and then pH was adjusted with electrochemically generated sulfate acid concentrate. Entries 4-13 used electrochemically generated hydrogen peroxide reacted with triacetin and diluted to varying initial concentrations of peroxyacetic acid as the parent oxidant.

TABLE 1

MB Oxidation Test Results

| Entry no. | Molar reaction ratio, HP:acetyl equiv. | Initial Conc., Parent Oxidant | Initial pH | Final pH | Final Time (h) | % Color Removal |
|---|---|---|---|---|---|---|
| 1 | 1:0 | 50 mg/L, HP | 6.1-6.4 | NR | 3 | 0 |
| 2 | 1:0 | 2150 mg/L, HP | 12.0-12.2 | NR | 3 | 0 |
| 3 | 1:2 | 7000 mg/L, PAA 5000 mg/L, HP | 9.00 | NR | 48 | <10 |
| 4 | 1:1 | <240 mg/L, PAA | 3.54 | 3.71 | 7 | 0 |
| 5 | 1:1 | <240 mg/L, PAA | 8.55 | 6.93 | 7 | 25 |
| 6 | 1:2 | 240 mg/L, PAA | 4.50 | 4.55 | 8 | 0 |
| 7 | 1:2 | 240 mg/L, PAA | 9.00 | 7.90 | 8 | 65 |
| 8 | 1:4 | 240 mg/L, PAA | 4.60 | 4.73 | 7 | 0 |
| 9 | 1:4 | 240 mg/L, PAA | 8.49 | 7.75 | 7 | 50 |
| 10 | 1:2 | 465 mg/L, PAA | 3.97 | 3.70 | 7 | 20 |
| 11 | 1:2 | 465 mg/L, PAA | 9.01 | 7.99 | 7 | 82 |
| 12 | 1:2 | 950 mg/L, PAA | 9.01 | 8.16 | 7 | 93 |
| 13 | 1:2 | 1900 mg/L, PAA | 9.00 | 8.46 | 5 | 99.5 |

HP = hydrogen peroxide;
PAA = peroxyacetic acid;
NR = not recorded

The above results demonstrate, for example, that singlet oxygen evolving formulations are significantly stronger oxidants than hydrogen peroxide or peroxyacetic acid solutions alone. Hydrogen peroxide by itself did not have any observed effects during this test and after the test solution in Entry 1 had sat for several days. Alkaline hydrogen peroxide in Entry 2 eventually caused a small amount of MB to precipitate after several hours more and has a slight shift in solution color to ta purple hue, but color loss did not progress significantly. A control test with 50 mg/L MB without any oxidant, but in the presence of 1 M sodium hydroxide gave a similar result to Entry 2 indicating that hydrogen peroxide had little or no effect on the observed changes. Entry 3 demonstrates that the presence of a significant concentration of hydrogen peroxide in the peroxyacetic acid formulation severely inhibits oxidative activity toward MB and color removal.

Entries 5, 7 and 9 in Table 1, above, demonstrate the effect of HP:acetyl donor equivalent ratio on oxidation activity as impacted by hydrogen peroxide residual, which leads to inhibited oxidative activity presumably due to singlet oxygen quenching. When the HP:acetyl donor equivalent ratio is 1:1 the MB color loss is significantly lower than when the ratio is 1:2 or 1:4. The difference in results between HP:acetyl donor equivalent ratios of 1:2 and 1:4 is minimal when normalized to reaction time indicating that an excess of acetyl donor is not necessarily detrimental to oxidative activity.

Figure 13:
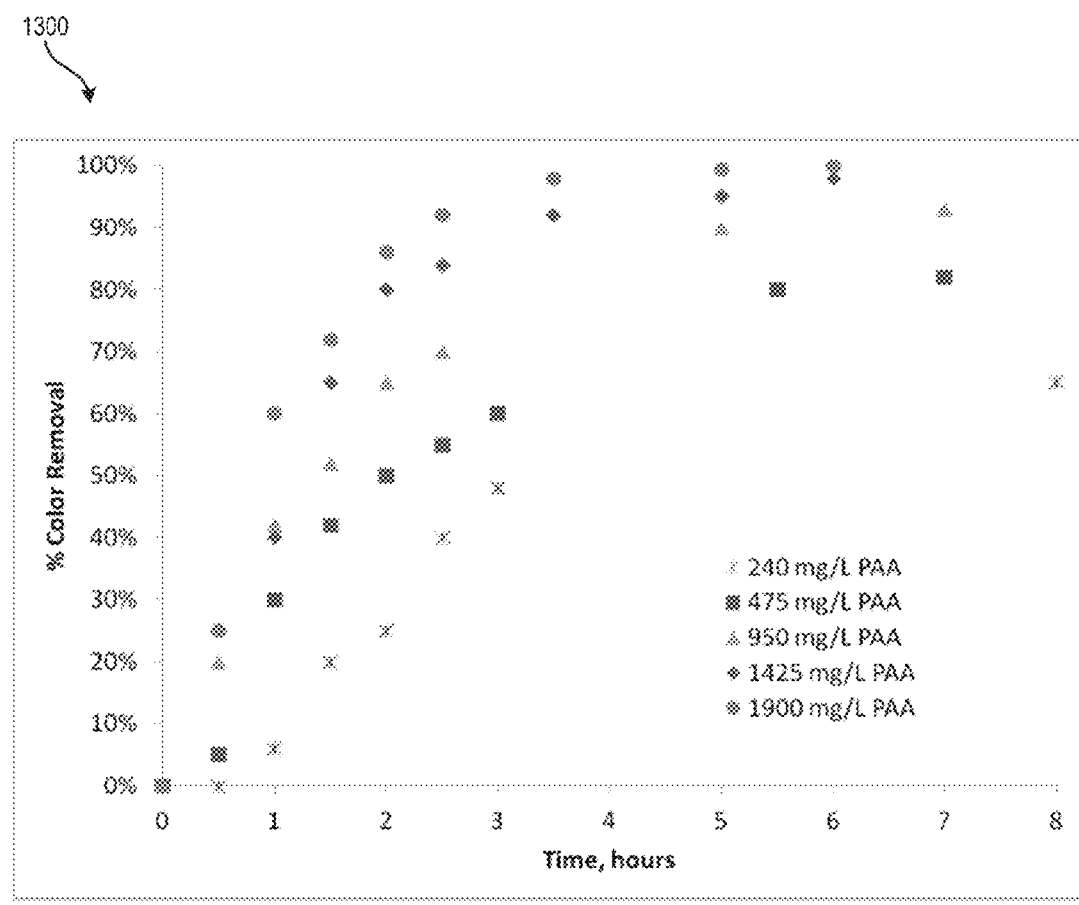
FIG. 13 shows exemplary results of the percent color removal of 50 mg/L MB solutions observed over time starting with different initial peroxyacetic acid concentrations.

When the initial peroxyacetic acid solution pH was above 8 in Table 1, above, the oxidation and color loss of MB was observed. When the initial peroxyacetic acid solution pH was below 5 there was little to no color loss observed. When the pH remained above approximately 6.5 an increase in the peroxyacetic acid concentration resulted in faster and greater color loss of MB. This trend is demonstrated by the results in graph 1300 of FIG. 13 showing the percent color removal of 50 mg/L MB solutions observed over time starting with different initial peroxyacetic acid concentrations. The results in graph 1300 of FIG. 13 also demonstrate that the singlet oxygen evolution occurs over a period of several hours. This result is reinforced by the observation of gas bubble evolution, which persists for several hours when the initial peroxyacetic acid concentrations are significantly greater than 1900 mg/L.

Example 10 pH Control and Formulation of Nitrate Oxidation Byproduct

As materials are oxidized and the peroxyacetic acid transforms to acetic acid the pH of the treatment solutions decreases. The initial pH and/or pH buffer concentration of the singlet oxygen precursor solutions should be adjusted to control the change in pH during the active oxidation period such that the final pH is in a desirable range. Table 2 below shows oxidation results for the raw hydraulic fracturing and flowback water with singlet oxygen precursor formulations. Data Table 2, below, demonstrates how the initial pH and amount of parent oxidant and amount of oxidation can be used control the final pH of the oxidized water. This example also illustrates the production of nitrate as a byproduct of oxidation of nitrogen-containing organic materials with singlet oxygen formulations.

TABLE 2

Oxidation Results For Raw Hydraulic Fracturing and Flowback Water

| Sample No. | PAA:TOC mass ratio | Raw water volume (mL) | Total oxidation volume (mL) | Initial oxidation pH | Final (6 h) oxidation pH | Nitrate byproduct (mg/L) |
|---|---|---|---|---|---|---|
| 1 | 0:1 | 37 | 56.7 | 8.19 | 8.19 | BDL |
| 2 | 2.4:1 | 37 | 56.7 | 8.87 | 6.73 | 0.92 |
| 3 | 1.2:1 | 37 | 56.7 | 8.77 | 6.81 | 0.52 |
| 4 | 0.6:1 | 37 | 56.7 | 8.67 | 7.00 | 0.31 |

BDL = below detection limit of 0.1 mg/L

Raw hydraulic fracturing and flowback water generated by oil and gas development operations was obtained from an undisclosed location in Colorado, USA after temporary impoundment in a lagoon. The composition of the raw water was approximately 5000 mg/L total organic carbon (hereinafter "TOC"), approximately 10,000 mg/L total dissolved solids (hereinafter "TDS"), appeared opaque with suspended silt and dark brown organic material and had a pH of 8.19 indicating alkalinity content. The raw water also possessed a mild odor of volatile organic compounds (i.e., petrochemicals).

Singlet oxygen formulation concentrate, formulated by the above embodiments, was added to the raw water in varying amounts with distilled water added to maintain equivalent dilutions between samples. The approximate mass ratios of peroxyacetic acid to TOC are reported in Table 2, above, to distinguish singlet oxygen precursor doses. The singlet oxygen precursor formulation was made by mixing and reacting 1.40 mL triacetin with 16.3 mL of a 1% w/v hydrogen peroxide stock solution adjusted to pH 12.40 with NaOH. The resulting peroxyacetic acid solution concentrate was adjusted to pH 8.9 with about 2.0 mL of electrochemically generated sulfate acid concentrate of pH 1.32. The samples in Table 2, above, were prepared by mixing 37 mL of raw water with: 19.7 mL of distilled water for control sample no. 1; 19.7 mL of singlet oxygen precursor formulation for sample no. 2; 9.8 mL of singlet oxygen precursor formulation plus 9.8 mL distilled water for sample no. 3; 4.9 mL of singlet oxygen precursor formulation plus 14.8 mL distilled water for sample no. 4. The samples were each contained in 100 mL glass jars at room temperature.

The initial pH was measured immediately after sample preparation. The initial pH was affected by the amount of singlet oxygen precursor formulation added to the sample. Samples containing singlet oxygen precursor formulation evolved gas rapidly enough to effervesce for 1-2 hours. Effervescence also served as an effective mixing mechanism. Within the first 30 minutes of oxidation the color of sample no's 2-4 had become paler than the control sample no. 1. After 5-6 hours visible gas evolution had subsided and the oxidized samples were a significantly paler tan color than the control. Sample no. 2 was the palest in color corresponding with the greatest singlet oxygen precursor dose.

The final pH was measured at 6 hours. Higher initial singlet oxygen precursor formulation concentration led to lower final pH. Oxidized samples had a final pH of 6.7 to 7.0 demonstrating the potential to balance pH with the singlet oxygen precursor formulation and dose. The precursor formulation used in this example contained acetate and acetic acid which can act as a pH buffer and reduce alkalinity, respectively. As oxidation proceeded, additional acetic acid (the byproduct from peroxyacetic acid reactions) and potentially partial oxidation products with carboxylic acid groups accumulated leading to a decrease in pH over time.

Nitrate was found to be an oxidation byproduct of the organic material in the hydraulic fracturing flowback water. Results of ion chromatography analysis of the samples in Table 2, above, corrected for dilution, show that byproduct nitrate content was proportional to singlet oxygen precursor formulation concentration. Nitrogen-containing materials such as natural organic materials were oxidized enough to liberate nitrogen as nitrate. Nitrate was not detected in the non-oxidized raw water.

In view of the many possible embodiments to which the principles of the disclosure may be applied, it should be recognized that the embodiments herein should not be taken as limiting the scope of the present disclosure.

Example 11

Electrochemical Co-Generation of Hydrogen Peroxide and Superoxide

A reactor system with an electrochemical reactor of FIG. 6 and fluid process flow illustrated in FIG. 7 was used in this example. A carbon fiber cathode suitable for combined hydrogen peroxide and superoxide production was installed in the reactor with an active superficial area of 255 cm$^2$. The anolyte reservoir and chamber were charged with a 2.5 L solution of about 1.5 M sodium hydroxide in distilled water. The anolyte was recirculated through the anode chamber over time. A ca. 93% oxygen gas stream generated by a pressure swing adsorption oxygen concentrator at 5 L per minute was circulated through the gas feed line and reactor by a pump at a rate of 9.0 liters per minute at 3.0 psig while a 5 L per minute bleed stream of oxygen gas was released from the system. The catholyte was a 0.05 M solution of sodium sulfate in distilled water adjusted to pH 11.2 with sodium hydroxide to precipitate trace magnesium in the electrolyte. The catholyte solution was fed into the catholyte feed line at a rate of 12.8 mL per minute at 1.6 psig (single pass, flow through). A DC current was applied to the reactor at either 5.0 amps or 8.0 amps (current control). The negative pole of the power supply was grounded. Hydrogen peroxide concentration was analyzed by titration using the Hach Inc. HYP-1 Hydrogen Peroxide Test and pH was measured using an Oakton pH 11 Series meter with a temperature compensated double junction pH electrode.

At 5.0 amps operating current the catholyte output reached a steady state composition of 2000+/−50 mg/L hydrogen peroxide and pH 12.20+/−0.04 at 25 to 27° C. The current efficiency for hydrogen peroxide production was calculated to be 48.4% assuming a two electron reduction of molecular oxygen. A maximum potential concentration of superoxide anion produced was calculated to be 3400 mg/L assuming 90% of the balance of the applied current caused the one electron reduction of molecular oxygen.

At 8.0 amps operating current the catholyte output reached a steady state composition of 2500+/−50 mg/L hydrogen peroxide at 27 to 28° C. and pH 12.58+/−0.04 measured at a 10-fold dilution to adjust the pH to within the accurate range of the pH probe. The current efficiency for hydrogen peroxide production was calculated to be 37.8% assuming a two electron reduction of molecular oxygen. A maximum potential concentration of superoxide anion produced was calculated to be 6800 mg/L assuming 90% of the balance of the applied current caused the one electron reduction of molecular oxygen.

Analysis of Electrochemically Generated Hydrogen Peroxide and Superoxide (Examples 7 and 11):

Catholyte outputs from Examples 7 and 11 above were analyzed by ultraviolet-visible absorption spectroscopy between 21 and 24° C. Data was collected using an Ocean Optics USB4000-UV-VIS absorbance system (200-850 nm) with SpectraSuite software. Disposable 1 cm Plastibrand disposable macro cuvettes were used with a 220 nm cutoff. Hydrogen peroxide concentration was analyzed by titration using the Hach Inc. HYP-1 Hydrogen Peroxide Test and pH was measured using an Oakton pH 11 Series meter with a temperature compensated double junction pH electrode. All samples were diluted with distilled water to 100 mg/L hydrogen peroxide and pH adjustments were made using sodium hydroxide or pH 1.40 sodium bisulfate solution.

Hydrogen peroxide UV standards were made from 3% topical hydrogen peroxide and sodium hydroxide combined in distilled water. Standards included 100 mg/L hydrogen peroxide at pH 6.7, 10.0, 11.0 and 12.0. Standards were also made with 0.10 mol/L NaOH (nominally pH 13) and 1.0 mol/L NaOH (nominally pH 14) measured by weight of sodium hydroxide dissolved in distilled water at room temperature.

The previously reported absorption band maximum for dilute aqueous superoxide generated by radiolysis of dissolved oxygen in the presence of sodium formate and ethylenediaminetetraacetic acid at pH 10.5 was 245 nm. See "Reactivity of $HO_2/O_2^-$ Radicals in Aqueous Solution," Beilski, et al., *J. Phys. Chem. Ref. Data*, Vol. 14, No. 4, 1985. The reported absorption band maximum for dilute hydroperoxyl radical ($HO_2.$) in aqueous perchloric acid at pH 1.5 was 225 nm.

Figure 14A:
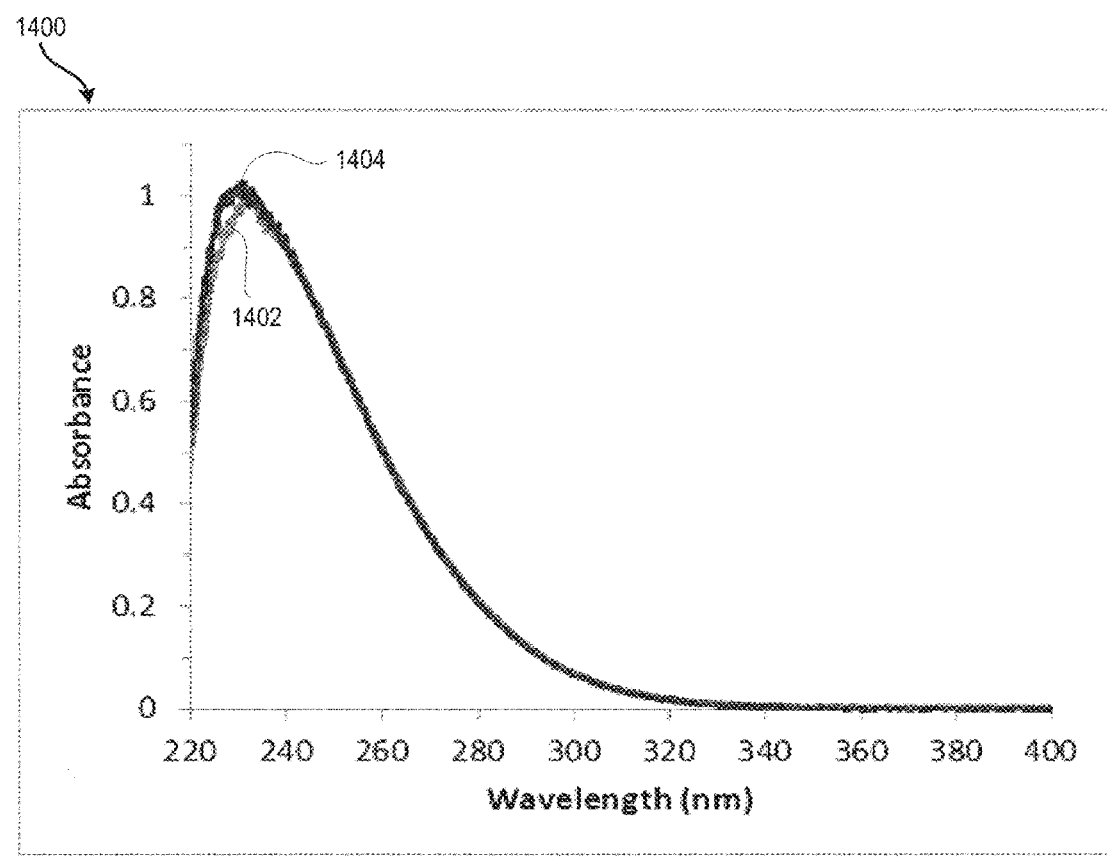
FIG. 14A shows graph 1400 that shows the full spectra of samples diluted to 100+/−4 mg/L hydrogen peroxide and adjusted to pH 12.00+/−0.04.

FIGS. 14A/B shows graphs 1400, 1450 that compares the UV absorbance spectra of fresh catholyte outputs, within 2 minutes of production, of the high efficiency hydrogen peroxide output 1402 in Example 7, and the co-generated hydrogen peroxide and superoxide output 1404 in Example 11. Both outputs were produced at 5 amps.

Figure 14B:
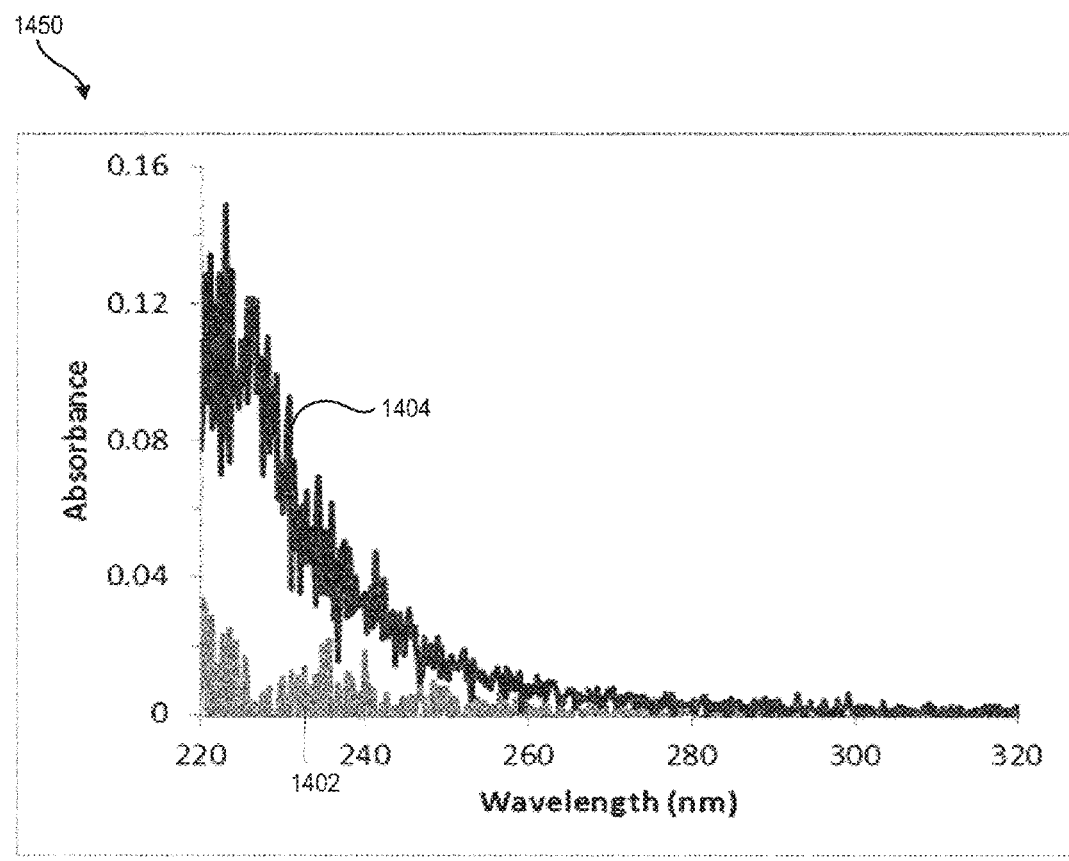
FIG. 14B shows the spectra of FIG. 14A with hydrogen peroxide absorbance subtracted off.

FIG. 14A shows graph 1400 that shows the full spectra of samples diluted to 100+/−4 mg/L hydrogen peroxide and adjusted to pH 12.00+/−0.04 and graph 1450 of FIG. 14B shows the same spectra with hydrogen peroxide absorbance subtracted off. The co-generated hydrogen peroxide and superoxide output exhibits additional absorbance intensity on the shorter wavelength side of the hydrogen peroxide band and a weak absorbance band in the subtracted spectrum. The high efficiency hydrogen peroxide output did not exhibit a second absorbance band after subtracting off the hydrogen peroxide absorbance. Hydrogen peroxide at 100+/−4 mg/L and pH 12.0 has an absorbance maximum near 232 nm while the weak absorbance band of the co-generated hydrogen peroxide and superoxide output is shifted to shorter wavelength.

The weak absorbance band of the co-generated hydrogen peroxide and superoxide output increases in intensity over time at pH 12, which is behavior not observed for alkaline hydrogen peroxide alone.

Figure 15A:
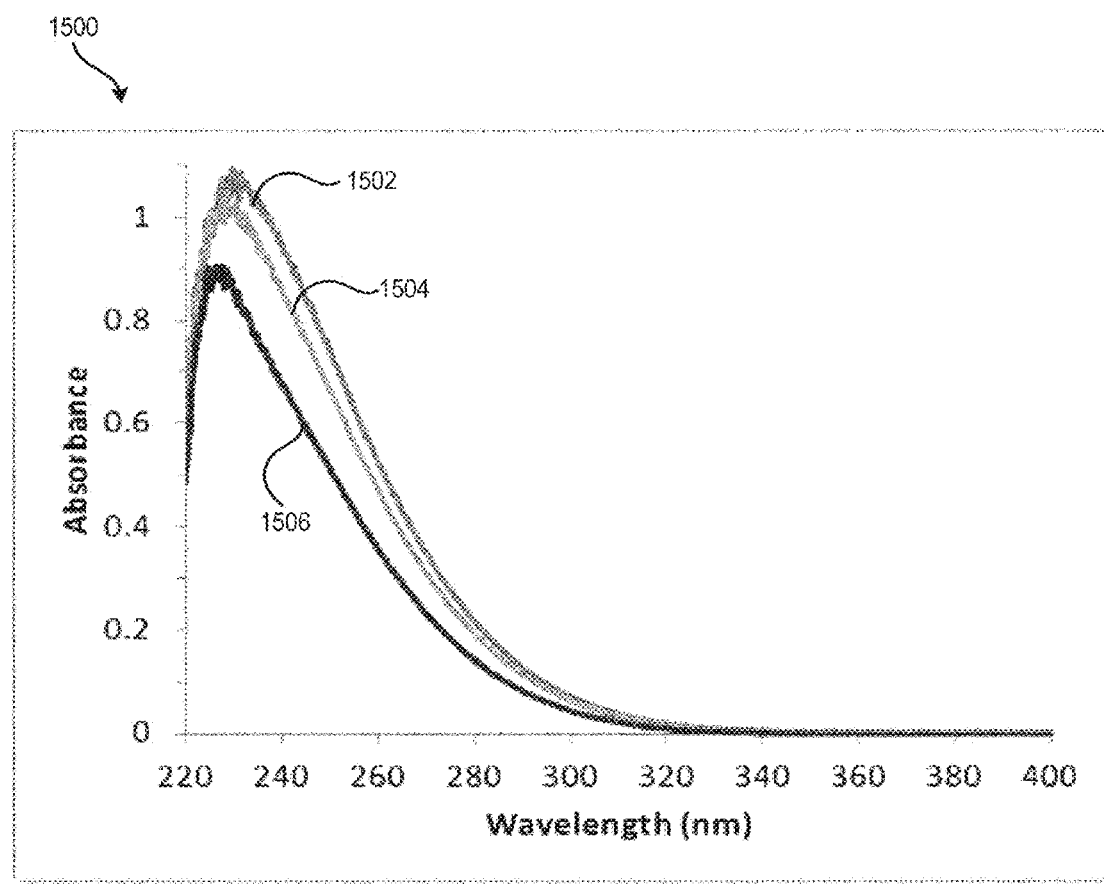
FIGS. 15A/B show graphs 1500, 1550 that show the evolution of the UV absorbance spectrum over five hours for the co-generated hydrogen peroxide and superoxide output produced at 8 amps in Example 11 diluted to 100+/−4 mg/L hydrogen peroxide, adjusted to pH 12.00+/−0.04 and analyzed over time.
Figure 15B:
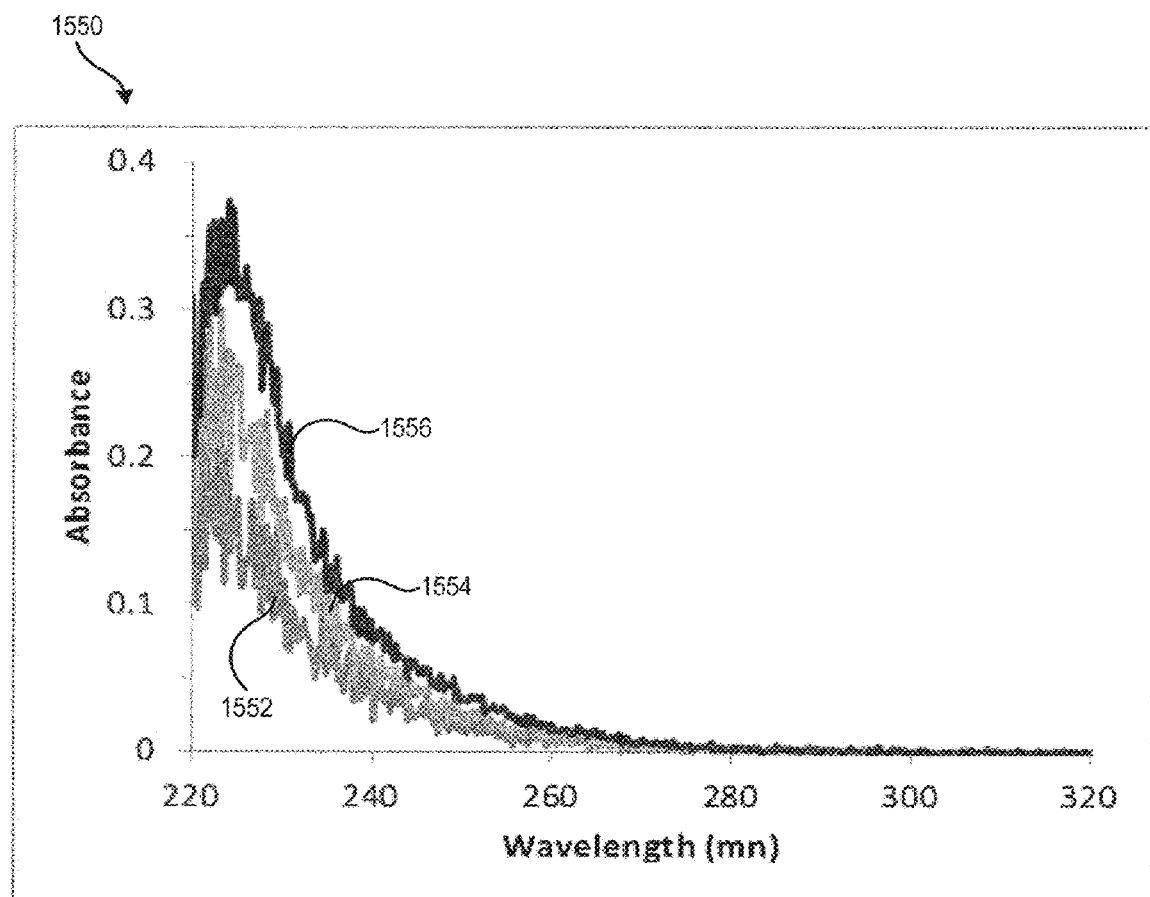

FIGS. 15A/B show graphs 1500, 1550 that show the evolution of the UV absorbance spectrum over five hours for the co-generated hydrogen peroxide and superoxide output produced at 8 amps in Example 11 diluted to 100+/−4 mg/L hydrogen peroxide, adjusted to pH 12.00+/−0.04 and analyzed over time. Graph 1500 shows the full spectra of the output including hydrogen peroxide at two minutes after production 1502, three hours after production 1504 and five hours after production 1506. Graph 1550 shows the same spectra with hydrogen peroxide absorbance subtracted off at two minutes after production 1552, three hours after production 1554, and five hours after production 1556. The growing band in graph 1550 has an absorbance maximum near 224 nm at five hours, which is consistent with the reported position of the hydroperoxyl radical. The original spectrum in graph 1500 shows an 18% decrease in absorbance and a shift in the absorbance band maximum from 230 nm, to 228 nm at three hours, to 226 nm at five hours. These spectral changes were accompanied by a decrease in pH to 11.66+/−0.04, but there was no measurable decrease in hydrogen peroxide concentration. The aforementioned behavior is consistent with the buildup of a different species with lower molar absorptivity by a slow chemical reaction or equilibrium process and a slow loss of a non-hydrogen peroxide species in the electrochemically generated output.

For comparison, the same output produced at 8 amps in Example 11, diluted to 100+/−4 mg/L hydrogen peroxide and adjusted to pH 13 (0.10 mol/L NaOH) did not exhibit any change in the 224 nm hydrogen peroxide subtracted peak intensity or hydrogen peroxide concentration over 5 hours (data not shown). The original spectra did show a 10% decline in peak intensity of the hydrogen peroxide peak near 231 nm over five hours without any wavelength shift in peak maximum position. This behavior shows a more stable output solution with a slower loss of a non-hydrogen peroxide species in the electrochemically generated output.

Figure 16A:
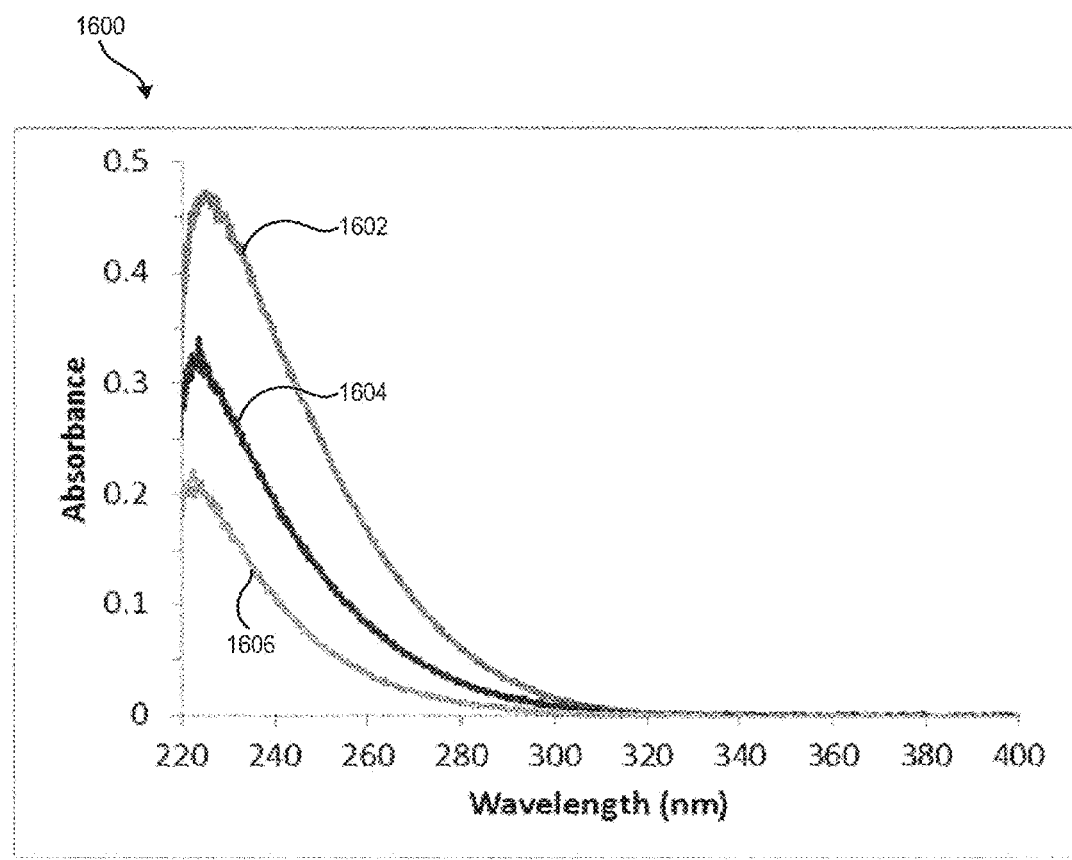
FIGS. 16A/B show graphs 1600, 1650 that shows the evolution of the UV absorbance spectrum over five hours for the co-generated hydrogen peroxide and superoxide output produced at 8 amps in Example 11 diluted to 100+/−8 mg/L hydrogen peroxide, adjusted to pH 11.04+/−0.04 and analyzed over time.
Figure 16B:
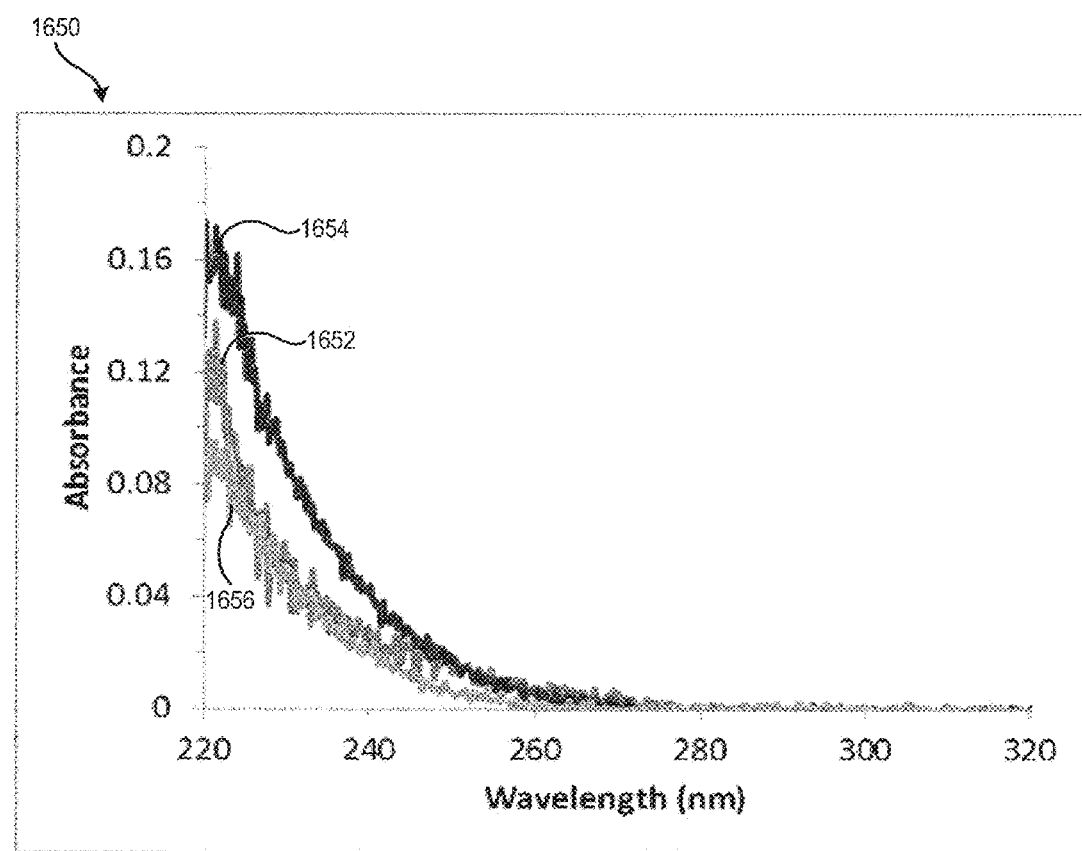

FIGS. 16A/B show graphs 1600, 1650 that shows the evolution of the UV absorbance spectrum over five hours for the co-generated hydrogen peroxide and superoxide output produced at 8 amps in Example 11 diluted to 100+/−8 mg/L hydrogen peroxide, adjusted to pH 11.04+/−0.04 and analyzed over time. Graph 1600 shows the full spectra of the output including hydrogen peroxide at two minutes after production 1602, one and a half hours after production 1604 and five hours after production 1606. Graph 1650 shows the same spectra with hydrogen peroxide absorbance subtracted off at two minutes after production 1652, one and a half hours after production 1654, and five hours after production 1656. The 221 nm band in graph 1650 increases in intensity for a period of time, then decreases in intensity. The original spectrum in graph 1600 shows a 56% decrease in absorbance and a shift in the absorbance band maximum from 225 nm to 222 nm at five hours. These spectral changes were accompanied by a decrease in pH to 9.47+/−0.04 and a 20% decrease in hydrogen peroxide concentration to 80+/−4 mg/L. Approximately 55-60% of the decrease in absorbance in graph 1600 is attributable to the decrease in pH. In graph 1650 the initial spectrum of the output shows a broad absorption shoulder in the 240 to 260 nm region, which is consistent with the absorption region for the "free" form of dilute, aqueous superoxide. This shoulder is often observed for freshly made reactor output solutions. These results show that a lower initial pH leads to a more reactive and less stable output solution including the formation of a different species with lower molar absorptivity than hydrogen peroxide; a more rapid loss of this different species involving the consumption of hydrogen peroxide; and a more rapid loss of a non-hydrogen peroxide species in the electrochemically generated output.

The UV spectra of co-generated hydrogen peroxide and superoxide outputs show that the initially generated alkaline hydrogen peroxide changes in form in the presence of superoxide, especially when the pH is near or below hydrogen peroxide's pKa of 11.6. Likewise, the "free" form of superoxide is quenched by the presence of hydrogen peroxide, especially at high concentrations. Hydrogen peroxide has been reported to behave as a stabilizing co-solvent which increases the chemical reactivity of aqueous superoxide solutions. See "Identification of the Reactive Oxygen Species Responsible for Carbon Tetrachloride Degradation in Modified Fenton's Systems," Watts, et al., *Environmental Science & Technology*, Vol. 38, No. 20, 2004. Hydrogen peroxide is a weak acid and can potentially serve as a proton source for superoxide, which has a pKa of 4.8. Based on the UV spectra it appears that hydrogen peroxide in its fully protonated form can interact with superoxide to form a different species, such as, for example, an "adduct," in an equilibrium process and/or lead to the reactions in Equations 1 and 3. At pH 11, hydrogen peroxide is consumed more rapidly, consistent with the processes in Equations 1 and 3, which produce hydroxyl radicals. A measurable increase in the concentration of hydrogen peroxide and pH over time was never observed indicating that the disproportionation reaction in Equation 6 was negligible for the reactor output.

The stability of the co-generated hydrogen peroxide and superoxide output solutions was significantly greater than the lifetimes cited earlier, 1.5 minutes at pH 11 and 41 minutes at pH 12.5 in aqueous solution. The lifetimes of active species at pH 12 and greater were at least five hours in the diluted reactor output solutions. The stability of the concentrated, undiluted output solutions was lower as evidenced by gas bubble evolution observed after approximately 30 minutes time. At pH 11 the degradation of active oxygen species was accelerated, but persisted for at least five hours in the diluted reactor output solutions. Enhanced oxidation activity, of these output solutions was demonstrated to persist for more than 12 hours at pH 11-12 in the example cited below.

Example 12

Advanced Oxidation of Methylene Blue with Electrochemically Co-Generated Hydrogen Peroxide and Superoxide Catholyte output solution was generated by the method cited in Example 11 at 5 amps operating current. Output solution contained 2500+/−50 mg/L hydrogen peroxide and a calculated maximum potential concentration of 3050 mg/L superoxide at pH 12.1. 2.0 mL of freshly generated output solution was added to 2.0 mL of 100 mg/L methylene blue solution acidified with bisulfate. The prepared oxidation test solution had an initial pH of 11.9 and contained 50 mg/L methylene blue, 1250 mg/L hydrogen peroxide, a maximum potential superoxide concentration of 1500 mg/L. Solution temperature was 25° C. The methylene blue color was evaluated over time by comparison to the series of methylene blue color standards as described in Example 9. A slight decrease in color intensity, ca. 10%, was observed after 5.6 hours had passed without a significant change in pH. The solution was colorless to the eye after 50 hours. For comparison, hydrogen peroxide alone had no visible effect on methylene blue after several days.

Example 13

Potential Singlet Oxygen Formulation for In-Situ Chemical Oxidation

Singlet oxygen may be used for remediation and decontamination of a body of soil, a geologic formation, an excavated soil, and construction or demolition debris.

The following example is a potential example of singlet oxygen formulation from bulk chemicals, formulated using the system and methods depicted in FIGS. 3 and 4, for in-situ chemical oxidation (ISCO) for remediation of soil contaminated with, for example, 60 mg/kg diesel fuel and 40 mg/kg polycyclic aromatic hydrocarbons (PAH's). The resulting singlet oxygen formulation could be used to oxidize 85-95% of the contaminants, oxygenate the soil and supply non-toxic, low molecular weight organic substrates to heterotrophic bacteria which may consume residual contaminants and their oxidation byproducts. The present example includes assumptions of a soil porosity of 20%, soil pH 8.0-8.5, soil density is 2.4 g/cm$^3$, soil type is assumed to be clayey with low vapor permeability, depth of contamination is assumed to be up to 4 meters and injection and recovery wells could be used.

Chemical feeds used in, for example, the system 300 of FIG. 3 and method 400 of FIG. 4 could include applying six soil pore volumes of oxidant formulation containing a 4:1 mass ratio of peroxyacetic acid to contaminant to set the singlet oxygen dose, and a treatment rate of 32 cubic yards per day. Chemical inputs on a 100% basis may be 24.3 lb/day hydrogen peroxide, 40.7 lb/day sodium hydroxide, 9.8 lb/day hydrochloric acid, 103.9 lb/day triacetin and 7942 gal/day water. The injection concentrations of oxidant formulation constituents may be about 800 mg/L peroxyacetic acid, <15 mg/L hydrogen peroxide, 664 mg/L glycerol, 912 mg/L sodium acetate, 238 mg/L sodium chloride and an initial solution pH of 8.5-9.5. Additional sodium chloride may be added to match the salinity of the soil if necessary. Non-toxic additives including co-solvents (e.g., triacetin, glycerol), compatible surfactants (e.g., sodium dodecyl sulfate) and stabilizers (e.g., phytic acid) may be added to enhance performance. The prepared formulation may be fed as a liquid into injection wells to infiltrate the soil at ambient temperature. A residence time of at least six hours may be expected to provide singlet oxygen generation activity, provide peroxyacetic acid reaction time with contaminants and also allow Fenton-like peroxide activation processes to occur with any reduced iron minerals present.

Recovered, spent flushing fluids may have a pH similar to that of the soil body and contain salinity, hardness (e.g., calcium/magnesium carbonate), suspended solids (e.g., iron or manganese oxides), glycerol, acetate, additives, oxidation byproducts (e.g., nitrate, low molecular weight hydrocarbons) and potentially non-oxidized contaminants and microbes. The spent flushing fluids may be treated on site for discharge, sent to a municipal water treatment facility, disposed of in an injection well, or processed for water recovery and recycle back into the remediation process or other use.

Example 14

Potential Superoxide Formulation for Ex-Situ Chemical Oxidation and Reduction for Remediation Superoxide formulations may be used for remediation and decontamination of a body of soil, a geologic formation, an excavated soil, and construction or demolition debris.

The following example shows a potential superoxide formulation for ex situ chemical oxidation for remediation of soil contaminated with, for example, 10 mg/kg non-aqueous phase liquids (NAPL) containing low volatility halogenated materials such as brominated flame retardants, dioxins, and polychlorinated biphenyls (PCB's), formulated using the system of FIG. 5, for example. The resulting superoxide formulation may be used to chemically oxidize more than 99% of the contaminants and flush residuals out of the soil. In the present example, it is assumed that there is a pH 7.0-7.5, average soil density is 2.4 g/cm$^3$, and soil type is a sand/alluvial mixture. The soil is excavated for treatment and then returned to its origin.

In the present example, chemical feeds may be assumed to include applying the equivalent of 4 soil pore volumes (20% porosity assumed) of superoxide formulation containing a 3:1 mass ratio of hydrogen peroxide to contaminant to set the superoxide dose, and a treatment rate of 32 cubic yards per day. Chemical input and output rates are calculated based on the process described for FIGS. 7 and 11, using an electrochemical reactor of type in FIG. 6. Inputs into the electrochemical generator may be 834 lb/day sodium sulfate, 218 gal/day water, 5600 L/day oxygen gas at STP and approximately 1070 kWh per day to operate the system. The reactor may produce 100 lb/day hydrogen peroxide at 40% current efficiency (produced as sodium peroxide), a maximum potential mass of 235 lb/day superoxide at about 50% current efficiency (produced as sodium superoxide), approximately 28 lb/day sodium hydroxide and, in a separate output stream, 711 lb/day sodium bisulfate. Sodium bisulfate may be used for pH adjustment of superoxide formulations and treated soil. The reactor output may be diluted with 4880 gal/day water to produce an oxidant formulation of about 90 mg/L hydrogen peroxide, up to 212 mg/L superoxide, up to 750 mg/L sodium sulfate and an initial solution pH of 10.5-11.5. A relatively low concentration of oxidants may be necessary to avoid their quenching of generated hydroxyl radicals, similar to an ultraviolet-hydrogen peroxide advanced oxidation process. Other additives such as surfactants and co-solvents may be used selectively or not at all to minimize consumption of hydroxyl radicals produced by the formulation. The prepared formulation may then be applied as a liquid to the excavated soil and allowed to contact the soil for a period of time at ambient temperature or elevated temperature. The soil may also be flushed in a second step with excess co-generated acid, sodium bisulfate not used in the formulation pH adjustment, to balance the pH of the soil if becomes elevated during treatment.

Recovered, spent soil washing fluids may be expected to have a pH similar to that of the soil and contain salinity, hardness (e.g., calcium/magnesium carbonate), additives and potentially oxidation or reduction byproducts or non-oxidized or reduced contaminants and microbes. The spent flushing fluids may be treated on site for discharge, sent to a hazardous waste facility, disposed of in an injection well, or processed for water recovery and recycle back into the remediation process or other use.

Example 15

Clean in Place (CIP) Applications for Food, Beverage, Dairy, and Biopharma Processing Equipment Cleaning Clean in place (CIP) applications involve the preparation of cleansers and sanitizer solutions and dispensing them into pipes, tanks and other processing equipment that is not disassembled for cleaning. The chemical activity of such solutions provides the cleansing and sanitizing capabilities. CIP cleansers and sanitizers are prepared in day tanks, often ranging in capacity from 50 to 500 gallons, and distributed to equipment when needed during cleaning cycles. Alkaline cleansers and oxidizing alkaline cleansers may be particularly useful for removing soils and organic residues, acids for removing scaling minerals and antimicrobial sanitizers for disinfection. The use of non-chlorine based cleansers and sanitizers may minimize corrosion of stainless steel processing equipment and to avoid chlorinated oxidation or disinfection byproducts.

Acid compatible sanitizers, such as peroxyacetic acid, may reduce the number of system cleaning flushes relative to chlorine and chlorine bleach based sanitizers, which are not compatible with acid pH of less than about pH 4 due to the release of chlorine gas. Alkaline oxidizing cleansers may be more effective at removing organic soils, proteins and fat deposits than alkali detergents alone. See U.S. Pat. No. 7,754,064, FIGS. 13-14.

Figure 17:
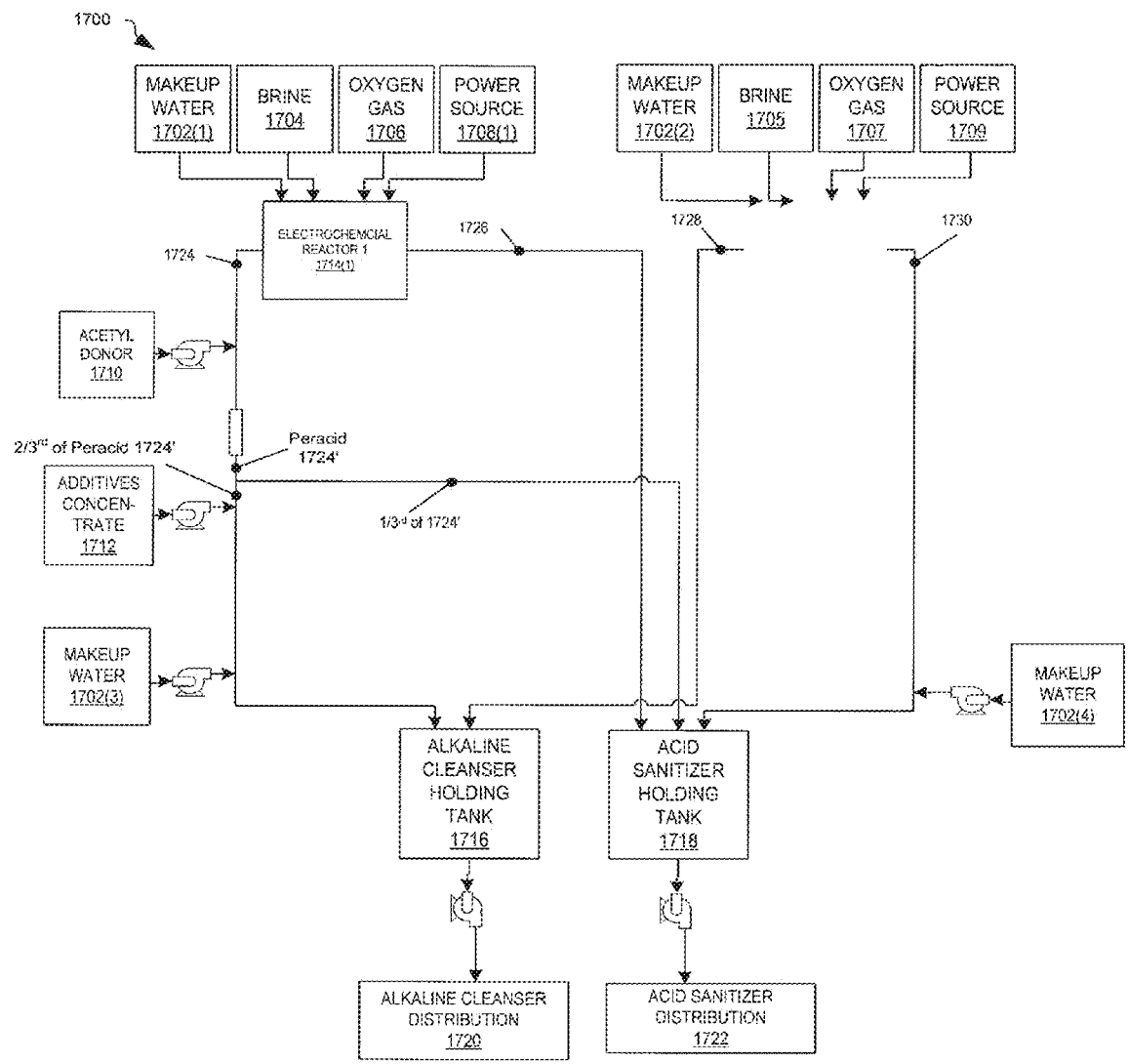
FIG. 17 shows an exemplary system and flow process for electrochemically generating a CIP cleanser, in one embodiment.

FIG. 17 shows an exemplary system and flow process for electrochemically generating a CIP cleanser, in one embodiment. The following example shows an electrochemically generated CIP cleanser and sanitizer formulations for use in food, beverage, dairy and biopharma processing equipment. Alkaline oxidizing cleanser 1720 and acid sanitizer 1722 are co-generated and stored in 500 gallon day tanks 1716, 1718, respectively until use. The alkaline oxidizing cleanser 1720 is formulated to contain 0.01 mol/L NaOH (pH 12.0) and 200 mg/L peroxyacetic acid to generate singlet oxygen, generated by method 500, for example. The acid sanitizer 1722 is formulated to contain 0.02 mol/L citric acid (pH 2.6) and 400 mg/L peroxyacetic acid, generated by, for example, the electrochemical reactor of FIG. 6. Surfactants and stabilizers may be used in either cleanser or sanitizer solution, but are not required, and not shown in FIG. 17. Cleanser solutions 1720, 1722 may be heated to 55-60° C. prior to distribution as is customary for CIP processes.

The above specified formulations use two identical electrochemical reactors, for example the electrochemical reactor discussed with reference to FIG. 6 above, with the exception of their cathode surface compositions and feed rates, in parallel to generate the required chemicals by the process outlined in FIG. 17. Electrochemical production is designed for 500 gallons each of alkaline and acid cleansers. Reactor inputs makeup water 1702, brine 1704, oxygen gas 1706, and power source 1708 and outputs 1724, 1726 are listed on a 100% basis.

Electrochemical Reactor 1714 contains an activated carbon cathode surface for high efficiency hydrogen peroxide production and produces alkaline hydrogen peroxide and citric acid concentrates in two separate output streams. Inputs for Reactor 1714 are 6.93 lb/day sodium citrate 1704, 230 L/day oxygen gas 1706 at STP, 15 gal/day water 1702(1) and approximately 9.9 kWh electricity 1708 to operate the system. Outputs for Reactor 1714 are (i) an alkaline $H_2O_2$ concentrate 1724 including 1.12 lb/day hydrogen peroxide (at 84% cathode current efficiency) combined with 0.38 lb/day sodium hydroxide and (i) an acid concentrate output 1726 including 4.53 lb/day citric acid in a separate stream. The alkaline hydrogen peroxide 1724 is reacted with 4.78 lb/day triacetin 1710 and two thirds of the resulting peroxyacetic acid solution 1724' is fed to the alkaline cleanser holding tank 1716 while the remainder is fed to the acid sanitizer holding tank 1718. Less than about 15 mg/L hydrogen peroxide is present in the peroxyacetic acid output 1724'.

Electrochemical Reactor 1715 contains a nickel cathode surface for high efficiency sodium hydroxide production and produces alkaline hydrogen peroxide 1728 and citric acid 1730 concentrates in two separate output streams. Inputs for Reactor 1715 are 17.7 lb/day sodium citrate 1705, 320 L/day oxygen gas 1707 at STP, 17 gal/day water 1702(2) and approximately 18.3 kWh electricity 1709 to operate the system. Outputs for Reactor 1715 are 1.66 lb/day sodium hydroxide 1728 (at 98% cathode current efficiency) and 11.57 lb/day citric acid 1730 in a separate stream. The sodium hydroxide 1728 is fed to the alkaline cleanser holding tank 1716 while the citric acid 1730 is fed to the acid sanitizer holding tank 1718.

The alkaline cleanser holding tank 1716 and acid sanitizer holding tanks 1718 are filled with water 1702 during chemical production bringing their final volumes to 500 gallons each. The use of triacetin 1710 to generate the peroxyacetic acid 1724' results in about 340 mg/L glycerol plus 475 mg/L sodium acetate in the alkaline cleanser and 170 mg/L glycerol plus 235 mg/L acetic acid in the acid sanitizer 1722.

In some exemplary CIP applications milder cleansers are desirable. Singlet oxygen generation is not desirable when certain materials are susceptible to degradation by singlet oxygen. Relevant examples include desalination filter membranes and polymers including polyamides, polysulfone, polyurethane, polyetheylene terephthalate, epoxy resins, polyacrylonitrile-butadiene copolymer (nitrile rubber) and natural rubber. To quench singlet oxygen generation by the alkaline cleanser solution described in the above CIP example a lower amount of triacetin 1710 is used thereby leaving a hydrogen peroxide concentration, in combination with peracid solution 1724', high enough to quench singlet oxygen evolved by peroxyacetic acid. For example, the triacetin input 1710 may be decreased by 67% to about 1.63 lb/day thereby increasing the hydrogen peroxide concentration to about 100 mg/L and decreasing the peroxyacetic acid concentration to about 200 mg/L in the alkaline cleanser solution 1720. As a result the acid sanitizing solution 1722 will contain about 50 mg/L hydrogen peroxide and 100 mg/L peroxyacetic acid. The alkali and acid concentrations remain virtually unchanged unless their production by Electrochemical reactor 1715 is decreased.

Example 16

Singlet Oxygen Production Using Bulk Chemicals for Oil Production Well Flushing Applications Well casings and pipelines are serviced to remove bacterial growth, slime buildup, mineral scale deposits, corrosion and contamination. These issues are common between oil and gas production wells and pipelines, groundwater wells, raw water and wastewater pipelines and potable water and greywater distribution systems. Microbial control, removal of slime (the decaying remains of dead bacteria and other organic materials), microbial corrosion control and scale removal are significant maintenance issues for prolonging the production capacity and lifetime of a well. Pipelines carrying raw water, wastewater, produced water, greywater and other untreated water will encounter microbial growth and slime formation and will require cleaning. Methods for cleaning well bore casings and pipelines include chemical flushing with oxidizers and acids and mechanical cleaning such as brushing and scraping.

Compatibility of oxidants with seawater and brackish water is desirable in locations where there are no natural freshwater resources available. Flushing solution activity should persist for at least 5 hours and be effective in the range of pH 8-9. Ideally flushing solutions should be pH balanced and be safe for municipal disposal or discharge.

The following example presents an application of chemical flushing of an oil production well with a singlet oxygen formulation made from bulk chemicals. The singlet oxygen formulation may be created using method 400 and system 300 discussed above. In the following example, the production well may be located in a coastal region where seawater is used as floodwater for enhanced oil recovery. The well depth may be assumed to be 12,000 feet below surface and may have an average casing diameter of 6 inches and volume of about 4,630 gallons.

In this example, chemical inputs and outputs are stated as quantities per well volume. Chemical inputs on a 100% basis may be 5.4 lb hydrogen peroxide, 8.9 lb sodium hydroxide, 2.2 lb hydrochloric acid, 22.8 lb triacetin, 9.6 lb nonionic polyether alcohol surfactant/wetting agent and 4630 gal water of which the majority (e.g., >90%) may be seawater filtered through a 1 micron rated filter. The prepared injection concentrations of oxidant formulation constituents may be about 300 mg/L peroxyacetic acid, <10 mg/L hydrogen peroxide, 250 mg/L glycerol, 340 mg/L sodium acetate, 250 mg/L surfactant/wetting agent, 90 mg/L sodium chloride (not including the salt added by seawater) and an initial pH of 8.5-9.5. An oxidant-compatible corrosion inhibitor such as tetrasodium pyrophosphate may also be added to enhance performance.

The above prepared formulation may be fed as a liquid into a well bore (or pipeline) at ambient temperature. A residence time of at least four to six hours may be expected to provide singlet oxygen generation activity and oxidative breakdown of organic materials; provide peroxyacetic acid contact time with microbes; and allow Fenton-like peroxide activation processes to occur with catalytically active reduced iron surfaces or other metal surfaces present.

The use of seawater, with a natural bromide content of about 65 mg/L, as the primary water source for the flushing solution may be expected to provide some hypobromous acid or hypobromite ion by oxidation of bromide by peroxyacetic acid. Hypobromous acid may be an additional oxidant that can participate in the performance of the singlet oxygen flushing solution and has significant oxidation and antimicrobial activity up to about pH 8.5.

Recovered, spent flushing fluids may be expected to have a pH similar to that of seawater or groundwater and contain salinity, hardness (e.g., calcium/magnesium carbonate), suspended solids (e.g., iron or manganese oxides), suspended organic materials such as slime deposits, glycerol, acetate, surfactant and corrosion inhibitor additives, oxidation byproducts (e.g., nitrate, low molecular weight hydrocarbons) and potentially non-oxidized contaminants and microbes. The spent flushing fluids may be treated on site for discharge, sent to a municipal water treatment facility, disposed of in an injection well, or processed for water recovery and recycle back into well operations.

Example 17

Potential Superoxide Formulation for Oil Sand Tailing Pond Water Treatment

Oil Sand Tailing Ponds in northern Alberta, Canada represent a very large impoundment of contaminated and toxic water created by bitumen extraction and processing. Water quality has been degraded through multiple reuse cycles to the point that it is no longer suitable for reuse. Natural biodegradation and attenuation of contaminants can be extremely slow or ineffective for remediating these waters due to the presence of recalcitrant organic contaminants such as naphthenic acids, phenols and polycyclic aromatic hydrocarbons and cold temperatures. A representative composition of tailing pond water for this treatment example can include 2000 mg/L inorganic TDS, pH 8.3, 0.025 mg/L cyanide, 50 mg/L naphthenic acids, 10 mg/L oil and grease, 0.5 mg/L phenols, 0.01 mg/L polycyclic aromatic hydrocarbons, and several trace metals such as iron (2 mg/L), copper (0.05 mg/L), chromium (0.01 mg/L), and lead (0.1 mg/L) to name a few.

The general treatment strategy is to oxidize recalcitrant organic contaminants with a superoxide and hydrogen peroxide formulation to allow for more rapid treatment of smaller organic fragments downstream in a biological treatment process. Oxidation is primarily provided by hydroxyl radicals formed directly by superoxide and hydrogen peroxide by the reactions in Equations [4] and [6]. Hydroxyl radicals are also expected to be formed by Fenton chemistry with catalytically active metals surfaces present in the tailing pond water including iron and copper. Waste heat from equipment and bitumen processing can provide heat to support treatment operations.

Figure 18:
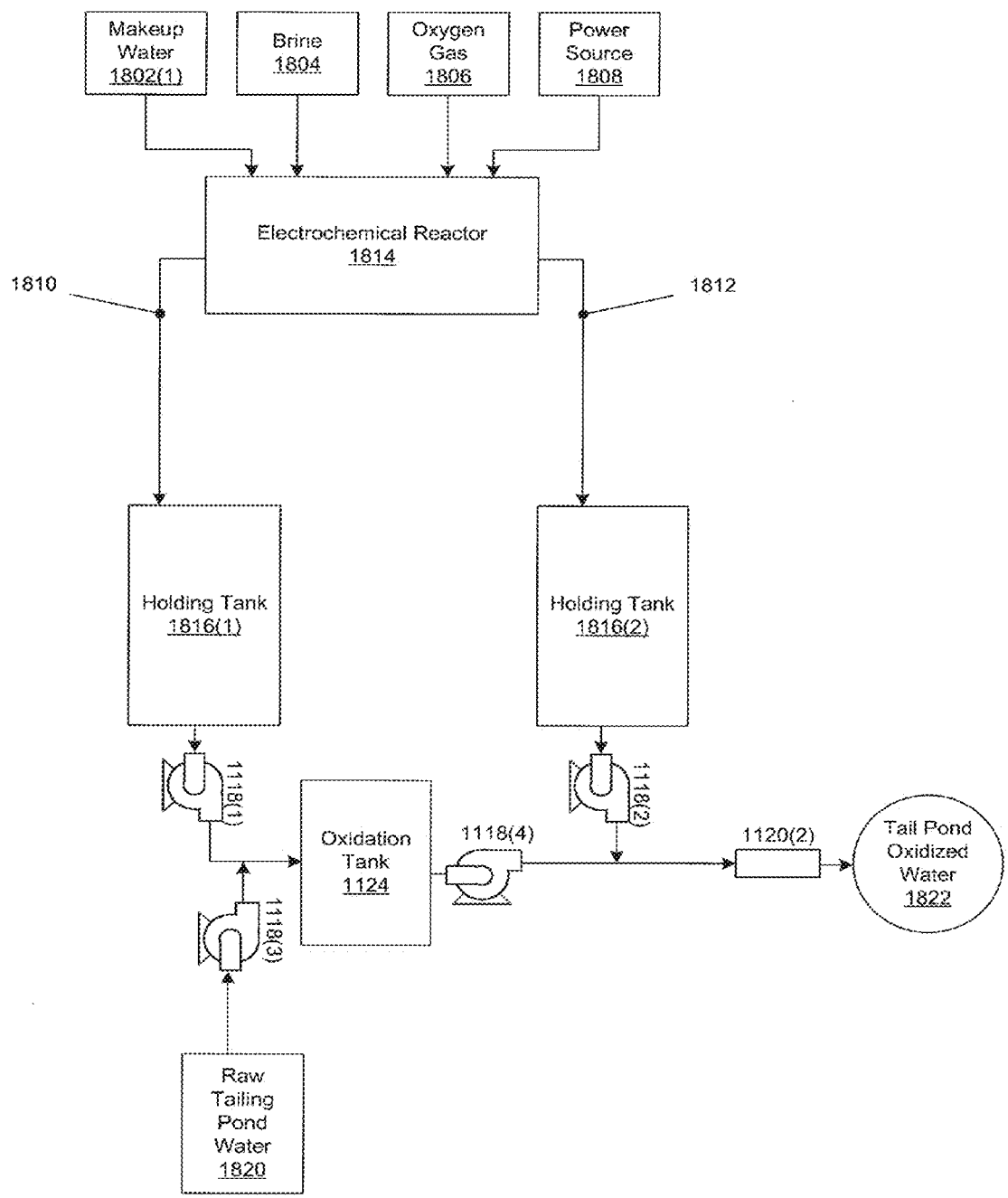
FIG. 18 shows one exemplary system used in example 17 to show an exemplar of producing a superoxide precursor formulation using an electrochemical generator used in a water treatment application, in one embodiment.

A generation system from FIG. 18 was used in the present example to show an exemplar of producing a superoxide precursor formulation using an electrochemical generator, in one embodiment. Superoxide concentrate 1124 and, optionally, acid concentrate 1126 are electrochemically generated using an electrochemical reactor 1114. Electrochemical reduction of oxygen is conducted at a suitable cathode and water is oxidized at a suitable anode in an electrochemical reactor 1114 in which the anode and cathode chambers are separated by a membrane. Oxygen gas 1106 and a 2 g/L aqueous sodium sulfate solution 1104 are supplied to the cathode while a 47.5 g/L aqueous sodium sulfate solution 1104 is supplied to the anode. A direct current 1108 is applied to the electrodes thereby driving the reduction of oxygen at the cathode to produce superoxide, hydrogen peroxide and sodium hydroxide as the majority products 1124 of the cathode, while water is oxidized at the anode to produce sodium bisulfate acid and oxygen gas as the majority products 1126 of the anode.

In this example the cathode product solution 1810 has a composition of approximately 8.2 g/L superoxide (as $O_2^-$), 5.0 g/L hydrogen peroxide (as $H_2O_2$), 1.3 g/L sodium hydroxide and a pH of about 12.6 (as NaOH) assuming a 40% current efficiency for oxygen reduction to superoxide and 50% current efficiency for oxygen reduction to hydrogen peroxide. The anode product solution 1812 has a composition of approximately 30 g/L sodium bisulfate and 13 g/L sodium sulfate assuming about 90% sodium sulfate to sodium bisulfate acid conversion. The anode to cathode product solution volume ratio is about 1.73.

The superoxide-containing cathode product solution 1810 is then diluted to its point of use concentration (i.e., 75 mg/L hydrogen peroxide, 124 mg/L superoxide, 20 mg/L NaOH) by mixing directly with raw tailing pond water 1820 in a 1:65.7 volume ratio. This mixture is held in an oxidation tank 1124 with a residence time of 6 to 24 hours after which the oxidized water is pH adjusted with the anode product solution 1126 in a 38.5:1 volume ratio. The pH-adjusted oxidized tailing pond water 1822 is then sent to a secondary treatment process. An example of a secondary treatment process is an aerobic bioreactor stage, to remove organic residuals and nitrification, followed by an anaerobic bioreactor stage, for sulfate reduction, removal of metal as sulfides and denitrification.

What is claimed is:

1. A method for generating a reactive oxygen species formulation, comprising:
   generating an alkaline hydrogen peroxide solution;
   mixing the alkaline hydrogen peroxide solution with an acyl donor such that a peracid concentrate is produced, wherein when the alkaline hydrogen peroxide solution and the acyl donor are mixed, the peracid concentrate has a molar ratio of hydrogen peroxide to acyl donor reactive groups ranging from about 1:1.25 to about 1.4, and maintaining, thereafter, the peracid concentrate pH value in a range from about pH 9.5 to about pH 12.5 until distributing the reactive oxygen species, and wherein the peracid concentrate has minimal hydrogen peroxide residual to minimize quenching of singlet oxygen.

2. The method of claim 1, wherein the alkaline hydrogen peroxide solution is generated from at least one of an alkali and a hydrogen peroxide concentrate or electrochemically.

3. The method of claim 1, wherein the reactive oxygen species formulation is a singlet oxygen precursor formulation.

4. The method of claim 1, wherein the acyl donor is an acetyl donor.

5. The method of claim 1, further comprising activating the reactive oxygen species using at least one of a Fenton or a Fenton-like catalyst, an ultrasound, an ultraviolet radiation or a thermal activation.

6. The method of claim 5, wherein the reactive oxygen species formed in the further activation step is a hydroxyl radical.

7. The method of claim 1, further comprising storing the alkaline hydrogen peroxide solution in a holding tank for at least one of immediate or future use.

8. The method of claim 1, further comprising distributing the reactive oxygen species to its point of use, wherein the reactive oxygen species is distributed in at least one form chosen from the group consisting of a liquid, an ice, a foam, an emulsion, a microemulsion and an aerosol.

9. The method of claim 1, wherein the alkaline hydrogen peroxide solution is electrochemically generated, has a pH value in the range of about pH 12.0 to about pH 12.5, and has a percent weight of hydrogen peroxide in the range of 0.1 to 3 wt %.

10. The method of claim 1, wherein the alkaline hydrogen peroxide solution is electrochemically generated, and wherein, during the step of electrochemically generating the alkaline hydrogen peroxide solution, an acid concentrate is co-generated.

11. The method of claim 1, wherein the reactive oxygen species is applied to the point of use by an application chosen from the group consisting of injection, flooding, spraying, and circulation.

12. The method of claim 1, wherein the peracid concentration undergoes the following chemical reaction:

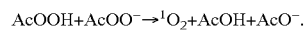

13. The method of claim 1, wherein the acyl donor is one of an oxygen-acyl or oxygen-acetyl donor or a nitrogen-acyl or nitrogen-acetyl donor.

14. The method of claim 1, wherein the peracid concentrate has a molar ratio of peracetic acid to hydrogen peroxide of at least about 32:1.

* * * * *

UNITED STATES PATENT AND TRADEMARK OFFICE
CERTIFICATE OF CORRECTION

PATENT NO. : 9,517,955 B2  
APPLICATION NO. : 14/020828  
DATED : December 13, 2016  
INVENTOR(S) : Buschmann Page 1 of 1

It is certified that error appears in the above-identified patent and that said Letters Patent is hereby corrected as shown below:

In the Claims

Claim 1, Column 50, Line 2, delete "1.4," and insert therefor --1:4,--.

Signed and Sealed this
Fourteenth Day of March, 2017

Michelle K. Lee
*Director of the United States Patent and Trademark Office*